United States Patent
Nolta et al.

(10) Patent No.: US 10,913,957 B2
(45) Date of Patent: *Feb. 9, 2021

(54) GENETICALLY MODIFIED MSC AND THERAPEUTIC METHODS

(71) Applicant: The Regents of the University of California, Oakland, CA (US)

(72) Inventors: Jan Nolta, Davis, CA (US); Karen Pepper, Davis, CA (US); Fernando Fierro, Davis, CA (US); Gerhard Bauer, Davis, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/153,211

(22) Filed: Oct. 5, 2018

(65) Prior Publication Data

US 2019/0276843 A1 Sep. 12, 2019

Related U.S. Application Data

(63) Continuation of application No. 15/351,415, filed on Nov. 14, 2016, now abandoned, which is a continuation of application No. 13/844,138, filed on Mar. 15, 2013, now abandoned, which is a continuation-in-part of application No. PCT/US2012/053537, filed on Aug. 31, 2012.

(51) Int. Cl.
| | | |
|---|---|---|
| *C12N 15/00* | (2006.01) | |
| *C12N 5/00* | (2006.01) | |
| *A01N 43/04* | (2006.01) | |
| *A01N 63/00* | (2020.01) | |
| *A61K 48/00* | (2006.01) | |
| *C12N 15/86* | (2006.01) | |

(52) U.S. Cl.
CPC ............ *C12N 15/86* (2013.01); *A61K 48/005* (2013.01); *C12N 2740/15043* (2013.01)

(58) Field of Classification Search
USPC ..... 435/320.1, 325; 424/93.21, 93.2; 514/44
See application file for complete search history.

(56) References Cited

U.S. PATENT DOCUMENTS

| | | | |
|---|---|---|---|
| 6,387,369 B1 | 5/2002 | Pittenger et al. | |
| 7,223,740 B2 | 5/2007 | Visser et al. | |
| 7,563,777 B2 | 7/2009 | Laguens et al. | |
| 8,580,755 B2 | 11/2013 | Xing et al. | |
| 8,728,458 B2 | 5/2014 | Anderson et al. | |
| 9,663,564 B2* | 5/2017 | Nolta .............. | C07K 14/52 |
| 2003/0103951 A1 | 6/2003 | Pittenger et al. | |
| 2003/0139333 A1 | 7/2003 | Pawliuk et al. | |
| 2003/0175410 A1 | 9/2003 | Campbell et al. | |
| 2003/0232431 A1 | 12/2003 | Law | |
| 2004/0009591 A1 | 1/2004 | Comer et al. | |
| 2004/0033949 A1 | 2/2004 | Bunting et al. | |
| 2004/0048375 A1 | 3/2004 | Alt | |
| 2005/0026288 A1 | 2/2005 | Harms et al. | |
| 2005/0153886 A1 | 7/2005 | Crystal et al. | |
| 2006/0275338 A1 | 12/2006 | Flugelman | |
| 2007/0010469 A1 | 1/2007 | Chan et al. | |
| 2007/0142282 A1 | 6/2007 | Alitalo et al. | |
| 2007/0184023 A1 | 8/2007 | Rasmussen et al. | |
| 2008/0032314 A1 | 2/2008 | Cameliet et al. | |
| 2008/0171689 A1 | 7/2008 | Williams et al. | |
| 2009/0010895 A1 | 1/2009 | Offen et al. | |
| 2009/0117617 A1 | 5/2009 | Holmes et al. | |
| 2009/0131866 A1 | 5/2009 | Zhang et al. | |
| 2009/0155220 A1 | 6/2009 | Losordo | |
| 2010/0254900 A1 | 10/2010 | Campbell et al. | |
| 2010/0267812 A1 | 10/2010 | Dodge et al. | |
| 2011/0201118 A1 | 8/2011 | Yang et al. | |
| 2011/0217274 A1 | 9/2011 | Reld | |
| 2011/0256160 A1 | 10/2011 | Meiron et al. | |
| 2012/0076763 A1 | 3/2012 | Anderson et al. | |
| 2012/0087901 A1 | 4/2012 | Nelson | |
| 2014/0004201 A1 | 1/2014 | Lewis et al. | |
| 2015/0139952 A1 | 5/2015 | Webster | |

FOREIGN PATENT DOCUMENTS

| | | |
|---|---|---|
| WO | WO-2014/035433 A1 | 3/2014 |
| WO | WO-2014/036524 A2 | 3/2014 |
| WO | WO-2014/144815 A2 | 9/2014 |

OTHER PUBLICATIONS

Ball, et al., "Vascular endothelial growth factor can signal through platelet-derived growth factor receptors", The Journal of Cell Biology, vol. 177, May 7, 2007, pp. 489-500.

Bauer, et al., "In VivoBiosafety Model to Assess the Risk of Adverse Events From Retroviral and Lentiviral Vectors", Mol Ther. 16, Jul. 2008, pp. 1308-1315.

Blumenthal, et al., "Effective Suicide Gene Therapy for Leukemia in a Model of Insertional Oncogenesis in Mice", Molecular Therapy, vol. 15, Jan. 2007, pp. 183-192.

Caplan, et al., "Mesenchymal Stem Cells as Trophic Mediators", Journal of Cellular Bichemistry, 98, Aug. 1, 2006, pp. 1076-1084.

Dao, et al., "Cytokine Production from Engineered Primary Human Stromal Cells Influences Human Hematopoiesis in an In Vivo Xenograft Model", Stem Cells 15, 1997, pp. 443-454.

Deuse, et al., "Hepatocyte Growth Factor or Vascular Endothelial Growth Factor Gene Transfer Maximizes Mesenchymal Stem Cell-Based Myocardial Salvage After Acute Myocardial Infarction", Circulation 120, Sep. 15, 2009, pp. S247-S254.

(Continued)

*Primary Examiner* — Michael C Wilson
(74) *Attorney, Agent, or Firm* — Foley & Lardner LLP

(57) ABSTRACT

This disclosure relates to vectors, isolated cells, compositions, and methods for the treatment of critical limb ischemia and associated disorders. One aspect of the disclosure relates to a vector comprising a nucleic acid encoding a 165A isoform VEGF protein and a promoter that regulates expression of the nucleic acid encoding the VEGF.

20 Claims, 23 Drawing Sheets

Specification includes a Sequence Listing.

(56) References Cited

OTHER PUBLICATIONS

Fierro, et al., "Effects on Proliferation and Differentiation of Multipotent Bone Marrow Stromal Cells Engineered to Express Growth Factors for Combined Cell and Gene Therapy", Stem Cells 29, 2011, pp. 1727-1737.
Gao, et al., "A promising strategy for the treatment of ischemic heart disease: Mesenchymal stem cell-mediated vascular endothelial growth factor gene transfer in rats", Can J Cardiol, vol. 23, Sep. 2007, pp. 891-898.
Gnecchi, et al., "Bone Marrow-Derived Mesenchymal Stem Cells: Isolation, Expansion, Characterization, Viral Transduction, and Production of Conditioned Medium", Stem Cells in Regenerative Medicine: Methods and Protocols, vol. 482, 2009, pp. 281-294.
Gruenloh, et al., "Characterization and in Vivo Testing of Mesenchymal Stem Cells Derived From Human Embryonic Stem Cells", Tissue Engineering: Part A, vol. 17, Nos. 11 and 12, Jun. 2011, pp. 1517-1525.
Huang, et al., "Mesenchymal stem cells for vascular regeneration", Regenerative Medicine 3, Nov. 2008, pp. 877-892.
Kinnaird, et al., "Local Delivery of Marrow-Derived Stromal Cells Augments Collateral Perfusion Through Paracrine Mechanisms", Circulation 109, Mar. 30, 2004), pp. 1543-1549.
Kusumanto, et al., "Therapeutic angiogenesis with vascular endothelial growth factor in peripheral and coronary artery disease: a revie", International Journal Cardiovascular Interventions 5, 2003, pp. 27-34.
Lasala, et al., "Vascular disease and stem cell therapies", British Medical Bulletin 98, May 17, 2011, pp. 187-197.
Losordo, et al., "Therapeutic Angiogenesis and Vasculogenesis for Ischemic Disease. Part I: Angiogenic Cytokines", Circulation 109, Jun. 1, 2004, pp. 2487-2491.
Losordo, et al., "Therapeutic Angiogenesis and Vasculogenesis for Ischemic Disease. Part II: Cell-Based Therapies", Circulation 109, Jun. 8, 2004, pp. 2692-2697.
Matsumot, et al., "Vascular Endothelial Growth Factor-Expressing Mesenchymal Stem Cell Transplantation for the Treatment of Acute Myocardial Infarction", Arterioscler Thromb Vase Biol 25, Jun. 2005, pp. 1168-1173.
Meyerrose, et al., "Lentiviral-Transduced Human Mesenchymal Stem Cells Persistently Express Therapeutic Levels of Enzyme in a Xenotransplantation Model of Human Disease", Stem Cells 26, Jul. 2008, pp. 1713-1722.
Meyerrose, et al., "Mesenchymal stem cells for the sustained in vivo delivery of bioactive factors", Advanced Drug Delivery Reviews 62, Sep. 30, 2010, pp. 1167-1174.
Nolta, et al., "Comparison of the Effects of Growth Factors on Retroviral Vector-Mediated Gene Transfer and the Proliferative Status of Human Hematopoietic Progenitor Cells", Human Gene Therapy 1, 1990, pp. 257-268.
Nolta, et al., "Transduction of pluripotent human hematopoietic stem cells demonstrated by clonal analysis after engraftment in immune-deficient mice", Proc. Natl. Acad. Sci. USA, vol. 93, Mar. 1996, pp. 2414-2419.
Pati, et al., "Human Mesenchymal Stem Cells Inhibit Vascular Permeability by Modulating Vascular Endothelial Cadherin/beta-Catenin Signaling", Stem Cells and Development, vol. 20, No. 1, Jan. 2011, pp. 89-101.
Rissanen, et al., "Gene Transfer for Therapeutic Vascular Growth in Myocardial and Peripheral Ischemia", Advances in Genetics, vol. 52, 2004, pp. 117-164.
Rosova, et al. "Hypoxic Preconditioning Results in Increased Motility and Improved Therapeutic Potential of Human Mesenchymal Stem Cells", Stem Cells, Aug. 2008, 26(8), pp. 2173-2182.
Rosova, et al., "shRNA-mediated Decreases in c-Met Levels Affect the Differentiation Potential of Human Mesenchymal Stem Cells and Reduce Their Capacity for Tissue Repair", Tissue Engineering: Part A, vol. 16, No. 8, Aug. 2010, pp. 2627-2639.
Salem, et al., "Mesenchymal Stromal Cells: Current Understanding and Clinical Status", Stem Cells 28, Mar. 31, 2010, pp. 585-596.
Satija, et al., "Mesenchymal stem cell-based therapy: a new paradigm in regenerative medicine", J. Cell. Mol. Med., vol. 13, Nov.-Dec. 2009, pp. 4385-4402.
Shyu, et al., "Intramuscular Vascular Endothelial Growth Factor Gene Therapy in Patients with Chronic Critical Leg Ischemia", The American Journal of Medicine, vol. 114, Feb. 1, 2003, pp. 85-92.
Tsark, et al., "IL-7 Enhances the Responsiveness of Human T Cells That Develop in the Bone Marrow of Athymic Mice", The Journal of Immunology 166, 2001, pp. 170-181.
Wang, et al., "Bioenergetic and functional consequences of stem cell-based VEGF delivery in pressure-overloaded swine hearts", Am J Physiol Heart Circ Physiol 290, 2006, pp. H1393-1405.
Wirthlin, et al., "Human Stem Cells for Tissue Repair", Biology of Blood and Marrow Transplantation 14, Jan. 2008, pp. 151-153.
Yang, et al., "Genetic engineering of human stem cells for enhanced angiogenesis using biodegradable polymeric nanoparticles", PNAS, vol. 107, Feb. 23, 2010, pp. 3317-3322.
Aframian D J et al: "Using HSV-thymidine kinase for safety in an allogenic salivary graft cell line," Tissue Engineering, Larchmont, NY, US, vol. 7, No. 4, Aug. 1, 2001 (Aug. 1, 2001), XP002761134, ISSN: 1076-3279.
Akeson Ann L et al: "Temporal and spatial regulation of VEGF-A controls vascular patterning in the embryonic lunch," Developmental Biology, vol. 264, No. 2, Dec. 15, 2003 (Dec. 15, 2003), XP002762759, ISSN: 0012-1606.
Al-Khaldi, et al., "Postbatal bone marrow stromal cells elicit a potent VEGF-dependent neoangiogenic response in vivo", Gene Therapy, 2003, vol. 10, p. 621-629.
Bai, X-F. et al. (2005) "Expression of Human VEGF165 Gene in Rat Bone Marrow Stromal Cells in vitro," Journal of Sichuan University, Medical Science Edition 36(4):468-470.
Baumgartner, I. (2004) "Vascular endothelial growth factor (VEGF) gene therapy for critical limb ischemia," Progress in Gene Therapy 2:65-106.
Cai, S. et al. (2002) "Expression of human VEGF(121) cDNA in mouse bone marrow stromal cells," Chinese Medical Journal 115(6):914-918.
Chang David S et al. "Adeno-associated viral vector-mediated gene transfer of VEGF normalizes skeletal muscle oxygen tension and induces arteriogenesis in ischemic rat hindlimb.", Molecular Therapy: The Journal of the American Society of Gene Therapy,Jan. 2003 7:1, pp. 44-51.
Chen, B-S. et al. (2011) "Tissue engineering of bladder using vascular endothelial growth factor gene-modified endothelial progenitor cells," International Journal of Artificial Organs 34(12):1137-1146.
Chen, H.K. et al. (2005) "Combined cord blood stem cells and gene therapy enhances angiogenesis and improves cardiac performance in mouse after acute myocardial infarction," European J. Clin. Investigation 35:677-686.
Crystal, R.G. (1995) "Transfer of Genes to Human: Early Lessons and Obstacles to Success," Science 270:404-410.
Dai, J. et al. (2007) "Recombinant adeno-associated virus vector hybrids efficiently target different skeletal cells," Frontiers in Bioscience 12:4280-4287.
Database BIOSIS [Online] Biosciences Information Service, Philadelphia, PA, US; May 2010 (May 2010), Fang Yu Xiang et al: "Development of Chimeric Gene Regulators for Cancer-specific Gene Therapy with both Transcriptional and Translational Targeting," Database accession No. PREV201000282618; & Molecular Biotechnology, vol. 45, No. 1, May 2010 (May 2010), ISSN 1073-6085, DOI: 10.1007/S12033-010-9244-Y.
Database Medline [Online] US National Library of Medicine (NLM), Bethesda, MD, US; Sep. 1996 (Sep. 1996), Zhou A et al: "[Molecular bypass, the application of VEGF to gene therapy of limb ischemia]," XP002762757, Database accession No. NLM9275547.
Deonarain, M.P. (1998) "Ligand-targeted receptor-mediated vectors for gene delivery," Expert Opin. Ther. Patents 8(1):53-69.
Extended European Search Report dated Oct. 31, 2016, from application No. 14765183.0.
Fierro Fernando A et al: "Effects on Proliferation and Differentiation of Multipotent Bone Marrow Stromal Cells Engineered to Express

(56) References Cited

OTHER PUBLICATIONS

Growth Factors for Combined Cell and Gene Therapy," Stem Cells (Miamisburg), vol. 29, No. 11, Nov. 2011 (Nov. 2011), XP002717241.
Final Office Action dated May 10, 2019, from U.S. Appl. No. 15/607,638.
Final Office Action in U.S. Appl. No. 13/844,138, dated Oct. 15, 2015.
Gao, Q-W. et al. (2009) "Expression of recombinant adenovirus-mediated VEGF165 in bone marrow stromal cells of rats," Med. J. Chin. PLA 34(2):192-195.
Hou, H. et al. (2009) "Enhancement of bone formation by genetically-engineered bone marrow stromal cells expressing BMP-2, VEGF and angiopoietin-1," Biotechnology Letters 31(8):1183-1189.
International Search Report and Written Opinion for International Application No. PCT/US2012/053537, dated Jun. 27, 2013, 13 pages.
International Search Report and Written Opinion for International Application No. PCT/US2013/057721, dated Mar. 3, 2014, 19 pages.
International Search Report and Written Opinion for International Application No. PCT/US2014/029386, dated Aug. 29, 2014, 13 pages.
Iwagaro, H. et al. (2002) "Endothelial Progenitor Cell Vascular Endothelial Growth Factor Gene Transfer for Vascular Regeneration," Circulation 105:732-738.
Johnson-Saliba, M. et al. (2001) "Gene Therapy: Optimising DNA Delivery to the Nucleus," Curr. Drug. Targets 2:371-399.
Li, S.R. et al. (2007) "Influence of bone marrow stem cell transplantation on the ventricular remodeling after acute myocardial infarction," Journal of Clinical Rehabilitative Tissue Engineering Research 11(28):5574-5579.
Liu, D-P. et al. (2010) "Construction of adenovirus vectors carrying VEGF(121)-FLAG and hrGFP-1 and their expressions in bone marrow stromal stem cells," J Clin Rehab. Tissue Eng. Res. 14(45):8539-8543.
Lu, Y. et al. (2006) "Construction of recombinant adenovirus carrying human bone morphogenetic protein 2 and vascular endothelial growth factor 165 gene and its coexpression in rabbit marrow stromal stem cells," Chinese J Clin Rehab.10(33):56-59.
Meyerrose, T. et al. (2010) "Mesenchymal stem cells for the sustained in vivo delivery of bioactive factors," Advanced Drug Delivery Rev.:1-8.
Miller, N. et al. (1995) "Targeted vectors for gene therapy," FASEB J. 9:190-199.
Morse, M.A. (2001) "Technology evaluation: VEGF165 gene therapy, Valentis Inc.," Current Opinion in Molecular Therapeutics 3(1):97-101.
Naidoo Jerusha et al: "Gene regulation systems for gene therapy applications in the central nervous system," Neurology Research International, vol. 2012, 595410, 2012, XP002762760, ISSN: 2090-1860, DOI: 10.115/2012/595410.
Non-Final Office Action dated Aug. 6, 2018, from U.S. Appl. No. 15/607,638.
Non-Final Office Action in U.S. Appl. No. 13/844,138, dated Jan. 20, 2015.

Pantuck et al., "Optimizing Prostate Cancer Suicide Gene Therapy Using Herpes Simplex Virus Thymidine Kinase Active Site Variants." Human Gene Therapy 13(7):777-789 (2002).
Park, et al., "The Vascular Endothelial Growth Factor (VEGF) Isoforms: Differential Deposition into the Subepithelial Extracellular Matrix and Bioactivity of Extracellular Matrix-bound VEGF", Molecular Biology of the Cell, 1993, vol. 4, p. 1317-1326, Dec. 1993.
Pfeifer, A. et al. (2001) "Gene Therapy: Promises and Problems," Annu. Rev. Genomics. Hum. Genet. 2:177-211.
Rennel, et al., "The endogenous anti-angiogenic VEGF isoform, VEGF165b inhibits human tumour growth in mice", British Journal of Cancer, 2008, 98, p. 1250-1257.
Restriction Requirement for U.S. Appl. No. 13/844,138, dated May 30, 2014, 10 pages.
Rissanen, T.T. et al. (2004) "Gene Transfer of Therapeutic Vascular Growth in Myocardial and Peripheral Ischemia," Adv. In Genetics 52:117-164.
Romanov, Y.A. et al. (2003) "Searching for Alternative Sources of Postnatal Human Mesenchymal Stem Cells: Candidate MSC-Like Cells from Umbilical Cord," Stem Cells 21:105-110.
Shoji, Y. et al. (2004) "Current Status of Delivery Systems to Improve Target Efficacy of Oligonucleotides," Current Pharmaceutical Design 10:785-796.
Song, J. et al. (2005) "A study on the mobilization of stem cells by VEGF-165 and angiopoietin-1," Jiangsu Med. J. 31(5):360-362.
Symes, J.F. et al. (2004) "Angiogenic VEGF gene therapy for refractory angina pectoris," Progress in Gene Therapy 2:107-131.
Tiberghien, P. et al. (2001) "Administration of herpes simplex-thymidine kinase-expressing donor T cells with a T-cell-depleted allogeneic marrow graft," Blood 97(1):63-72.
U.S. Notice of Allowance dated Mar. 7, 2017, from U.S. Appl. No. 14/776,673.
U.S. Office Action dated Apr. 6, 2018, from U.S. Appl. No. 15/351,415.
U.S. Office Action dated Jun. 16, 2016, from U.S. Appl. No. 14/776,673.
U.S. Office Action dated Oct. 28, 2016, from U.S. Appl. No. 14/776,673.
Verma, I.M. et al. (1997) "Gene therapy 013 promises, problems and prospects," Nature 389:239-242.
Wei, F-J. et al. (2010) "Combination therapy of adeno-associated virus-mediated expression of vascular endothelial growth factor gene and bone marrow mesenchymal stem cells for limb ischemia," Chin J Geriatr. 29(10):858-862.
Williams, et al., "Mesenchumal Stem Cells Biology, Pathophysiology, Translational Findings, and Therapeutic Implications for Cardiac Disease", Circulation Research, 2011, vol. 109, p. 907-909.
Yla-Herttuala, S. et al. (2007) "Vascular Endothelial Growth Factors: Biology and Current Status of Clinical Applications in Cardiovascular Medicine," Journal of the American College of Cardiology 49(10):1015-1026.
Zufferey et al., "Woodchuck Hepatitis Virus Posttranscriptional Regulatory Element Enhances Expression of Transgenes Delivered by Retroviral Vectors." J. Virol. 73(4):2886-2892 (1999).

\* cited by examiner

SEQUENCE LISTING

<160> NUMBER OF SEQ ID NOS: 23

<210> SEQ ID NO 1
<211> LENGTH: 627
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gaattcgccc ttcctgagat caccggtagg agggccatca tgaactttct gctgtcttgg     60
gtgcattgga gccttgcctt gctgctctac ctccaccatg ccaagtggtc ccaggctgca    120
cccatggcag aaggaggagg gcagaatcat cacgaagtgg tgaagttcat ggatgtctat    180
cagcgcagct actgccatcc aatcgagacc ctggtggaca tcttccagga gtaccctgat    240
gagatcgagt acatcttcaa gccatcctgt gtgcccctga tgcgatgcgg gggctgctgc    300
aatgacgagg gcctggagtg tgtgcccact gaggagtcca acatcaccat gcagattatg    360
cggatcaaac tcaccaagg ccagcacata ggagagatga gcttcctaca gcacaacaaa    420
tgtgaatgca gaccaaagaa agatagagca agacaagaaa atccctgtgg gccttgctca    480
gagcggagaa agcatttgtt tgtacaagat ccgcagacgt gtaaatgttc ctgcaaaaac    540
acagactcgc gttgcaaggc gaggcagctt gagttaaacg aacgtacttg cagatgtgac    600
aagccgaggc ggtgaaaggg cgaattc                                        627

<210> SEQ ID NO 2
<211> LENGTH: 9448
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
caggtggcac ttttcgggga aatgtgcgcg gaacccctat ttgtttattt ttctaaatac     60
attcaaatat gtatccgctc atgagacaat aaccctgata aatgcttcaa taatattgaa    120
aaaggaagag tatgagtatt caacatttcc gtgtcgccct tattcccttt tttgcggcat    180
tttgccttcc tgtttttgct cacccagaaa cgctggtgaa agtaaaagat gctgaagatc    240

```
agttgggtgc acgagtgggt tacatcgaac tggatctcaa cagcggtaag atccttgaga    300
gttttcgccc cgaagaacgt tttccaatga tgagcacttt taaagttctg ctatgtggcg    360
cggtattatc ccgtattgac gccgggcaag agcaactcgg tcgccgcata cactattctc    420
agaatgactt ggttgagtac tcaccagtca cagaaaagca tcttacggat ggcatgacag    480
taagagaatt atgcagtgct gccataacca tgagtgataa cactgcggcc aacttacttc    540
tgacaacgat cggaggaccg aaggagctaa ccgcttttt gcacaacatg ggggatcatg    600
taactcgcct tgatcgttgg gaaccggagc tgaatgaagc cataccaaac gacgagcgtg    660
acaccacgat gcctgtagca atggcaacaa cgttgcgcaa actattaact ggcgaactac    720
ttactctagc ttcccggcaa caattaatag actggatgga ggcggataaa gttgcaggac    780
cacttctgcg ctcggccctt ccggctggct ggtttattgc tgataaatct ggagccggtg    840
agcgtgggtc tcgcggtatc attgcagcac tggggccaga tggtaagccc tcccgtatcg    900
tagttatcta cacgacgggg agtcaggcaa ctatggatga acgaaataga cagatcgctg    960
agataggtgc ctcactgatt aagcattggt aactgtcaga ccaagtttac tcatatatac   1020
tttagattga tttaaaactt cattttaat ttaaaaggat ctaggtgaag atcctttttg   1080
ataatctcat gaccaaaatc ccttaacgtg agttttcgtt ccactgagcg tcagaccccg   1140
tagaaaagat caaaggatct cttgagatc ctttttttct gcgcgtaatc tgctgcttgc   1200
aaacaaaaaa accaccgcta ccagcggtgg tttgtttgcc ggatcaagag ctaccaactc   1260
tttttccgaa ggtaactggc ttcagcagag cgcagatacc aaatactgtc cttctagtgt   1320
agccgtagtt aggccaccac ttcaagaact ctgtagcacc gcctacatac ctcgctctgc   1380
taatcctgtt accagtggct gctgccagtg gcgataagtc gtgtcttacc gggttggact   1440
caagacgata gttaccggat aaggcgcagc ggtcgggctg aacggggggt tcgtgcacac   1500
agcccagctt ggagcgaacg acctacaccg aactgagata cctacagcgt gagctatgag   1560
aaagcgccac gcttcccgaa gggagaaagg cggacaggta tccggtaagc ggcagggtcg   1620
gaacaggaga gcgcacgagg gagcttccag ggggaaacgc ctggtatctt tatagtcctg   1680
tcgggtttcg ccacctctga cttgagcgtc gatttttgtg atgctcgtca gggggggcgga   1740
gcctatggaa aaacgccagc aacgcggcct ttttacggtt cctggccttt tgctggcctt   1800
ttgctcacat gttctttcct gcgttatccc ctgattctgt ggataaccgt attaccgcct   1860
ttgagtgagc tgataccgct cgccgcagcc gaacgaccga gcgcagcgag tcagtgagcg   1920
aggaagcgga agagcgccca atacgcaaac cgcctctccc cgcgcgttgg ccgattcatt   1980
aatgcagctg gcacgacagg tttcccgact ggaaagcggg cagtgagcgc aacgcaatta   2040
atgtgagtta gctcactcat taggcacccc aggctttaca ctttatgctt ccggctcgta   2100
tgttgtgtgg aattgtgagc ggataacaat ttcacacagg aaacagctat gaccatgatt   2160
acgccaagcg cgcaattaac cctcactaaa gggaacaaaa gctggagctg caagcttggc   2220
cattgcatac gttgtatcca tatcataata tgtacattta tattggctca tgtccaacat   2280
taccgccatg ttgacattga ttattgacta gttattaata gtaatcaatt acggggtcat   2340
tagttcatag cccatatatg gagttccgcg ttacataact tacggtaaat ggcccgcctg   2400
gctgaccgcc caacgacccc cgcccattga cgtcaataat gacgtatgtt cccatagtaa   2460
cgccaatagg gactttccat tgacgtcaat gggtggagta tttacggtaa actgcccact   2520
tggcagtaca tcaagtgtat catatgccaa gtacgccccc tattgacgtc aatgacggta   2580
```

```
aatggcccgc ctggcattat gcccagtaca tgaccttatg ggactttcct acttggcagt    2640
acatctacgt attagtcatc gctattacca tggtgatgcg gttttggcag tacatcaatg    2700
ggcgtggata gcggtttgac tcacggggat ttccaagtct ccaccccatt gacgtcaatg    2760
ggagtttgtt ttggcaccaa aatcaacggg actttccaaa atgtcgtaac aactccgccc    2820
cattgacgca aatgggcggt aggcgtgtac ggtgggaggt ctatataagc agagctcgtt    2880
tagtgaaccg ggtctctct ggttagacca gatctgagcc tgggagctct ctggctaact    2940
agggaaccca ctgcttaagc ctcaataaag cttgccttga gtgcttcaag tagtgtgtgc    3000
ccgtctgttg tgtgactctg gtaactagag atccctcaga cccttttagt cagtgtggaa    3060
aatctctagc agtggcgccc gaacagggac ctgaaagcga aagggaaacc agaggagctc    3120
tctcgacgca ggactcggct tgctgaagcg cgcacggcaa gaggcgaggg gcggcgactg    3180
gtgagtacgc caaaaatttt gactagcgga ggctagaagg agagagatgg gtgcgagagc    3240
gtcagtatta gcgggggag aattagatcg cgatgggaaa aaattcggtt aaggccaggg    3300
ggaaagaaaa aatataaatt aaaacatata gtatgggcaa gcaggagct agaacgattc    3360 gcagttaatc ctggcctgtt agaaacatca gaaggctgta gacaaatact gggacagcta    3420
caaccatccc ttcagacagg atcagaagaa cttagatcat tatataatac agtagcaacc    3480
ctctattgtg tgcatcaaag gatagagata aaagacacca aggaagcttt agacaagata    3540
gaggaagagc aaaacaaaag taagaccacc gcacagcaag cggccgctga tcttcagacc    3600
tggaggagga gatatgaggg acaattggag aagtgaatta tataaatata agtagtaaa    3660 aattgaacca ttaggagtag cacccaccaa ggcaaagaga agagtggtgc agagagaaaa    3720
aagagcagtg ggaataggag ctttgttcct tgggttcttg ggagcagcag gaagcactat    3780
gggcgcagcc tcaatgacgc tgacggtaca ggccagacaa ttattgtctg gtatagtgca    3840
gcagcagaac aatttgctga gggctattga ggcgcaacag catctgttgc aactcacagt    3900
ctggggcatc aagcagctcc aggcaagaat cctggctgtg aaagatacc taaaggatca    3960 acagctcctg gggatttggg gttgctctgg aaaactcatt tgcaccactg ctgtgccttg    4020
gaatgctagt tggagtaata atctctgga acagattgga atcacacgac ctggatggag    4080
tgggacagag aaattaacaa ttacacaagc ttaatacact ccttaattga agaatcgcaa    4140
aaccagcaag aaaagaatga acaagaatta ttggaattag ataaatgggc aagtttgtgg    4200
aattggttta acataacaaa ttggctgtgg tatataaaat tattcataat gatagtagga    4260
ggcttggtag gtttaagaat agttttttgct gtactttcta tagtgaatag agttaggcag    4320
ggatattcac cattatcgtt tcagacccac ctcccaaccc cgaggggacc cgacaggccc    4380
gaaggaatag aagaagaagg tggagagaga cagagacag gatccattcg attagtgaac    4440
ggatctcgac ggtatcgatc tcgacacaaa tggcagtatt catccacaat tttaaaagaa    4500 aagggggat tgggggtac agtgcagggg aaagaatagt agacataata gcaacagaca    4560
tacaaactaa agaattacaa aaacaaatta caaaaattca aaattttcgg gtttattaca    4620
gggacagcag agatccagtt tgggtcgagg attcgagttt actccctatc agtgatagag    4680
aacgtatgtc gagtttactc cctatcagtg atagagaacg atgtcgagtt tactccctat    4740
cagtgataga gaacgtatgt cgagtttact ccctatcagt gatagagaac gtatgtcgag    4800
tttactccct atcagtgata gagaacgtat gtcgagttta tccctatcag tgatagagaa    4860
cgtatgtcga gtttactccc tatcagtgat agagaacgta tgtcgaggta ggcgtgtacg    4920
gtgggaggcc tatataagca gagctcgttt agtgaaccgt cagatcgcct ggagaattcg    4980
```

```
cccttcctga gatcaccggt aggagggcca tcatgaactt tctgctgtct tgggtgcatt    5040
ggagccttgc cttgctgctc tacctccacc atgccaagtg gtcccaggct gcacccatgg    5100
cagaaggagg agggcagaat catcacgaag tggtgaagtt catggatgtc tatcagcgca    5160
gctactgcca tccaatcgag accctggtgg acatcttcca ggagtaccct gatgagatcg    5220
agtacatctt caagccatcc tgtgtgcccc tgatgcgatg cggggggctgc tgcaatgacg    5280 agggcctgga gtgtgtgccc actgaggagt ccaacatcac catgcagatt atgcggatca    5340
aacctcacca aggccagcac ataggagaga tgagcttcct acagcacaac aaatgtgaat    5400
gcagaccaaa gaaagataga gcaagacaag aaaatccctg tgggccttgc tcagagcgga    5460
gaaagcattt gtttgtacaa gatccgcaga cgtgtaaatg ttcctgcaaa aacacagact    5520
cgcgttgcaa ggcgaggcag cttgagttaa acgaacgtac ttgcagatgt gacaagccga    5580
ggcggtgaaa gggcgaattc taccgggtag gggaggcgct tttcccaagg cagtctggag    5640
catgcgcttt agcagccccg ctggcacttg gcgctacaca agtggcctct ggcctcgcac    5700
acattccaca tccaccggta ggcgccaacc ggctccgttc tttggtggcc ccttcgcgcc    5760
accttctact cctcccctag tcaggaagtt ccccccgcc ccgcagctcg cgtcgtgcag    5820
gacgtgacaa atggaagtag cacgtctcac tagtctcgtg cagatggaca gcaccgctga    5880
gcaatggaag cgggtaggcc tttggggcag cggccaatag cagctttgct ccttcgcttt    5940
ctgggctcag aggctgggaa ggggtgggtc cggggcggg ctcaggggcg ggctcagggg    6000
cggggcgggc gcccgaaggt cctccggagg cccggcattc tcgcacgctt caaaagcgca    6060
cgtctgccgc gctgttctcc tcttcctcat ctccgggcct ttcgaccatc tagatcagga    6120
tcaattcacc atgtctagac tggacaagag caaagtcata aacggcgctc tggaattact    6180
caatggagtc ggtatcgaag gcctgacgac aaggaaactc gctcaaaagc tgggagttga    6240
gcagcctacc ctgtactggc acgtgaagaa caagcgggcc ctgctcgatg ccctgccaat    6300
cgagatgctg acaggcatc atacccactt ctgccccctg gaaggcgagt catggcaaga    6360
cttcctgcgg aacaacgcca agtcattccg ctgtgctctc ctctcacatc gcgacggggc    6420
taaagtgcat ctcggcaccc gcccaacaga gaaacagtac gaaaccctgg aaaatcagct    6480
cgcgttcctg tgtcagcaag gcttctccct ggagaacgca ctgtacgctc tgtccgccgt    6540
gggccacttt acactgggct gcgtattgga ggaacaggag catcaagtag caaaagagga    6600
aagagagaca cctaccaccg attctatgcc cccacttctg agacaagcaa ttgagctgtt    6660
cgaccggcag ggagccgaac ctgccttcct tttcggcctg gaactaatca tatgtggcct    6720
ggagaaacag ctaaagtgcg aaagcggcgg gccggccgac gcccttgacg attttgactt    6780
agacatgctc ccagccgatg cccttgacga ctttgacctt gatatgctgc ctgctgacgc    6840
tcttgacgat tttgaccttg acatgctccc cggggaagt ggcgcgacca actttagcct    6900
gctgaaacag gcgggcgatg tggaagaaaa cccaggaccg atggcttcgt accccggcca    6960
tcaacacgcg tctgcgttcg accaggctgc gcgttctcgc ggccatagca accgacgtac    7020
ggcgttgcgc cctcgccggc agcaagaagc cacggaagtc cgcccggagc agaaaatgcc    7080
cacgctactg cgggtttata tagacggtcc ccacgggatg gggaaaacca ccaccacgca    7140
actgctggtg gccctgggtt cgcgcgacga tatcgtctac gtacccgagc cgatgactta    7200
ctggcgggtg ctgggggctt ccgagacaat cgcgaacatc tacaccacac aacaccgcct    7260
cgaccagggt gagatatcgg ccggggacgc ggcggtggta atgacaagcg cccagataac    7320
```

```
aatgggcatg ccttatgccg tgaccgacgc cgttctggct cctcatatcg ggggggaggc   7380
tgggagctca catgccccgc ccccggccct caccctcatc ttcgaccgcc atcccatcgc   7440
cgccctcctg tgctacccgg ccgcgcgata ccttatgggc agcatgaccc cccaggccgt   7500
gctggcgttc gtggccctca tcccgccgac cttgcccggc acaaacatcg tgttgggggc   7560
ccttccggag gacagacaca tcgaccgcct ggccaaacgc cagcgccccg gcgagcggct   7620
tgacctggct atgctggccg cgattcgccg cgtttacggg ctgcttgcca atacggtgcg   7680
gtatctgcag ggcggcgggt cgtggcggga ggattgggga cagcttttcgg ggacggccgt   7740
gccgccccag ggtgccgagc cccagagcaa cgcgggccca cgaccccata tcggggacac   7800
gttatttacc ctgtttcggg cccccgagtt gctggccccc aacggcgacc tgtataacgt   7860
gtttgcctgg gccttggacg tcttggccaa acgcctccgt cccatgcacg tctttatcct   7920
ggattacgac caatcgcccg ccggctgccg ggacgccctg ctgcaactta cctccgggat   7980
ggtccagacc cacgtcacca cccccggctc cataccgacg atatgcgacc tggcgcgcac   8040
gtttgcccgg gagatggggg aggctaactg acttaagctc tagccaattc gagctcggta   8100
cctttaagac caatgactta caaggcagct gtagatctta gccacttttt aaaagaaaag   8160
gggggactgg aagggctaat tcactcccaa cgaagacaag atctgctttt tgcttgtact   8220
gggtctctct ggttagacca gatctgagcc tgggagctct ctggctaact agggaaccca   8280
ctgcttaagc ctcaataaag cttgccttga gtgcttcaag tagtgtgtgc ccgtctgttg   8340
tgtgactctg gtaactagag atccctcaga cccttttagt cagtgtggaa aatctctagc   8400
agtagtagtt catgtcatct tattattcag tatttataac ttgcaaagaa atgaatatca   8460
gagagtgaga ggaacttgtt tattgcagct tataatggtt acaaataaag caatagcatc   8520
acaaatttca caaataaagc atttttttca ctgcattcta gttgtggttt gtccaaactc   8580
atcaatgtat cttatcatgt ctggctctag ctatcccgcc cctaactccg cccatcccgc   8640
ccctaactcc gcccagttcc gcccattctc cgccccatgg ctgactaatt ttttttattt   8700
atgcagaggc cgaggccgcc tcggcctctg agctattcca gaagtagtga ggaggctttt   8760
ttggaggcct aggcttttgc gtcgagacgt acccaattcg ccctatagtg agtcgtatta   8820
cgcgcgctca ctggccgtcg ttttacaacg tcgtgactgg gaaaaccctg gcgttaccca   8880
acttaatcgc cttgcagcac atccccnttt cgccagctgg cgtaatagcg aagaggcccg   8940
caccgatcgc ccttcccaac agttgcgcag cctgaatggc gaatggcgcg acgcgccctg   9000
tagcggcgca ttaagcgcgg cgggtgtggt ggttacgcgc agcgtgaccg ctacacttgc   9060
cagcgcccta gcgcccgctc ctttcgcttt cttcccttcc tttctcgcca cgttcgccgg   9120
ctttccccgt caagctctaa atcgggggct ccctttaggg ttccgattta gtgctttacg   9180
gcacctcgac cccaaaaaac ttgattaggg tgatggttca cgtagtgggc catcgccctg   9240
atagacggtt tttcgccctt tgacgttgga gtccacgttc tttaatagtg gactcttgtt   9300
ccaaactgga acaacactca accctatctc ggtctattct tttgatttat aagggatttt   9360
gccgatttcg gcctattggt taaaaaatga gctgatttaa caaaaattta acgcgaattt   9420
taacaaaata ttaacgttta caatttcc                                      9448
```

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
tcaatgtccc agccatgtat                                         20

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cagcacgatg ccagttgt                                           18

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
atggcctgtg ctttctcaat g                                       21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aggataaaag taggcatgct t                                       21

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cggaatgcct ctgctgttat                                         20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ttcccgaggt ccatctactg                                         20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 9
gctgtcagcc gaggttaaga a                                              21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgaggccgtc catgaagttg                                                20

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgaaagaagt aggagtgggc tt                                             22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atccccattc acactgatga tc                                             22

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctcagtgtag cccaggatgc                                                20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
accaccatgg agaaggctgg                                                20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 15
tgcaggtgat caagaagacg                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tggaagaagg gaaatgttgg                                              20

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
atggagcagg tggctcagtt c                                            21

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
actgccaagc tgcccaaag                                               19

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gggactatcc acctgcaaga                                              20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cctccttggc gtagtagtcg                                              20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
```
aggccagcac ataggagaga                                               20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tttcttgcgc tttcgttttt                                               20

<210> SEQ ID NO 23
<211> LENGTH: 9529
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
caggtggcac ttttcgggga aatgtgcgcg gaacccctat ttgtttattt ttctaaatac    60
attcaaatat gtatccgctc atgagacaat aaccctgata aatgcttcaa taatattgaa   120
aaaggaagag tatgagtatt caacatttcc gtgtcgccct tattcccttt tttgcggcat   180
tttgccttcc tgttttgct caccagaaa cgctggtgaa agtaaaagat gctgaagatc   240
agttgggtgc acgagtgggt tacatcgaac tggatctcaa cagcggtaag atccttgaga   300
gttttcgccc cgaagaacgt tttccaatga tgagcacttt taaagttctg ctatgtggcg   360
cggtattatc ccgtattgac gccgggcaag agcaactcgg tcgccgcata cactattctc   420
agaatgactt ggttgagtac tcaccagtca cagaaaagca tcttacggat ggcatgacag   480
taagagaatt atgcagtgct gccataacca tgagtgataa cactgcggcc aacttacttc   540
tgacaacgat cggaggaccg aaggagctaa ccgcttttt gcacaacatg ggggatcatg   600
taactcgcct tgatcgttgg gaaccggagc tgaatgaagc cataccaaac gacgagcgtg   660
acaccacgat gcctgtagca atggcaacaa cgttgcgcaa actattaact ggcgaactac   720
ttactctagc ttcccggcaa caattaatag actggatgga gcggataaa gttgcaggac   780 cacttctgcg ctcggccctt ccggctggct ggtttattgc tgataaatct ggagccggtg   840
agcgtgggtc tcgcggtatc attgcagcac tggggccaga tggtaagccc tcccgtatcg   900
tagttatcta cacgacgggg agtcaggcaa ctatggatga acgaaataga cagatcgctg   960
agataggtgc ctcactgatt aagcattggt aactgtcaga ccaagtttac tcatatatac  1020
tttagattga tttaaaactt cattttaat ttaaaaggat ctaggtgaag atcctttttg  1080
ataatctcat gaccaaaatc ccttaacgtg agttttcgtt ccactgagcg tcagaccccg  1140
tagaaaagat caaaggatct tcttgagatc ctttttttct gcgcgtaatc tgctgcttgc  1200
aaacaaaaaa accaccgcta ccagcggtgg tttgtttgcc ggatcaagag ctaccaactc  1260
tttttccgaa ggtaactggc ttcagcagag cgcagatacc aaatactgtc cttctagtgt  1320
agccgtagtt aggccaccac ttcaagaact ctgtagcacc gcctacatac ctcgctctgc  1380
taatcctgtt accagtggct gctgccagtg gcgataagtc gtgtcttacc gggttggact  1440
caagacgata gttaccggat aaggcgcagc ggtcgggctg aacggggggt tcgtgcacac  1500
agcccagctt ggagcgaacg acctacaccg aactgagata cctacagcgt gagctatgag  1560

```
aaagcgccac gcttcccgaa gggagaaagg cggacaggta tccggtaagc ggcagggtcg    1620
gaacaggaga gcgcacgagg gagcttccag ggggaaacgc ctggtatctt tatagtcctg    1680
tcgggtttcg ccacctctga cttgagcgtc gattttgtg atgctcgtca ggggggcgga     1740
gcctatggaa aaacgccagc aacgcggcct ttttacggtt cctggccttt tgctggcctt    1800
ttgctcacat gttctttcct gcgttatccc ctgattctgt ggataaccgt attaccgcct    1860
ttgagtgagc tgataccgct cgccgcagcc gaacgaccga gcgcagcgag tcagtgagcg    1920
aggaagcgga agagcgccca atacgcaaac cgcctctccc cgcgcgttgg ccgattcatt    1980
aatgcagctg gcacgacagg tttcccgact ggaaagcggg cagtgagcgc aacgcaatta    2040
atgtgagtta gctcactcat taggcacccc aggctttaca ctttatgctt ccggctcgta    2100
tgttgtgtgg aattgtgagc ggataacaat ttcacacagg aaacagctat gaccatgatt    2160
acgccaagcg cgcaattaac cctcactaaa gggaacaaaa gctggagctg caagcttggc    2220
cattgcatac gttgtatcca tatcataata tgtacattta tattggctca tgtccaacat    2280
taccgccatg ttgacattga ttattgacta gttattaata gtaatcaatt acgggtcat     2340 tagttcatag cccatatatg gagttccgcg ttacataact tacggtaaat ggcccgcctg    2400
gctgaccgcc caacgacccc cgcccattga cgtcaataat gacgtatgtt cccatagtaa    2460
cgccaatagg gactttccat tgacgtcaat gggtggagta tttacggtaa actgcccact    2520
tggcagtaca tcaagtgtat catatgccaa gtacgccccc tattgacgtc aatgacggta    2580
aatggcccgc ctggcattat gcccagtaca tgaccttatg gactttcct acttggcagt     2640 acatctacgt attagtcatc gctattacca tggtgatgcg gttttggcag tacatcaatg    2700
ggcgtggata gcggtttgac tcacggggat ttccaagtct ccaccccatt gacgtcaatg    2760
ggagtttgtt ttggcaccaa aatcaacggg actttccaaa atgtcgtaac aactccgccc    2820
cattgacgca aatgggcggt aggcgtgtac ggtgggaggt ctatataagc agagctcgtt    2880
tagtgaaccg ggtctctct ggttagacca gatctgagcc tgggagctct ctggctaact     2940
agggaaccca ctgcttaagc ctcaataaag cttgccttga gtgcttcaag tagtgtgtgc    3000
ccgtctgttg tgtgactctg gtaactagag atccctcaga ccctttagt cagtgtggaa     3060 aatctctagc agtggcgccc gaacagggac ctgaaagcga aagggaaacc agaggagctc    3120
tctcgacgca ggactcggct tgctgaagcg cgcacggcaa gaggcgaggg gcggcgactg    3180
gtgagtacgc caaaaatttt gactagcgga ggctagaagg agagagatgg gtgcgagagc    3240
gtcagtatta gcggggggag aattagatcg cgatgggaaa aaattcggtt aaggccaggg    3300
ggaaagaaaa aatataaatt aaaacatata gtatgggcaa gcagggagct agaacgattc    3360
gcagttaatc ctggcctgtt agaaacatca gaaggctgta gacaaatact gggacagcta    3420
caaccatccc ttcagacagg atcagaagaa cttagatcat tatataatac agtagcaacc    3480
ctctattgtg tgcatcaaag gatagagata aaagacacca aggaagcttt agacaagata    3540
gaggaagagc aaaacaaaag taagaccacc gcacagcaag cggccgctga tcttcagacc    3600
tggaggagga gatatgaggg acaattggag aagtgaatta tataaatata agtagtaaa     3660 aattgaacca ttaggagtag cacccaccaa ggcaaagaga agagtggtgc agagagaaaa    3720
aagagcagtg ggaataggag ctttgttcct tgggttcttg ggagcagcag gaagcactat    3780
gggcgcagcc tcaatgacgc tgacggtaca ggccagacaa ttattgtctg gtatagtgca    3840
gcagcagaac aatttgctga gggctattga ggcgcaacag catctgttgc aactcacagt    3900
ctggggcatc aagcagctcc aggcaagaat cctggctgtg gaaagatacc taaaggatca    3960
```

```
acagctcctg gggatttggg gttgctctgg aaaactcatt tgcaccactg ctgtgccttg    4020
gaatgctagt tggagtaata aatctctgga acagattgga atcacacgac ctggatggag    4080
tgggacagag aaattaacaa ttacacaagc ttaatacact ccttaattga agaatcgcaa    4140
aaccagcaag aaaagaatga acaagaatta ttggaattag ataaatgggc aagtttgtgg    4200
aattggttta acataacaaa ttggctgtgg tatataaaat tattcataat gatagtagga    4260
ggcttggtag gtttaagaat agttttttgct gtactttcta tagtgaatag agttaggcag    4320
ggatattcac cattatcgtt tcagacccac ctcccaaccc cgaggggacc cgacaggccc    4380
gaaggaatag aagaagaagg tggagagaga cacagagaca gatccattcg attagtgaac    4440
ggatctcgac ggtatcgatc tcgacacaaa tggcagtatt catccacaat tttaaaagaa    4500 aagggggat tgggggtac agtgcagggg aaagaatagt agacataata gcaacagaca    4560
tacaaactaa agaattacaa aaacaaatta caaaaattca aaattttcgg gtttattaca    4620
gggacagcag agatccagtt tgggtcgagg atatcggatc ggaattaatt catcgatcga    4680
ttagtccaat ttgttaaaga caggatatca gtggtccagg ctctagtttt gactcaacaa    4740
tatcaccagc tgaagcctat agagtacgag ccatagatag aataaaagat tttatttagt    4800
ctccagaaaa agggggaat gaaagacccc acctgtaggt ttggcaagct aggatcaagg    4860
ttaggaacag agagacagca gaatatgggc caaacaggat atctgtggta agcagttcct    4920 gcccggctc agggccaaga acagttggaa cagcagaata tgggccaaac aggatatctg    4980
tggtaagcag ttcctgcccc ggctcagggc caagaacaga tggtcccag atgcggtccc    5040 gccctcagca gtttctagag aaccatcaga tgtttccagg gtgccccaag acctgaaat    5100 gaccctgtgc cttatttgaa ctaaccaatc agttcgcttc tcgcttctgt tcgcgcgctt    5160
ctgctccccg agctcaataa aagagcccac aacccctcac tcggcgcgat ctagatctcg    5220
agctcgaatt cgcccttcct gagatcaccg gtaggagggc catcatgaac tttctgctgt    5280
cttgggtgca ttggagcctt gccttgctgc tctacctcca ccatgccaag tggtcccagg    5340
ctgcacccat ggcagaagga ggagggcaga atcatcacga agtggtgaag ttcatggatg    5400
tctatcagcg cagctactgc catccaatcg agaccctggt ggacatcttc caggagtacc    5460
ctgatgagat cgagtacatc ttcaagccat cctgtgtgcc cctgatgcga tgcgggggct    5520
gctgcaatga cgagggcctg gagtgtgtgc ccactgagga gtccaacatc accatgcaga    5580
ttatgcggat caaacctcac caaggccagc acataggaga gatgagcttc ctacagcaca    5640
acaaatgtga atgcagacca agaaagata gagcaagaca agaaaatccc tgtgggcctt    5700
gctcagagcg gagaaagcat ttgttttgtac aagatccgca gacgtgtaaa tgttcctgca    5760
aaaacacaga ctcgcgttgc aaggcgaggc agcttgagtt aaacgaacgt acttgcagat    5820
gtgacaagcc gaggcggtga aagggcgaat ctaccgggt aggggaggcg cttttcccaa    5880
ggcagtctgg agcatgcgct ttagcagccc cgctggcact tggcgctaca caagtggcct    5940
ctggcctcgc acacattcca catccaccgg taggcgccaa ccggctccgt tctttggtgg    6000
ccccttcgcg ccaccttcta ctcctcccct agtcaggaag ttcccccccg cccgcagct    6060 cgcgtcgtga aggacgtgac aaatggaagt agcacgtctc actagtctcg tgcagatgga    6120
cagcaccgct gagcaatgga agcgggtagg ccttggggc agcggccaat agcagctttg    6180
ctccttcgct ttctgggctc agaggctggg aaggggtggg tccggggcg ggctcagggg    6240 cgggctcagg ggcggggcgg gcgcccgaag gtcctccgga ggcccggcat tctcgcacgc    6300
```

```
ttcaaaagcg cacgtctgcc gcgctgttct cctcttcctc atctccgggc ctttcgacca    6360
tctagatcag gatccctcga gcccctcgc gaccatggct tcgtaccccg gccatcaaca     6420
cgcgtctgcg ttcgaccagg ctgcgcgttc tcgcggccat agcaaccgac gtacggcgtt    6480
gcgccctcgc cggcagcaag aagccacgga agtccgcccg gagcagaaaa tgcccacgct    6540
actgcgggtt tatatagacg gtccccacgg gatggggaaa accaccacca cgcaactgct    6600
ggtggccctg ggttcgcgcg acgatatcgt ctacgtaccc gagccgatga cttactggcg    6660
ggtgctgggg gcttccgaga caatcgcgaa catctacacc acacaacacc gcctcgacca    6720
gggtgagata tcggccgggg acgcggcggt ggtaatgaca agcgcccaga taacaatggg    6780
catgccttat gccgtgaccg acgccgttct ggctcctcat atcgggggg aggctgggag     6840 ctcacatgcc ccgcccccgg ccctcaccct catcttcgac cgccatccca tcgccgccct    6900
cctgtgctac ccggccgcgc gatacctttat gggcagcatg accccccagg ccgtgctggc   6960
gttcgtggcc ctcatcccgc cgaccttgcc cggcacaaac atcgtgttgg gggcccttcc    7020
ggaggacaga cacatcgacc gcctggccaa acgccagcgc cccggcgagc ggcttgacct    7080
ggctatgctg gccgcgattc gccgcgttta cgggctgctt gccaatacgg tgcggtatct    7140
gcagggcggc ggtcgtggc gggaggattg gggacagctt tcggggacgg ccgtgccgcc     7200
ccagggtgcc gagccccaga gcaacgcggg cccacgaccc catatcgggg acacgttatt    7260
taccctgttt cgggcccccg agttgctggc ccccaacggc gacctgtata acgtgtttgc    7320
ctgggccttg gacgtcttgg ccaaacgcct ccgtcccatg cacgtctttta tcctggatta   7380 cgaccaatcg cccgccggct gccgggacgc cctgctgcaa cttacctccg ggatggtcca    7440
gacccacgtc accaccccg gctccatacc gacgatatgc gacctggcgc gcacgtttgc     7500
ccgggagatg gggaggcta actgacttaa gcttggtacc gagctcggat ccagggggggc    7560 tagcgataat caacctctgg attacaaat ttgtgaaaga ttgactggta ttcttaacta     7620
tgttgctcct tttacgctat gtggatacgc tgctttaatg cctttgtatc atgctattgc    7680
ttcccgtatg gctttcattt tctcctcctt gtataaatcc tggttgctgt ctctttatga    7740
ggagttgtgg cccgttgtca ggcaacgtgg cgtggtgtgc actgtgtttg ctgacgcaac    7800
ccccactggt tggggcattg ccaccacctg tcagctcctt tccgggactt tcgctttccc    7860 cctcccctatt gccacggcgg aactcatcgc cgcctgcctt gcccgctgct ggacaggggc   7920
tcggctgttg ggcactgaca attccgtggt gttgtcgggg aaatcatcgt cctttccttg    7980
gctgctcgcc tgtgttgcca cctggattct gcgcgggacg tccttctgct acgtcccttc    8040
ggccctcaat ccagcggacc ttccttcccg cggcctgctg ccggctctgc ggcctcttcc    8100
gcgtcttcgc cttcgccctc agacgagtcg gatctccctt tgggccgcct ccccgcatcg    8160
ctagccaatt cgagctcggt acctttaaga ccaatgactt acaaggcagc tgtagatctt    8220
agccactttt taaagaaaa ggggggactg aagggctaa ttcactccca acgaagacaa      8280
gatctgcttt ttgcttgtac tgggtctctc tggttagacc agatctgagc ctgggagctc    8340
tctggctaac tagggaaccc actgcttaag cctcaataaa gcttgccttg agtgcttcaa    8400
gtagtgtgtg cccgtctgtt gtgtgactct ggtaactaga gatccctcag accctttag    8460 tcagtgtgga aaatctctag cagtagtagt tcatgtcatc ttattattca gtatttataa    8520
cttgcaaaga aatgaatatc agagagtgag aggaacttgt ttattgcagc ttataatggt   8580
tacaaataaa gcaatagcat cacaaatttc acaaataaag catttttttc actgcattct    8640
agttgtggtt tgtccaaact catcaatgta tcttatcatg tctggctcta gctatcccgc    8700
```

```
ccctaactcc gcccatcccg cccctaactc cgcccagttc cgcccattct ccgcccatg     8760 gctgactaat tttttttatt tatgcagagg ccgaggccgc ctcggcctct gagctattcc   8820
agaagtagtg aggaggcttt tttggaggcc taggcttttg cgtcgagacg tacccaattc   8880
gccctatagt gagtcgtatt acgcgcgctc actggccgtc gttttacaac gtcgtgactg   8940
ggaaaaccct ggcgttaccc aacttaatcg ccttgcagca catccccctt tcgccagctg   9000
gcgtaatagc gaagaggccc gcaccgatcg cccttcccaa cagttgcgca gcctgaatgg   9060
cgaatggcgc gacgcgccct gtagcggcgc attaagcgcg gcgggtgtgg tggttacgcg   9120
cagcgtgacc gctacacttg ccagcgccct agcgcccgct cctttcgctt tcttcccttc   9180
ctttctcgcc acgttcgccg gctttccccg tcaagctcta atcgggggc tccctttagg    9240 gttccgattt agtgctttac ggcacctcga ccccaaaaaa cttgattagg gtgatggttc   9300
acgtagtggg ccatcgccct gatagacggt ttttcgccct ttgacgttgg agtccacgtt   9360
ctttaatagt ggactcttgt tccaaactgg aacaacactc aaccctatct cggtctattc   9420
ttttgattta tagggatttt tgccgatttc ggcctattgg ttaaaaaatg agctgattta   9480
acaaaaattt aacgcgaatt ttaacaaaat attaacgttt acaatttcc                9529
```

GENETICALLY MODIFIED MSC AND THERAPEUTIC METHODS

CROSS-REFERENCE TO RELATED APPLICATIONS

This application is a continuation of U.S. application Ser. No. 15/351,415, filed Nov. 14, 2016, now abandoned, which is a continuation of U.S. application Ser. No. 13/844,138, filed Mar. 15, 2013, now abandoned, which is a continuation-in-part of International Application No. PCT/US2012/053537, filed Aug. 31, 2012, the contents of both each of which are incorporated by reference in their entirety into the present application.

The instant application contains a Sequence Listing which has been submitted electronically in ASCII format and is hereby incorporated by reference in its entirety. Said ASCII copy, created on May 29, 2019, is named 060933-1203.txt and is 30,981 bytes in size.

BACKGROUND

Critical limb ischemia (CLI) is characterized by severe obstruction of blood flow to the feet or legs which can result in limb loss if left untreated. The symptoms associated with this very severe form of lower extremity peripheral artery disease (PAD) are pain in the foot at rest, non-healing ulcers, limb/digital gangrene and delayed wound healing. It is estimated that 160,000-180,000 major and minor amputations are performed annually in the United States due to CLI. The rate of lower limb amputation in the United States has doubled since 1985 with a 4- to 5-fold increase in those over the age of 80. Fewer than half of all CLI patients achieve full mobility after an amputation and only one in four above-the-knee amputees will ever wear a prosthesis. The diagnosis comes at a substantial price to the society as the estimated cost of treating CLI is 10 to 20 billion dollars per year in the US alone.

The quality of life for those with CLI is extremely poor and reported to be similar to that of patients with end stage malignancy. Most patients with CLI will undergo repeat hospitalizations and surgical/endovascular procedures in an effort to preserve the limb. Unfortunately, the limb salvage efforts are often not effective enough to reverse ischemia, and despite multiple attempts at revascularization, the wounds still fail to heal. In addition, many patients are not candidates for traditional forms of revascularization due to occluded or diffusely diseased distal vessels or lack of suitable bypass conduit. CLI represents a significant unmet medical need since there are currently no effective pharmaceuticals or biologic therapies for treatment of these no-option patients. Accordingly, there is a need in the art for therapies that promote angiogenesis and salvage critically ischemic limbs.

SUMMARY

This disclosure relates to vectors, isolated cells, compositions, and methods for the treatment of peripheral artery disease (PAD), such as critical limb ischemia and associated disorders. One aspect of the disclosure relates to a vector comprising or alternatively consisting essentially of, or yet further consisting of a nucleic acid encoding a 165A isoform VEGF protein or an equivalent thereof and a promoter that regulates expression of the nucleic acid encoding the 165A isoform VEGF or an equivalent thereof. In a further aspect, the vector further comprises, or alternatively further consists essentially of, or yet further consists of, an enhancer element. In a yet further aspect, the promoter is an inducible promoter or alternatively, a constitutive promoter. Non-limiting examples of promoters include a MDNU3 constitutive promoter, a tetracycline inducible promoter, or an inducible promoter that is induced by a molecule of the group tetracycline, doxycycline or anhydrotetracycline.

In a further aspect, the vector as described above further comprises, or alternatively consists essentially of, or yet further consists of, a nucleic acid encoding a tetracycline activator protein and a promoter that regulates expression of the tetracycline activator protein. In one aspect, the promoter that regulates expression of the tetracycline activator protein is a constitutive promoter, e.g., a phosphoglycerate kinase promoter (PGK).

In a yet further aspect, the vector as described above further comprises, or alternatively consists essentially of, or yet further consists of a suicide gene and a promoter that regulates expression of the suicide gene.

In addition, in the vector as described above, the nucleic acid encoding the tetracycline activator protein and the suicide gene are regulated by one promoter.

In another aspect of the above described vectors, the vectors further comprise, or alternatively consist essentially of, or yet further consist of, a protease cleavage site located between the suicide gene and the nucleic acid encoding the tetracycline activator protein. A non-limiting example of a protease cleavage site is a 2A protease cleavage site. A non-limiting example of a suicide gene contained within the vectors as described above include a thymidine kinase (TK) gene. The TK gene can be wild-type (WT) or a mutated form. These are known in the art.

The nucleic acid encoding 165A isoform VEGF or an equivalent thereof can comprise, or alternatively consist essentially of, or yet further consist of, the polynucleotide of SEQ ID NO: 1, or a biological equivalent thereof. An example of a biological equivalent of VEGF nucleic acid comprises a nucleic acid that hybridizes under conditions of high stringency to the complement of SEQ ID NO: 1 and encodes a protein having VEGF biological activity. Another example includes a nucleic acid having at least 80% sequence identity to SEQ ID NO: 1 or its complement and encodes a protein having VEGF biological activity.

As noted for the above vectors, the vector portion of the construct can be any suitable vector, e.g., a plasmid or a viral vector that is selected from the group of a lentiviral vector, retroviral vector, adenovirus vector, adeno-associated virus vector, or alphavirus vector.

In another embodiment, this disclosure provides a vector comprising, or alternatively consisting essentially of, or yet further consisting of, the following operatively linked to each other: a promoter, a nucleic acid encoding a 165A isoform VEGF protein or an equivalent thereof, a promoter and a TK gene. The TK gene can be wild-type (WT) or a mutated form. The vector may further comprise, or alternatively consist essentially of, or yet further consist of, a 5' LTR and a 3'LTR. In one aspect, either or both promoters are the same or different and are constitutive or inducible promoters examples of which are provided herein. In another aspect, the 5'LTR and 3'LTR are provided in a pCCLc plasmid.

In another embodiment, this disclosure provides a vector comprising, or alternatively consisting essentially of, or yet further consisting of, the following operatively linked to each other: a 5'LTR, a MNDU3 promoter, a nucleic acid encoding a 165A isoform VEGF protein or an equivalent thereof, a phosphoglycerate kinase 1 (PGK) constitutive promoter, a TK gene, an enhancer, and a 3' LTR. The TK gene can be wild-type (WT) or a mutated form. In a further aspect, the enhancer comprises a WPRE enhancer. In another aspect, the 5'LTR and 3'LTR are provided in a pCCLc plasmid.

In a particular aspect, the vector comprise, or alternatively consists essentially of yet further consists of, a polynucleotide that in turn comprises, or alternatively consists essentially of yet further consists of a nucleic acid of the sequence of SEQ ID NO: 2 or 23, or an equivalent of each thereof of nucleotides 4654 to 8071 of SEQ ID NO: 2, or an equivalent thereof of nucleotides 4667 to 8160 of SEQ ID NO: 23. SEQ ID NOS. 2 and 23 contain the sequence of WT TK gene (nucleotides 6941 to 8071 of SEQ ID NO: 2). Example of a biological equivalent polynucleotide(s) include a nucleic acids that hybridizes under conditions of high stringency to the complement of SEQ ID NO: 2, 23, nucleotides 4654 to 8071 of SEQ ID NO: 2, or nucleotides 4667 to 8160 of SEQ ID NO: 23, and that encodes a protein having VEGF biological activity. Another example includes a nucleic acid having at least 80% sequence identity to SEQ ID NO: 2, 23, nucleotides 4654 to 8071 of SEQ ID NO: 2, or nucleotides 4667 to 8160 of SEQ ID NO: 23, or their respective complements and encodes a protein having VEGF biological activity.

Further aspects relate to a viral packaging system comprising or alternatively consisting essentially of, or yet further consisting of a vector described herein, a packaging plasmid, and an envelope plasmid. Also provided are pseudotyped viral particles produced by transducing a packaging cell line with a viral packaging system as described herein under conditions suitable to package the viral vector. In a further aspect, the pseudotyped viral particles are isolated from the supernatant.

Yet further aspects relate to isolated cells comprising or alternatively consisting essentially of, or yet further consisting of a nucleic acid encoding a 165A isoform VEGF protein, or an equivalent thereof (as described above) and a promoter that regulates expression of the nucleic acid encoding the VEGF 165A isoform protein or an equivalent thereof (as described above). In one aspect the cells are marrow stromal cells.

Method aspects of the disclosure relate to methods for treating critical limb ischemia in a patient in need thereof, the method comprising or alternatively consisting essentially of, or yet further consisting of administering an isolated cell to the patient as described herein.

A second method aspect relates to a method for promoting wound healing, promoting or increasing the rate of angiogenesis or wound healing, decreasing the size of a wound, or decreasing the time to wound healing in a patient in need thereof, the method comprising or alternatively consisting essentially of, or yet further consisting of administering an isolated ell described herein to the patient.

A further method aspect relates to a method for salvaging a limb in a patient with critical limb ischemia, the method comprising or alternatively consisting essentially of, or yet further consisting of administering an isolated cell described herein to the patient.

A yet further method aspect relates to a method for increasing vascularization in a patient in need thereof, the method comprising or alternatively consisting essentially of, or yet further consisting of administering an isolated cell described herein to the patient.

Also provided are isolated cells, e.g., stem cells such as mesenchymal stem cells expressing the phenotype CD34−/CD45−/CD105+/CD90+/CD73+ and comprising a 165A VEGF polynucleotide or protein, an isoform or an equivalent thereof. Further aspects relate to expanded populations of the described isolated cells, e.g., stem cells such as mesenchymal stem cells and compositions comprising the isolated cells as described herein.

Scale bar=200 mm. (B) Unilateral hind limb ischemia was induced in NOD/SCID/β-2-microglobulin-deficient mice followed by transplantation of control (open circles, n=8) or VEGF over-expressing MSCs (n=6, solid circles) (Right Panel). Laser Doppler perfusion imaging was used to assess the ratio blood flow in the healthy versus affected legs. Mean group values±SD are shown. Asterisks denote significant difference (p≤0.05) (Left Panel).

Figure 7:
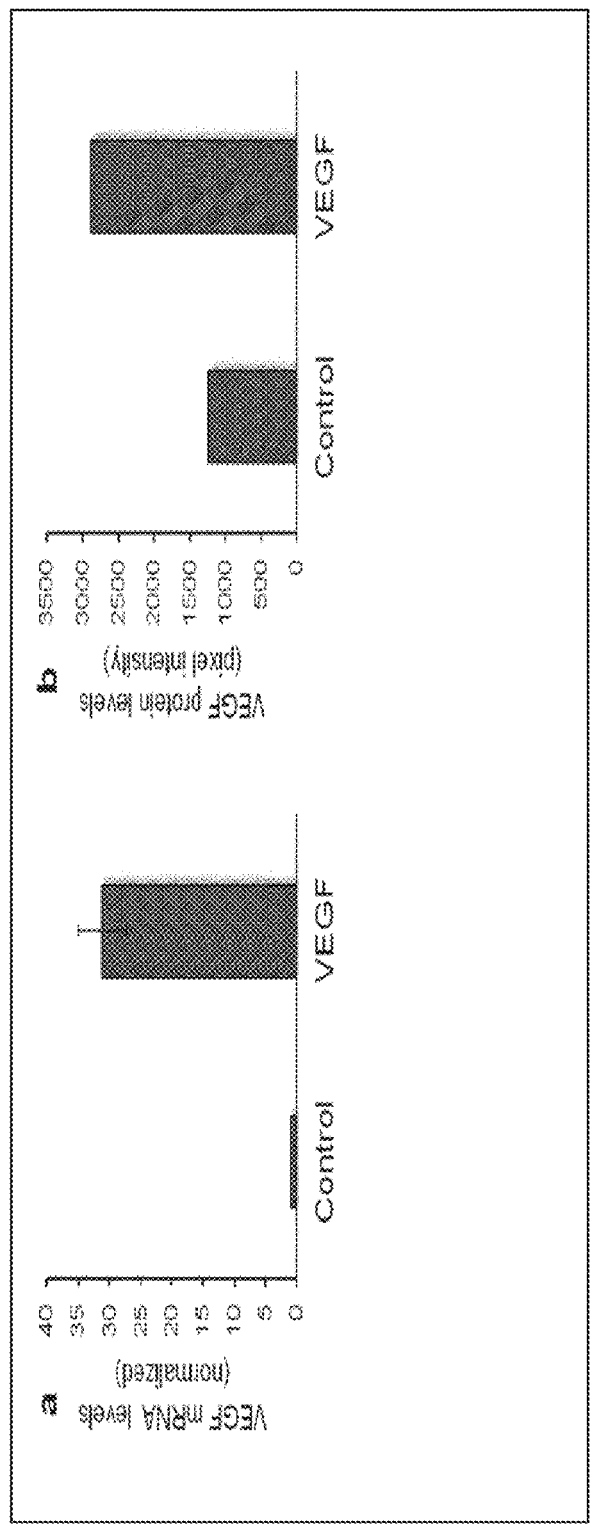

FIG. 7 shows the VEGF mRNA (FIG. 7A) and protein (FIG. 7B) levels in MSC cells transduced with the viral vector as described in Example 2.

Figure 8:
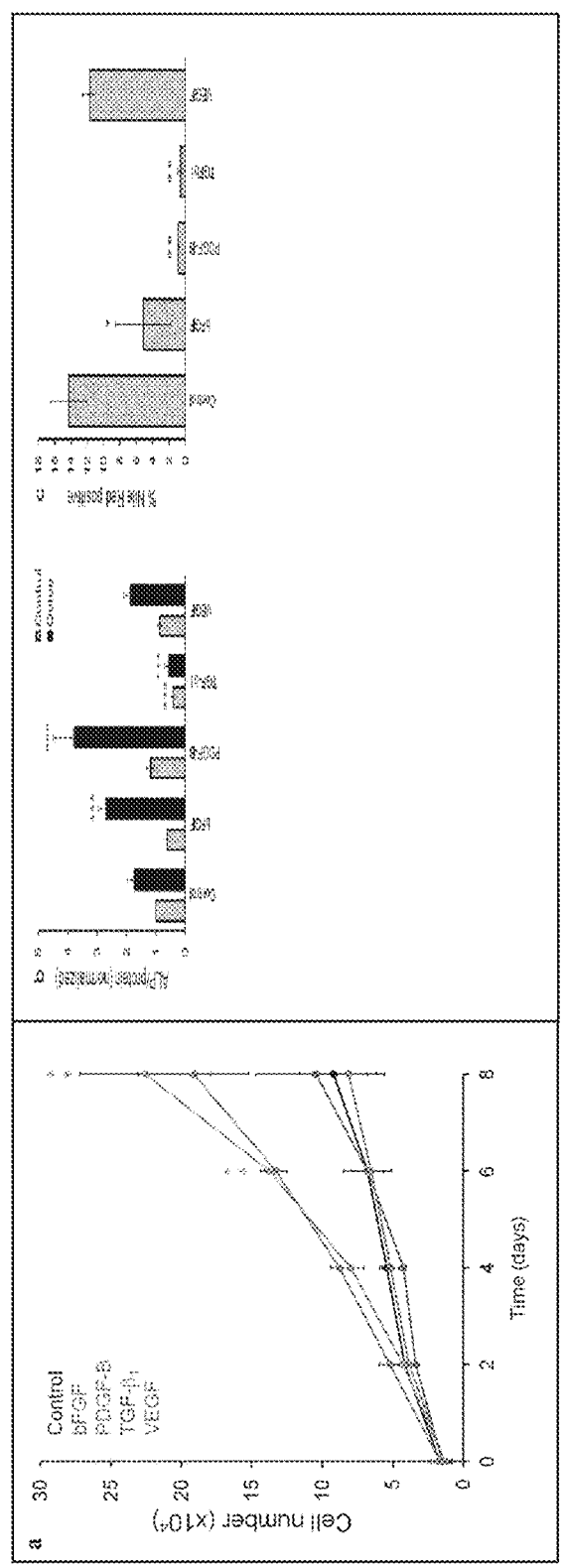

FIG. 8 demonstrates that engineering MSCs to produce VEGF does not affect their proliferation rate or differentiative capacity, in established MSC potency assays. A) Proliferation of MSC over-expressing GF was measured by counting cells using trypan blue exclusion dye in a hemocytometer, as described (n=3). B) Osteogenic and C) adipogenic differentiation performed with MSC over-expressing different growth factors show that in contrast to effects exerted by over-expression of bFGF, PDGF-BB or TGF-$β_1$, while over-expression of VEGF-$A_{165}$ did not show any significant effects on differentiation, as compared to MSC transduced with the control lentiviral vector.

Figure 9:
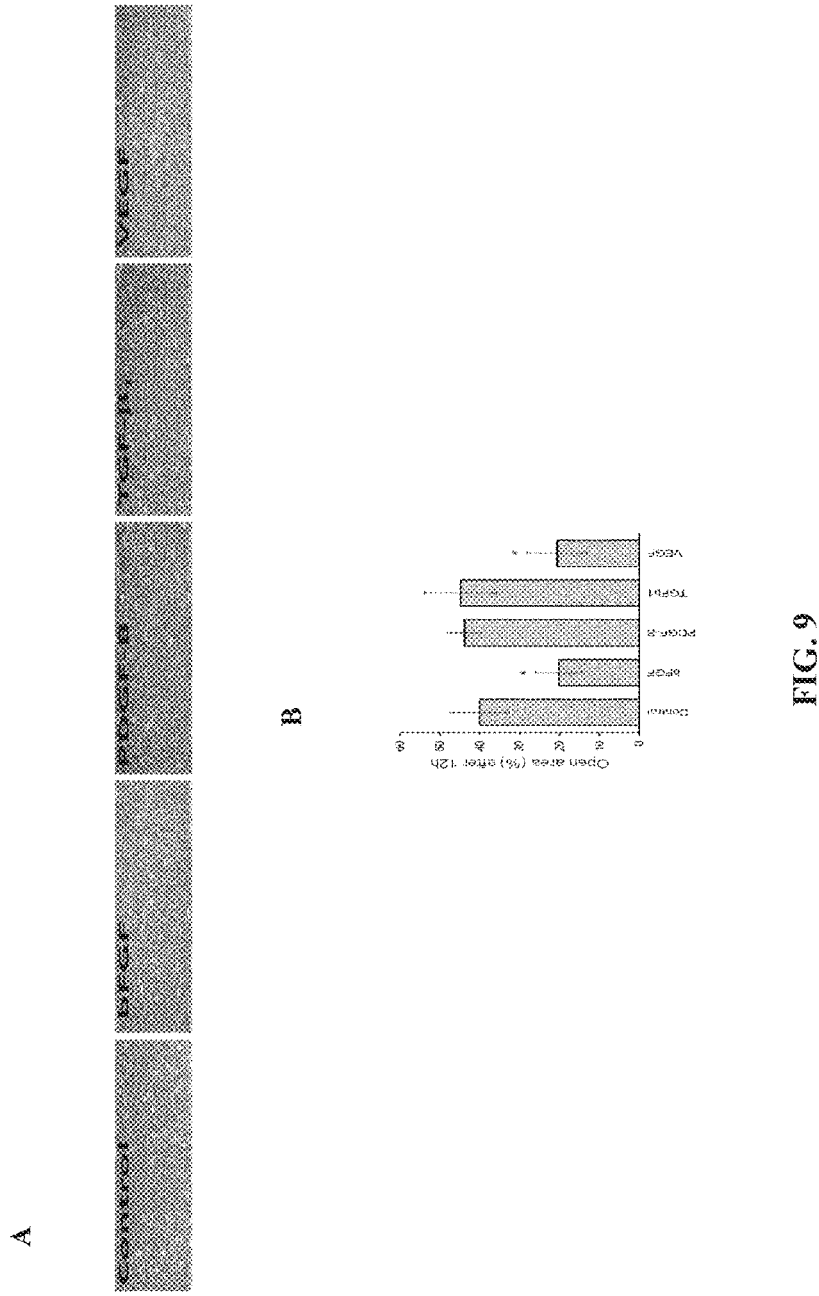

FIG. 9 shows a wound healing assay which was used to assess the effect of conditioned media from MSC over-expressing GF, on the migration of HUVEC. Both representative pictures (9A) (phase contrast, upper panels) and quantification (9B) (right, n=4) were acquired after 12 h. Scale bar=200 mm.

Figure 10:
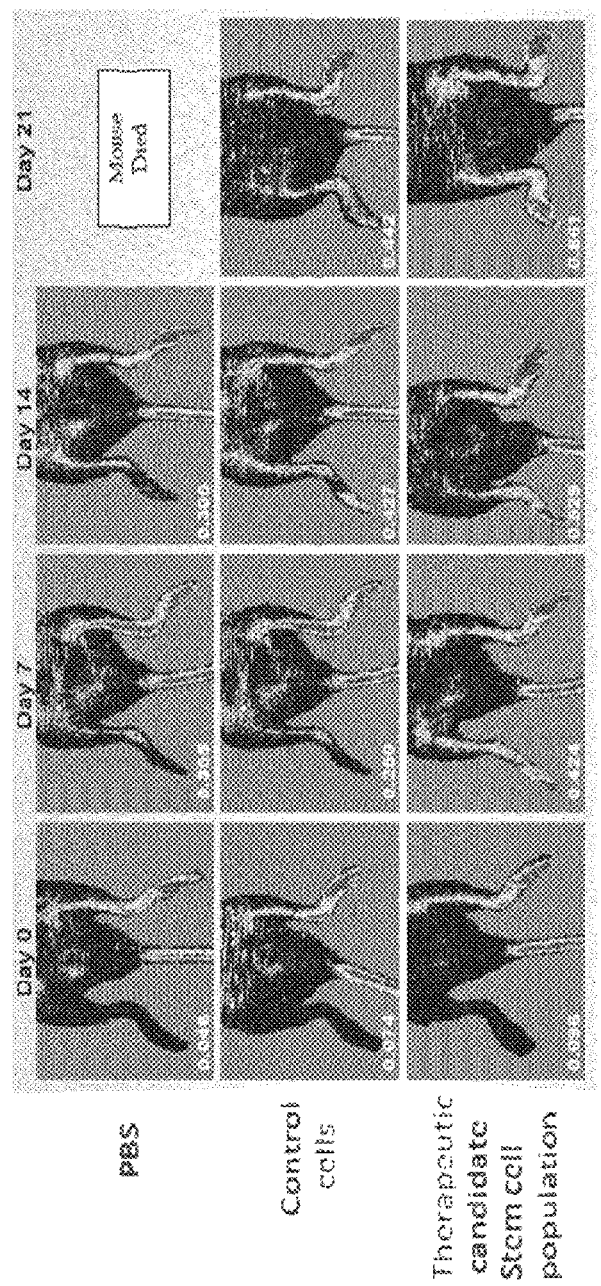

FIG. 10 depicts a HLI model measured by laser Doppler Imaging of blood flow. Contralateral leg provides an internal control. A ratio of 1.0 indicates that bloodflow is equivalent between both hindlimbs. Lower ratios=diminished bloodflow in the injured limb. The development candidate MSC/VEGF (final ratio 0.861) promoted almost complete correction by day 21, in contrast to the PBS and control cell populations, which did not significantly restore bloodflow.

Figure 11:
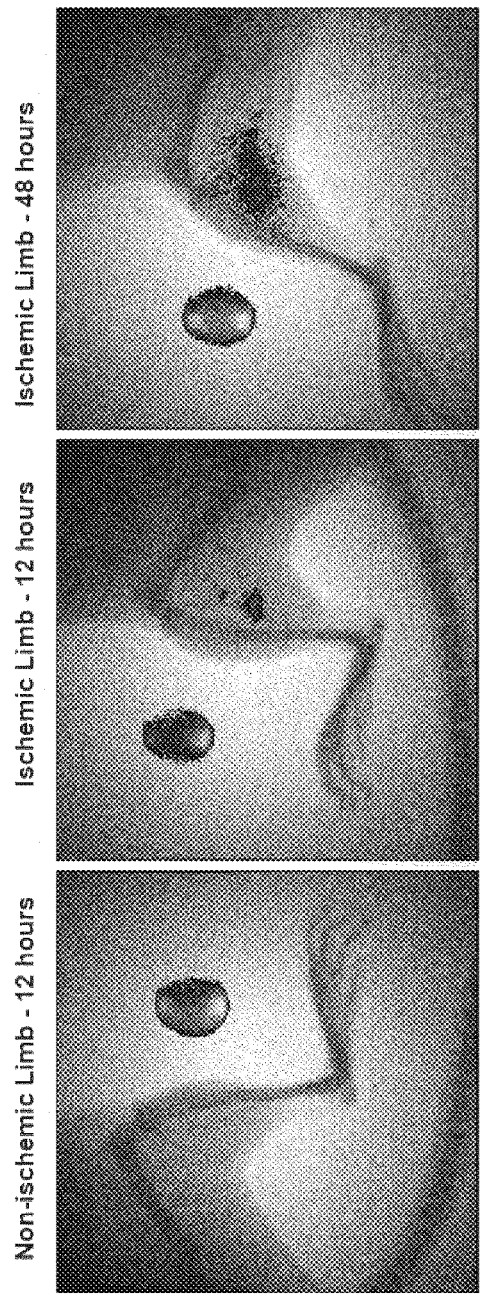

FIG. 11 (3 panels) demonstrates that iron nanoparticle-loaded human stem cells are recruited to the site of ischemic injury within 12 hr after tailvein injection, and have dramatically accrued to the hypoxic tissue by 48 hours (peak). IV injection of $5 \times 10^5$ labeled human stem cells at T=0 hrs. Imaging done at 0, 12 and 48 hrs. (Capoccia et al 2009).

Figure 12:
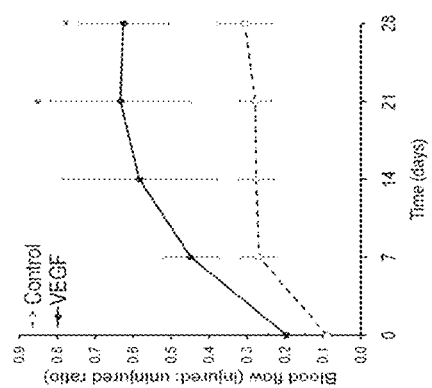

FIG. 12 shows that MSC/VEGF promotes vascular repair in vivo. Unilateral hind limb ischemia was induced in NOD/SCID/β-2-microglobulin-deficient mice followed by transplantation of control MSC (open circles, n=8) or MSC/VEGF (n=6, solid circles). Laser Doppler perfusion imaging was used to assess the ratio blood flow in the healthy versus affected legs. Mean group values±SD are shown. Asterisks denote significant difference (p≤0.05).

Figure 13:
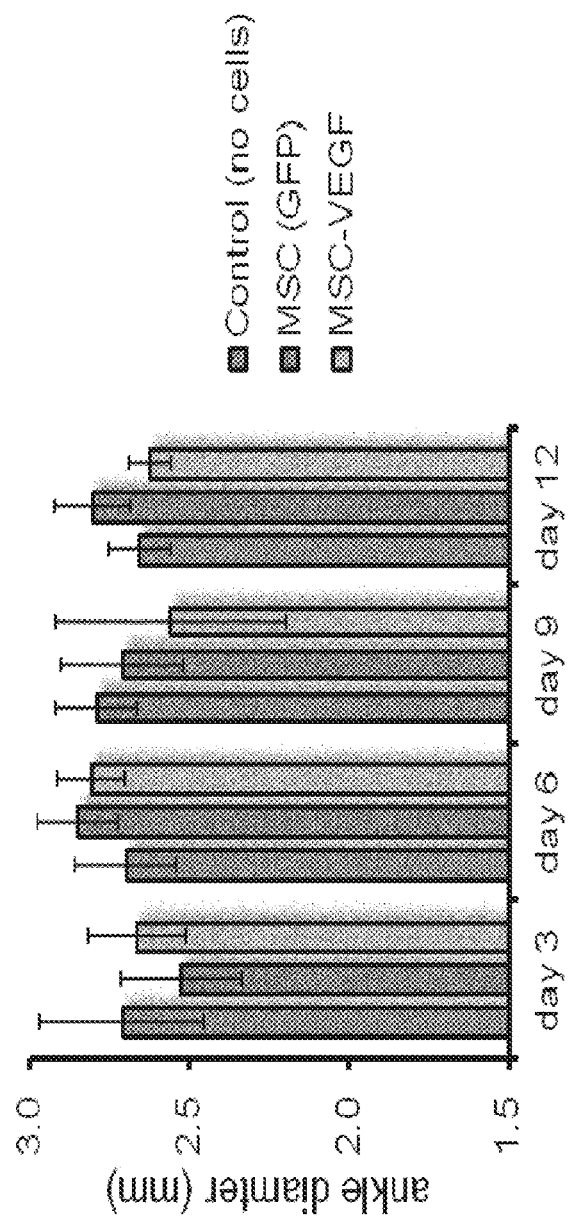

FIG. 13 shows that no edema is caused by MSC/VEGF. Hindlimb ischemia was induced in NSG mice (N=15). The day after removal of the femoral artery, 12 ul of carrier HyStem C gel with 100,000 Control MSC (N=5) or 100,000 MSC/VEGF (N=5) was injected in the left quadriceps muscle, near the site of excision. HyStem C carrier without cells was used as the control (N=5). Ankle diameter was measured on the injected leg on days 3, 6, 9, and 12 using calipers. No significant difference was observed between the three groups.

Figure 14:
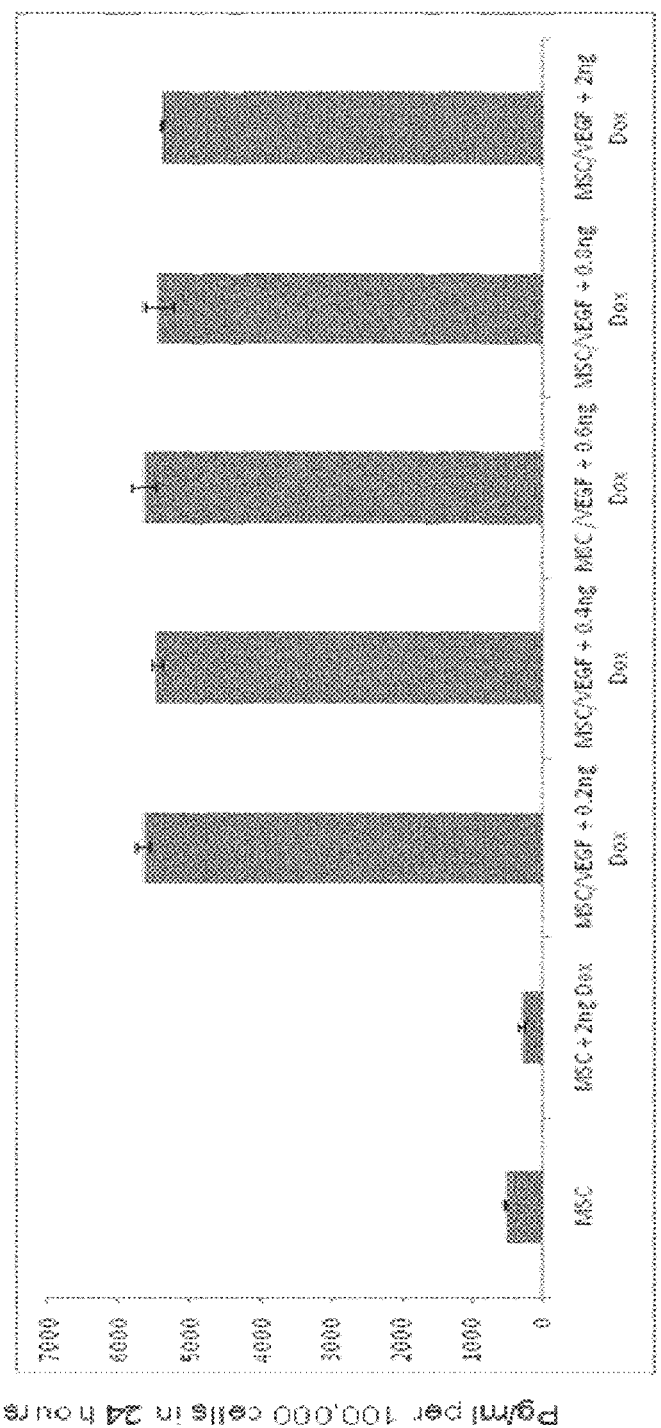

FIG. 14 shows an ELISA which was used to measure VEGF expression from MSC/VEGF after induction with different levels of doxycycline. VEGF production was above 5000 pg/ml per 100,000 cells at all dox levels tested (50 ng per one million cells in 24 hours).

Figure 15:
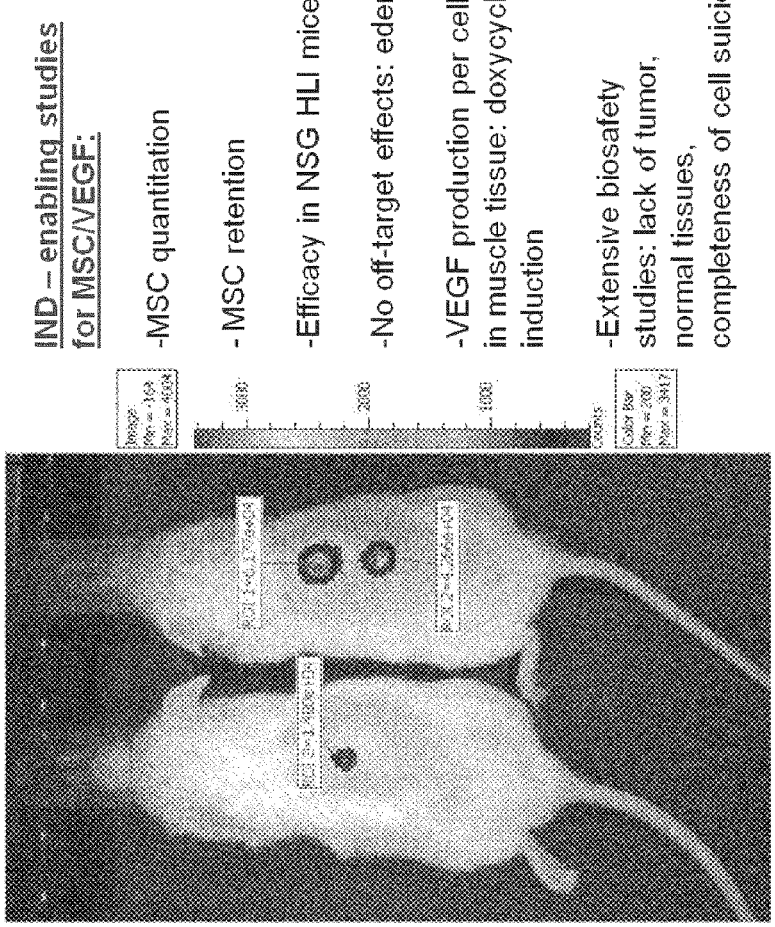

FIG. 15 shows IND-enabling studies to be completed at the level of GLP using the MSC/VEGF test lot. In the figure shown, MSCs engineered to express luciferase were evaluated for the duration of retention, and injected at increasing doses. The scale shows correlation of signal to cell number to evaluate expression and induction of the vector promoter by doxycycline. VEGF expression will be evaluated on a per-cell basis following injection.

Figure 16:
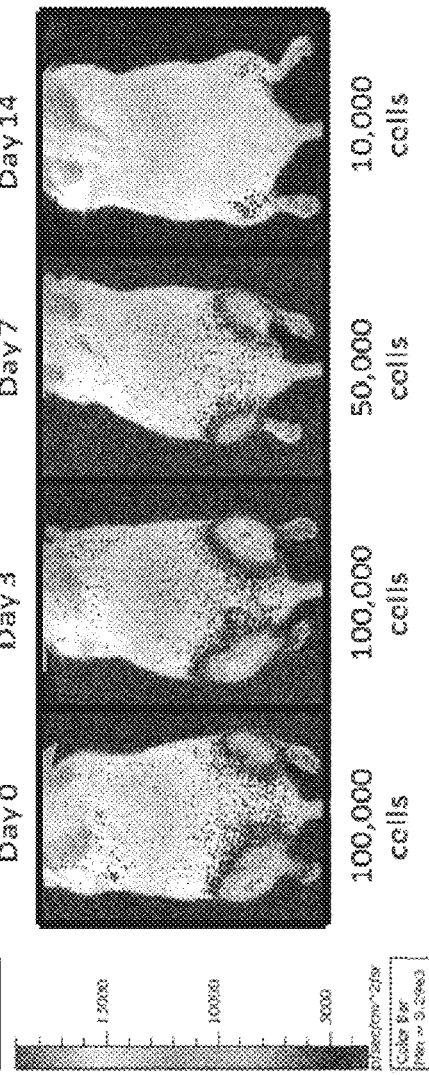

FIG. 16 exemplifies a product retention study. MSC/VEGF cells were engineered to produce luciferase for imaging uses only. 100,000 cells per flank were injected and imaged over time. Mice were evaluated for the duration of retention. The study shows retention of at least 50% of the cells for the first week, but a log drop in cell number by day 14.

Figure 17A:
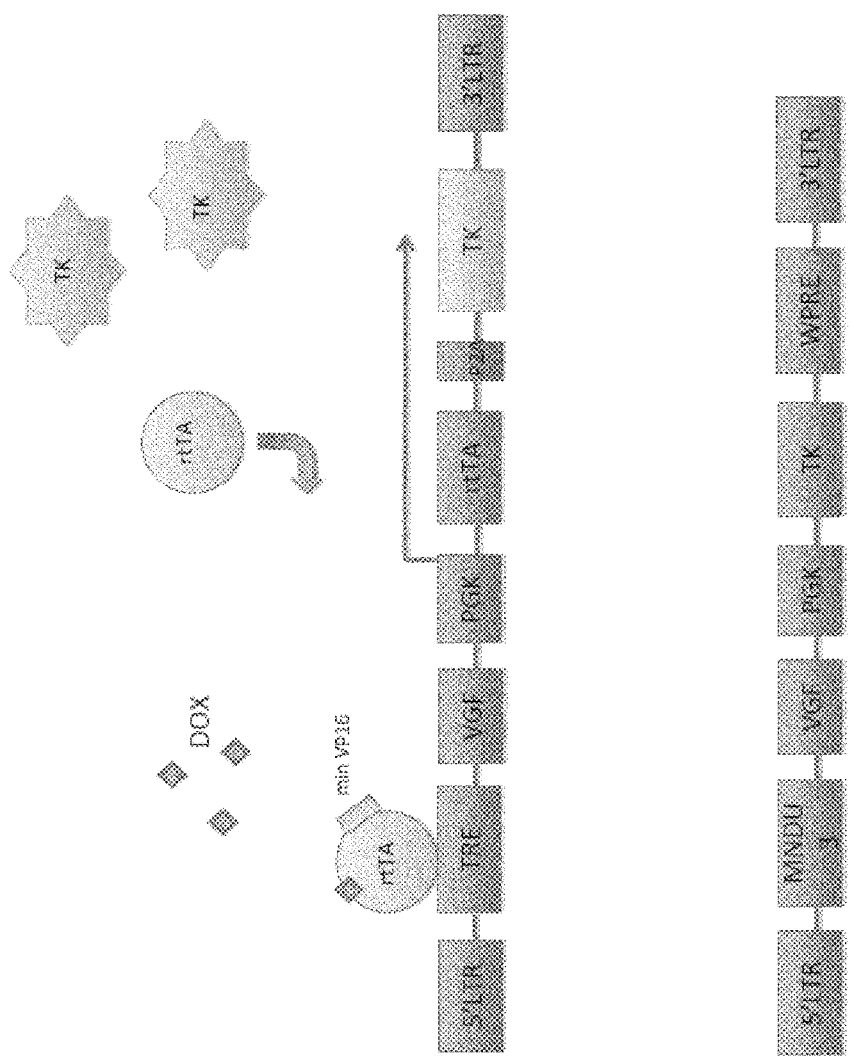
Figure 17B:

FIG. 17A (top and bottom panels) depicts the pCCLc-TRE-VEGF-PGK-rtTA-P2A-TK lentiviral vector. VEGF expression is under control of the tet-responsive promoter, so that the growth factor will only be produced from MSC in the recipient while they take doxycycline tablets (Month 1). The vector also encodes the well-characterized "suicide gene" TK, for additional biosafety. This gene allows eradication of all transduced cells if the antiviral ganciclovir is administered. FIG. 17B depicts the sequence of the pCCLc-MNDU3-VEGF-PGK-TK plasmid vector.

Figure 18:
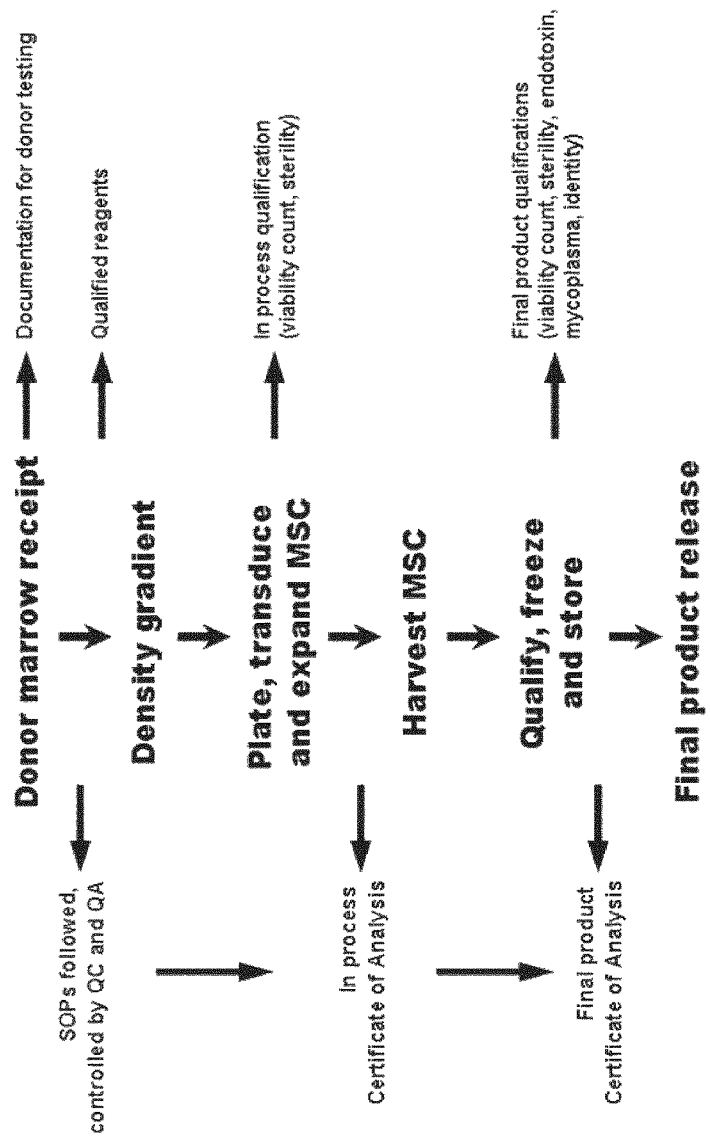

FIG. 18 provides an overview of the MSC/VEGF process. Highly tested mesenchymal stem cells (MSCs) are engineered to secrete vascular endothelial growth factor (VEGF). Marrow obtained from a qualified donor (Lonza) is plated and cultured under Good Manufacturing Practice (GMP) conditions following well-established Standard Operating Procedure (SOP) for MSC expansion at UC Davis. At the first passage, approximately 10% of the cells are split off to expand as the non-transduced cell lot (MSC lot). At the first passage, approximately 10% of the cells are split off to expand as the non-transduced cell lot (MSC lot). The remainder of the cells are exposed to the lentiviral vector at a multiplicity of infection of approximately 20 (dependent on titer of the GMP vector lot), to generate the MSC/VEGF lot. This allows for insertion of 1-2 vector copies per cellular genome. After transduction, the cellular product is expanded and tested extensively, then cryopreserved. Viability, sterility, freedom from endotoxin and mycoplasma, inserted vector copy numbers per genome and potency (VEGF production) are performed at each batch. The GMP grade transduction, banking and qualification of MSC/VEGF is controlled by GMP SOPs, and overseen by Quality Control and Quality Assurance. A certificate of analysis is issued after completion of these tests. When needed for infusion, the frozen product is shipped, under controlled conditions, to the clinical site(s). There the product is thawed according to SOPs used for bone marrow stem cell transplantation, release tests are performed (gram stain and viability) and delivered to the surgical suite for intramuscular injection. In some studies the MSC/VEGF will be thawed and plated for 24-48 hours in hypoxic conditions prior to administration to the patient.

Figure 19:
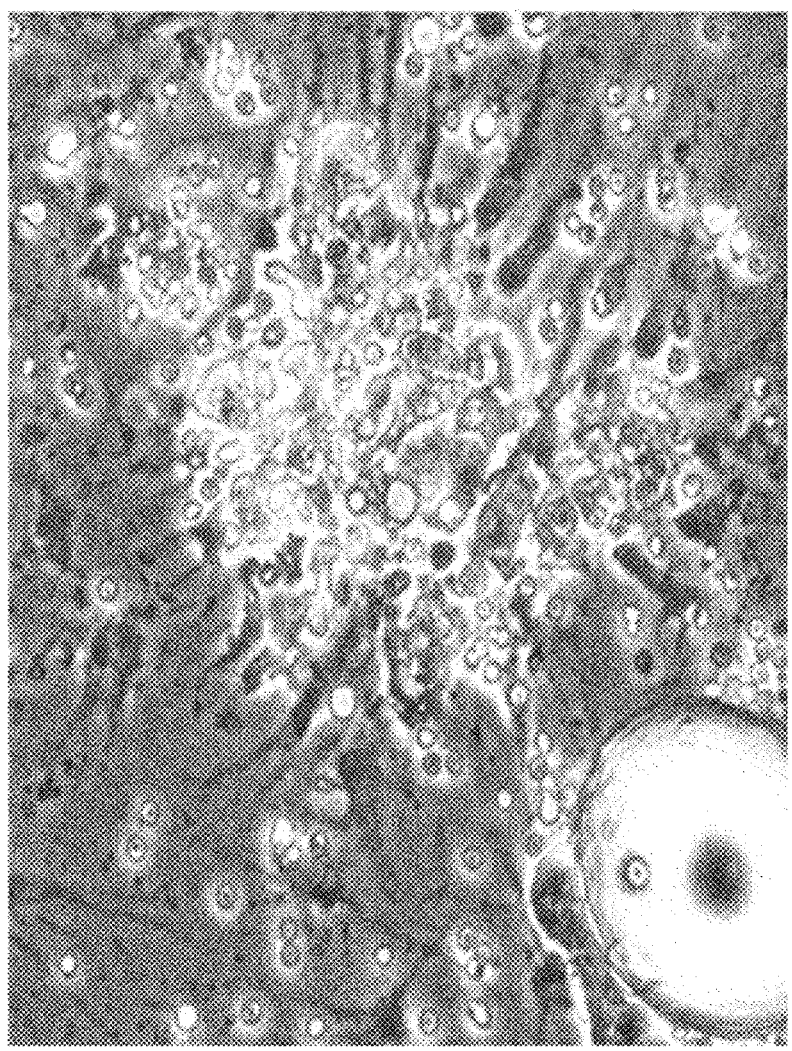

FIG. 19 shows Human MSC beginning to grow out of a bony spicule obtained by gravity sedimentation from a normal donor bone marrow aspirate as described in Example 3 (day 3 after plating).

Figure 20:
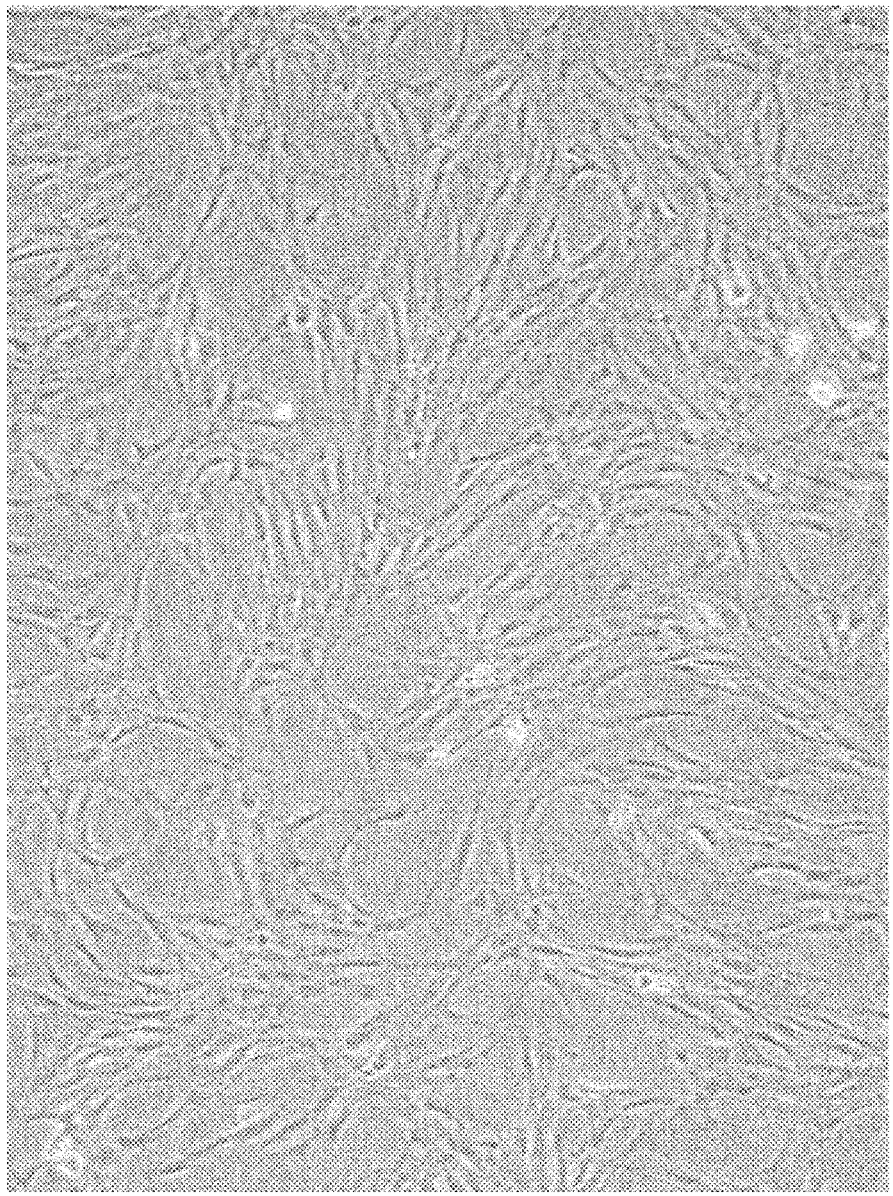

FIG. 20 shows expanded human MSC at 75% confluence as described in Example 3. This passage 3 culture was grown out of bone marrow spicules as described. The cells have a fairly uniform myofibroblastic appearance.

Figure 21:
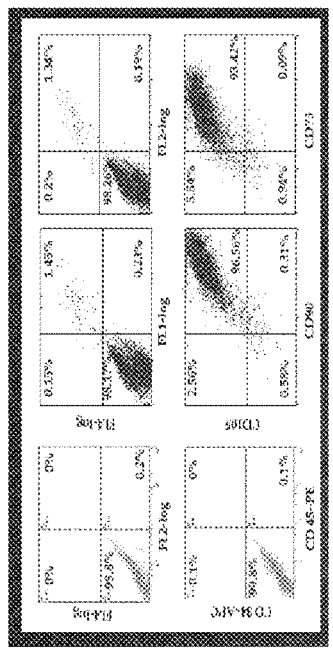

FIG. 21 shows the phenotype (by FACS assay) of Expanded Marrow Stromal Cells/Mesenchymal Stem Cells (MSCs) from human bone marrow. The phenotype depicted is: CD34−/CD45−/CD105+/CD90+/CD73+.

BRIEF DESCRIPTION OF SELECTED SEQUENCE LISTING

SEQ ID NO: 1 is the nucleotide sequence encoding for the 165A VEGF isoform.

SEQ ID NO: 2 provides the sequence of an embodiment of a vector of this disclosure. The following features are in the vector at the indicated sequence locations: 132..992 "AMP"; 2358..3070 "CMV enhanced 5'LTR"; 2892..2988 "R region 5'LTR"; 2990..3072 "U5 region 5'LTR"; 3120..3258 "PSI"; 3745..3948 "RRE"; 4461..4648 "cPPT"; 4654..4903 "Tet response element (TREmod)"; 4974..5600 "1 to 627 of VEGF; 5601..6116 "mPGK"; 6131..>6874 "rtTA-Advanced"; 6875..6940 "P2A"; 6941..8071 "WT TK cDNA [Split]"; 8166..8221 "U3 sin region 3'LTR"; 8222..8318 "R region 3' LTR"; 8320..8402 "U5 region 3' LTR".

SEQ ID NO. 23 provides the sequences of some of the elements of the pcCL3 vector as described herein. The following features are in the vector at the indicated sequence location: mRNA 4461..4648 "cPPT"; mRNA 5853..6363, "1 to 526 of muPGK(r1/xho) [Split]"; mRNA 132..992 "AMP"; mRNA, 2358..3070, "CMV enhanced 5' LTR"; mRNA 2892..2988 "R region 5'LTR"; mRNA 2990..3072 "U5 region 5' LTR"; mRNA 3120..3258 "PSI" mRNA; 3745..3948 "RRE"; mRNA, 8247..8302"U3 region 3'LTR"; mRNA8303..8399 "R region 3' LTR"; mRNA 8401..8483 "U5 region 3'LTR"; 4667..>5225 "285 to 844 of MNDU3-20H1 promoter"; mRNA <7564..>8160, "1 to 601 of WPRE (Cla) [Split]"; <6420..>7450 "WT TK cDNA [Split]"; frag 5226..5852 "1 to 627 of VEGF".

DETAILED DESCRIPTION

Definitions

Unless defined otherwise, all technical and scientific terms used herein have the same meanings as commonly understood by one of ordinary skill in the art to which this disclosure belongs. Although any methods and materials similar or equivalent to those described herein can be used in the practice or testing of the present invention, the preferred methods, devices, and materials are now described. All technical and patent publications cited herein are incorporated herein by reference in their entirety. Nothing herein is to be construed as an admission that the invention is not entitled to antedate such disclosure by virtue of prior invention.

The practice of the present disclosure will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, 3$^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Techique, 5$^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Herzenberg et al. eds (1996) Weir's Handbook of Experimental Immunology; Manipulating the Mouse Embryo: A Laboratory Manual, 3$^{rd}$ edition (Cold Spring Harbor Laboratory Press (2002)); Sohail (ed.) (2004) Gene Silencing by RNA Interference: Technology and Application (CRC Press).

All numerical designations, e.g., pH, temperature, time, concentration, and molecular weight, including ranges, are approximations which are varied (+) or (−) by increments of 0.1 or 1.0, where appropriate. It is to be understood, although not always explicitly stated that all numerical designations are preceded by the term "about." It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a cell" includes a plurality of cells, including mixtures thereof.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention or process steps to produce a composition or achieve an intended result. Embodiments defined by each of these transition terms are within the scope of this invention.

The term "isolated" as used herein with respect to nucleic acids, such as DNA or RNA, refers to molecules separated from other DNAs or RNAs, respectively that are present in the natural source of the macromolecule. The term "isolated nucleic acid" is meant to include nucleic acid fragments which are not naturally occurring as fragments and would not be found in the natural state. The term "isolated" is also used herein to refer to polypeptides, proteins and/or host cells that are isolated from other cellular proteins and is meant to encompass both purified and recombinant polypeptides. In other embodiments, the term "isolated" means separated from constituents, cellular and otherwise, in which the cell, tissue, polynucleotide, peptide, polypeptide, protein, antibody or fragment(s) thereof, which are normally associated in nature. For example, an isolated cell is a cell that is separated form tissue or cells of dissimilar phenotype or genotype. As is apparent to those of skill in the art, a non-naturally occurring polynucleotide, peptide, polypeptide, protein, antibody or fragment(s) thereof, does not require "isolation" to distinguish it from its naturally occurring counterpart.

As is known to those of skill in the art, there are 6 classes of viruses. The DNA viruses constitute classes I and II. The RNA viruses and retroviruses make up the remaining classes. Class III viruses have a double-stranded RNA genome. Class IV viruses have a positive single-stranded RNA genome, the genome itself acting as mRNA Class V viruses have a negative single-stranded RNA genome used as a template for mRNA synthesis. Class VI viruses have a positive single-stranded RNA genome but with a DNA intermediate not only in replication but also in mRNA synthesis. Retroviruses carry their genetic information in the form of RNA; however, once the virus infects a cell, the RNA is reverse-transcribed into the DNA form which integrates into the genomic DNA of the infected cell. The integrated DNA form is called a provirus.

The terms "polynucleotide", "nucleic acid" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention.

A polynucleotide or polynucleotide region (or a polypeptide or polypeptide region) has a certain percentage (for example, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: http://www.ncbi.nlm.nih.gov/cgi-bin/BLAST.

An equivalent or biological equivalent nucleic acid, polynucleotide or oligonucleotide or peptide is one having at least 80% sequence identity, or alternatively at least 85% sequence identity, or alternatively at least 90% sequence identity, or alternatively at least 92% sequence identity, or alternatively at least 95% sequence identity, or alternatively at least 97% sequence identity, or alternatively at least 98% sequence identity to the reference nucleic acid, polynucleotide, oligonucleotide or peptide.

The term "amplification of polynucleotides" includes methods such as PCR, ligation amplification (or ligase chain reaction, LCR) and amplification methods. These methods are known and widely practiced in the art. See, e.g., U.S. Pat. Nos. 4,683,195 and 4,683,202 and Innis et al., 1990 (for PCR); and Wu et al. (1989) Genomics 4:560-569 (for LCR). In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified.

Reagents and hardware for conducting PCR are commercially available. Primers useful to amplify sequences from a particular gene region are preferably complementary to, and hybridize specifically to sequences in the target region or its flanking regions. Nucleic acid sequences generated by amplification may be sequenced directly. Alternatively the amplified sequence(s) may be cloned prior to sequence analysis. A method for the direct cloning and sequence analysis of enzymatically amplified genomic segments is known in the art.

A "gene" refers to a polynucleotide containing at least one open reading frame (ORF) that is capable of encoding a particular polypeptide or protein after being transcribed and translated.

The term "express" refers to the production of a gene product.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell.

A "gene product" or alternatively a "gene expression product" refers to the amino acid (e.g., peptide or polypeptide) generated when a gene is transcribed and translated.

"Under transcriptional control" is a term well understood in the art and indicates that transcription of a polynucleotide sequence, usually a DNA sequence, depends on its being operatively linked to an element which contributes to the initiation of, or promotes, transcription. "Operatively linked" intends the polynucleotides are arranged in a manner that allows them to function in a cell. In one aspect, this invention provides promoters operatively linked to the downstream sequences, e.g., suicide gene, VEGF, 165A VEGF, tet activator, etc.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

A "probe" when used in the context of polynucleotide manipulation refers to an oligonucleotide that is provided as a reagent to detect a target potentially present in a sample of interest by hybridizing with the target. Usually, a probe will comprise a detectable label or a means by which a label can be attached, either before or subsequent to the hybridization reaction. Alternatively, a "probe" can be a biological compound such as a polypeptide, antibody, or fragments thereof that is capable of binding to the target potentially present in a sample of interest.

"Detectable labels" or "markers" include, but are not limited to radioisotopes, fluorochromes, chemiluminescent compounds, dyes, and proteins, including enzymes. Detectable labels can also be attached to a polynucleotide, polypeptide, antibody or composition described herein.

A "primer" is a short polynucleotide, generally with a free 3'-OH group that binds to a target or "template" potentially present in a sample of interest by hybridizing with the target, and thereafter promoting polymerization of a polynucleotide complementary to the target. A "polymerase chain reaction" ("PCR") is a reaction in which replicate copies are made of a target polynucleotide using a "pair of primers" or a "set of primers" consisting of an "upstream" and a "downstream" primer, and a catalyst of polymerization, such as a DNA polymerase, and typically a thermally-stable polymerase enzyme. Methods for PCR are well known in the art, and taught, for example in MacPherson et al. (1991) PCR 1: A Practical Approach (IRL Press at Oxford University Press). All processes of producing replicate copies of a polynucleotide, such as PCR or gene cloning, are collectively referred to herein as "replication." A primer can also be used as a probe in hybridization reactions, such as Southern or Northern blot analyses. Sambrook and Russell (2001), infra.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under conditions of different "stringency". In general, a low stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC. Additional examples of stringent hybridization conditions include: low stringency of incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed. Hybridization reactions can also be performed under "physiological conditions" which is well known to one of skill in the art. A non-limiting example of a physiological condition is the temperature, ionic strength, pH and concentration of $Mg^{2+}$ normally found in a cell.

When hybridization occurs in an antiparallel configuration between two single-stranded polynucleotides, the reaction is called "annealing" and those polynucleotides are described as "complementary". A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to form hydrogen bonding with each other, according to generally accepted base-pairing rules.

The term "propagate" or "expand" means to grow a cell or population of cells. The term "growing" also refers to the proliferation of cells in the presence of supporting media, nutrients, growth factors, support cells, or any chemical or biological compound necessary for obtaining the desired number of cells or cell type.

The term "culturing" refers to the in vitro propagation of cells or organisms on or in media of various kinds. It is understood that the descendants of a cell grown in culture may not be completely identical (i.e., morphologically, genetically, or phenotypically) to the parent cell.

As used herein, the term "vector" refers to a non-chromosomal nucleic acid comprising an intact replicon such that the vector may be replicated when placed within a cell, for example by a process of transformation. Vectors may be viral or non-viral. Viral vectors include retroviruses, adenoviruses, herpesvirus, bacculoviruses, modified bacculoviruses, papovirus, or otherwise modified naturally occurring viruses. Exemplary non-viral vectors for delivering nucleic acid include naked DNA; DNA complexed with cationic lipids, alone or in combination with cationic polymers; anionic and cationic liposomes; DNA-protein complexes and particles comprising DNA condensed with cationic polymers such as heterogeneous polylysine, defined-length oligopeptides, and polyethylene imine, in some cases contained in liposomes; and the use of ternary complexes comprising a virus and polylysine-DNA.

A "viral vector" is defined as a recombinantly produced virus or viral particle that comprises a polynucleotide to be delivered into a host cell, either in vivo, ex vivo or in vitro. Examples of viral vectors include retroviral vectors, lentiviral vectors, adenovirus vectors, adeno-associated virus vectors, alphavirus vectors and the like. Alphavirus vectors, such as Semliki Forest virus-based vectors and Sindbis virus-based vectors, have also been developed for use in gene therapy and immunotherapy. See, Schlesinger and Dubensky (1999) Curr. Opin. Biotechnol. 5:434-439 and Ying, et al. (1999) Nat. Med. 5(7):823-827.

In aspects where gene transfer is mediated by a lentiviral vector, a vector construct refers to the polynucleotide comprising the lentiviral genome or part thereof, and a therapeutic gene. As used herein, "lentiviral mediated gene transfer" or "lentiviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. Retroviruses carry their genetic information in the form of RNA; however, once the virus infects a cell, the RNA is reverse-transcribed into the DNA form which integrates into the genomic DNA of the infected cell. The integrated DNA form is called a provirus. As used herein, lentiviral vector refers to a viral particle capable of introducing exogenous nucleic acid into a cell through a viral or viral-like entry mechanism. A "lentiviral vector" is a type of retroviral vector well-known in the art that has certain advantages in transducing nondividing cells as compared to other retroviral vectors. See, Trono D. (2002) Lentiviral vectors, New York: Spring-Verlag Berlin Heidelberg.

Lentiviral vectors of this invention are based on or derived from oncoretroviruses (the sub-group of retroviruses containing MLV), and lentiviruses (the sub-group of retroviruses containing HIV). Examples include ASLV, SNV and RSV all of which have been split into packaging and vector components for lentiviral vector particle production systems. The lentiviral vector particle according to the invention may be based on a genetically or otherwise (e.g. by specific choice of packaging cell system) altered version of a particular retrovirus.

That the vector particle according to the invention is "based on" a particular retrovirus means that the vector is derived from that particular retrovirus. The genome of the vector particle comprises components from that retrovirus as a backbone. The vector particle contains essential vector components compatible with the RNA genome, including reverse transcription and integration systems. Usually these will include gag and pol proteins derived from the particular retrovirus. Thus, the majority of the structural components of the vector particle will normally be derived from that retrovirus, although they may have been altered genetically or otherwise so as to provide desired useful properties. However, certain structural components and in particular the env proteins, may originate from a different virus. The vector host range and cell types infected or transduced can be altered by using different env genes in the vector particle production system to give the vector particle a different specificity.

The term "promoter" refers to a region of DNA that initiates transcription of a particular gene. The promoter includes the core promoter, which is the minimal portion of the promoter required to properly initiate transcription and can also include regulatory elements such as transcription factor binding sites. The regulatory elements may promote transcription or inhibit transcription. Regulatory elements in the promoter can be binding sites for transcriptional activators or transcriptional repressors. A promoter can be constitutive or inducible. A constitutive promoter refers to one that is always active and/or constantly directs transcription of a gene above a basal level of transcription. Non-limiting examples of such include the phosphoglycerate kinase 1 (PGK) promoter; SSFV, CMV, MNDU3, SV40, Ef1a, UBC and CAGG. An inducible promoter is one which is capable of being induced by a molecule or a factor added to the cell or expressed in the cell. An inducible promoter may still produce a basal level of transcription in the absence of induction, but induction typically leads to significantly more production of the protein. Promoters can also be tissue specific. A tissue specific promoter allows for the production of a protein in a certain population of cells that have the appropriate transcriptional factors to activate the promoter.

An enhancer is a regulatory element that increases the expression of a target sequence. A "promoter/enhancer" is a polynucleotide that contains sequences capable of providing both promoter and enhancer functions. For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter.

As used herein, "stem cell" defines a cell with the ability to divide for indefinite periods in culture and give rise to specialized cells. At this time and for convenience, stem cells are categorized as somatic (adult) or embryonic. A somatic stem cell is an undifferentiated cell found in a differentiated tissue that can renew itself (clonal) and (with certain limitations) differentiate to yield all the specialized cell types of the tissue from which it originated. An embryonic stem cell is a primitive (undifferentiated) cell from the embryo that has the potential to become a wide variety of specialized cell types. An embryonic stem cell is one that has been cultured under in vitro conditions that allow proliferation without differentiation for months to years. A clone is a line of cells that is genetically identical to the originating cell; in this case, a stem cell.

A "marrow stromal cell" also referred to as "mesenchymal stem cells," or MSC, is a multipotent stem cell that can differentiate into a variety of cell types. Cell types that MSCs have been shown to differentiate into in vitro or in vivo include osteoblasts, chondrocytes, myocytes, and adipocytes. Mesenchyme is embryonic connective tissue that is derived from the mesoderm and that differentiates into hematopoietic and connective tissue, whereas MSCs do not differentiate into hematopoietic cells. Stromal cells are connective tissue cells that form the supportive structure in which the functional cells of the tissue reside. While this is an accurate description for one function of MSCs, the term fails to convey the relatively recently-discovered roles of MSCs in repair of tissue. Methods to isolate such cells, propogate and differentiate such cells are known in the technical and patent literature, e.g., U.S. Patent Application Publications 2007/0224171, 2007/0054399, 2009/0010895, which are incorporated by reference in their entirety. In one embodiment, the MSC has the phenotype CD34−/CD45−/CD105+/CD90+/CD73+.

As used herein, an "antibody" includes whole antibodies and any antigen binding fragment or a single chain thereof. Thus the term "antibody" includes any protein or peptide containing molecule that comprises at least a portion of an immunoglobulin molecule. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein, any of which can be incorporated into an antibody of the present invention. The term "antibody" is further intended to encompass digestion fragments, specified portions, derivatives and variants thereof, including antibody mimetics or comprising portions of antibodies that mimic the structure and/or function of an antibody or specified fragment or portion thereof, including single chain antibodies and fragments thereof. Examples of binding fragments encompassed within the term "antigen binding portion" of an antibody include a Fab fragment, a monovalent fragment consisting of the $V_L$, $V_H$, $C_L$ and CH, domains; a F(ab')2 fragment, a bivalent fragment comprising two Fab fragments linked by a disulfide bridge at the hinge region; a Fd fragment consisting of the $V_H$ and $C_H$, domains; a Fv fragment consisting of the $V_L$ and $V_H$ domains of a single arm of an antibody, a dAb fragment (Ward et al. (1989) Nature 341:544-546), which consists of a $V_H$ domain; and an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv)). Bird et al. (1988) Science 242:423-426 and Huston et al. (1988) Proc. Natl. Acad Sci. USA 85:5879-5883. Single chain antibodies are also intended to be encompassed within the term "fragment of an antibody." Any of the above-noted antibody fragments are obtained using conventional techniques known to those of skill in the art, and the fragments are screened for binding specificity and neutralization activity in the same manner as are intact antibodies.

As used herein, an "antibody" includes whole antibodies and any antigen binding fragment or a single chain thereof. Thus the term "antibody" includes any protein or peptide containing molecule that comprises at least a portion of an immunoglobulin molecule. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein, any of which can be incorporated into an antibody of the present invention. The term "antibody" is further intended to encompass digestion fragments, specified portions, derivatives and variants thereof, including antibody mimetics or comprising portions of antibodies that mimic the structure and/or function of an antibody or specified fragment or portion thereof, including single chain antibodies and fragments thereof. It also includes in some aspects, antibody variants, polyclonal antibodies, human antibodies, humanized antibodies, chimeric antibodies, antibody derivatives, a bispecific molecule, a multispecific molecule, a heterospecific molecule, heteroantibodies and human monoclonal antibodies.

Examples of binding fragments encompassed within the term "antigen binding portion" of an antibody include a Fab fragment, a monovalent fragment consisting of the $V_L$, $V_H$, $C_L$ and CH, domains; a F(ab')2 fragment, a bivalent fragment comprising two Fab fragments linked by a disulfide bridge at the hinge region; a Fd fragment consisting of the $V_H$ and $C_H$, domains; a Fv fragment consisting of the $V_L$ and $V_H$ domains of a single arm of an antibody, a dAb fragment (Ward et al. (1989) Nature 341:544-546), which consists of a $V_H$ domain; and an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv)). Bird et al. (1988) Science 242:423-426 and Huston et al. (1988) Proc. Natl. Acad Sci. USA 85:5879-5883. Single chain antibodies are also intended to be encompassed within the term "fragment of an antibody." Any of the above-noted antibody fragments are obtained using conventional techniques known to those of skill in the art, and the fragments are screened for binding specificity and neutralization activity in the same manner as are intact antibodies.

The term "antibody variant" is intended to include antibodies produced in a species other than a mouse. It also includes antibodies containing post-translational modifications to the linear polypeptide sequence of the antibody or fragment. It further encompasses fully human antibodies.

The term "antibody derivative" is intended to encompass molecules that bind an epitope as defined above and which are modifications or derivatives of a native monoclonal antibody of this invention. Derivatives include, but are not limited to, for example, bispecific, multispecific, heterospecific, trispecific, tetraspecific, multispecific antibodies, diabodies, chimeric, recombinant and humanized.

The term "bispecific molecule" is intended to include any agent, e.g., a protein, peptide, or protein or peptide complex, which has two different binding specificities. The term "multispecific multispecific molecule" or "heterospecific molecule" is intended to include any agent, e.g. a protein, peptide, or protein or peptide complex, which has more than two different binding specificities.

The term "heteroantibodies" refers to two or more antibodies, antibody binding fragments (e.g., Fab), derivatives thereof, or antigen binding regions linked together, at least two of which have different specificities.

The term "human antibody" as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody" as used herein, is not intended to include antibodies in which CDR sequences derived from the germline of another mammalian species, such as a mouse, have been grafted onto human framework sequences. Thus, as used herein, the term "human antibody" refers to an antibody in which substantially every part of the protein (e.g., CDR, framework, $C_L$, $C_H$ domains (e.g., $C_{H1}$, $C_{H2}$, $C_{H3}$), hinge, (VL, VH)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally and preferably retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

As used herein, a human antibody is "derived from" a particular germline sequence if the antibody is obtained from a system using human immunoglobulin sequences, e.g., by immunizing a transgenic mouse carrying human immunoglobulin genes or by screening a human immunoglobulin gene library. A human antibody that is "derived from" a human germline immunoglobulin sequence can be identified as such by comparing the amino acid sequence of the human antibody to the amino acid sequence of human germline immunoglobulins. A selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

The terms "monoclonal antibody" or "monoclonal antibody composition" as used herein refer to a preparation of antibody molecules of single molecular composition. A monoclonal antibody composition displays a single binding specificity and affinity for a particular epitope.

A "human monoclonal antibody" refers to antibodies displaying a single binding specificity which have variable and constant regions derived from human germline immunoglobulin sequences.

A population of cells intends a collection of more than one cell that is identical (clonal) or non-identical in phenotype and/or genotype. A substantially homogenous population of cells is a population having at least 70%, or alternatively at least 75%, or alternatively at least 80%, or alternatively at least 85%, or alternatively at least 90%, or alternatively at least 95%, or alternatively at least 98% identical phenotype, as measured by pre-selected markers.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the antibody, e.g., from a transfectoma, antibodies isolated from a recombinant, combinatorial human antibody library, and antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

A "composition" is intended to mean a combination of active polypeptide, polynucleotide or antibody and another compound or composition, inert (e.g. a detectable label) or active (e.g. a gene delivery vehicle).

A "pharmaceutical composition" is intended to include the combination of an active polypeptide, polynucleotide or antibody with a carrier, inert or active such as a solid support, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin (1975) Remington's Pharm. Sci., 15th Ed. (Mack Publ. Co., Easton).

A "subject," "individual" or "patient" is used interchangeably herein, and refers to a vertebrate, preferably a mammal, more preferably a human. Mammals include, but are not limited to, murines, rats, rabbit, simians, bovines, ovine, porcine, canines, feline, farm animals, sport animals, pets, equine, and primate, particularly human. Besides being useful for human treatment, the present invention is also useful for veterinary treatment of companion mammals, exotic animals and domesticated animals, including mammals, rodents, and the like which is susceptible to RNA and in particular, HIV viral infection. In one embodiment, the mammals include horses, dogs, and cats. In another embodiment of the present invention, the human is an adolescent or infant under the age of eighteen years of age.

"Host cell" refers not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

"Treating" or "treatment" of a disease includes: (1) preventing the disease, i.e., causing the clinical symptoms of the disease not to develop in a patient that may be predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

The term "suffering" as it related to the term "treatment" refers to a patient or individual who has been diagnosed with or is predisposed to infection or a disease incident to infection. A patient may also be referred to being "at risk of suffering" from a disease because of active or latent infection. This patient has not yet developed characteristic disease pathology.

An "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents of the present invention for any particular subject depends upon a variety of factors including the activity of the specific compound employed, the age, body weight, general health, sex, and diet of the subject, the time of administration, the rate of excretion, the drug combination, and the severity of the particular disorder being treated and form of administration. Treatment dosages generally may be titrated to optimize safety and efficacy. Typically, dosage-effect relationships from in vitro and/or in vivo tests initially can provide useful guidance on the proper doses for patient administration. In general, one will desire to administer an amount of the compound that is effective to achieve a serum level commensurate with the concentrations found to be effective in vitro. Determination of these parameters is well within the skill of the art. These considerations, as well as effective formulations and administration procedures are well known in the art and are described in standard textbooks. Consistent with this definition, as used herein, the term "therapeutically effective amount" is an amount sufficient to inhibit RNA virus replication ex vivo, in vitro or in vivo.

The term administration shall include without limitation, administration by oral, parenteral (e.g., intramuscular, intraperitoneal, intravenous, ICV, intracisternal injection or infusion, subcutaneous injection, or implant), by inhalation spray nasal, vaginal, rectal, sublingual, urethral (e.g., urethral suppository) or topical routes of administration (e.g., gel, ointment, cream, aerosol, etc.) and can be formulated, alone or together, in suitable dosage unit formulations containing conventional non-toxic pharmaceutically acceptable carriers, adjuvants, excipients, and vehicles appropriate for each route of administration. The invention is not limited by the route of administration, the formulation or dosing schedule.

VEGF (Vascular endothelial growth factor) is a signal protein that is known to stimulate vasculogenesis and angiogenesis. It is part of the system that restores the oxygen supply to tissues when blood circulation is inadequate. VEGF also contributes to and creates new blood vessels during embryonic development. A protein having VEGF biological activity is a protein having one or more of the biological activities of VEGF as known in the art. Seq. ID NO.: 1 is an example of a polynucleotide encoding a VEGF protein. Additional examples include the sequences available at GenBank X62568.1 and GenBank AY04758 and described in Ito et al., (2001) Cell Sign. 13(11):849-854.

As used herein, the term "thymidine kinase" or "TK" intends the thymidine kinase suicide gene "TK" that is known in the art to provide biosafety to recombinant vectors. The sequence of wild-type ("WT") TK is known in the art and provided within SEQ ID NO. 2 (nucleotides 6941-8071) and nucleotides 6420-7450 of SEQ ID NO: 23. Unless specifically recited, the term "TK" intends wild-type (WT) and/or mutant forms of the gene known in the art. Non-limiting examples of such include codon optimized TK or tk30, tk75 and sr39tk, described in Pantuck et al. (2004) Human Gene Therapy, Vol. 13(7): 777-789; Black et al. (2001) Cancer Res. 61:3022-3026; and Ardiani, et al. (2010) Cancer Gene Therapy 17:86-96 Additional examples of equivalents or biological equivalents include polynucleotides having the TK biological activity and which have at least 80%, or alternatively at least 85%, or alternatively at least 90%, or alternatively at least 95%, or alternatively at least 97% sequence identity to nucleotides 6941 to 8071 of SEQ ID NO. 2, or a polynucleotide that hybridizes under conditions of high stringency to nucleotides 6941 to 8071 of SEQ ID NO. 2, or its complement, wherein conditions of high stringency comprise incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water.

Descriptive Embodiments
Vectors

This invention provides a vector comprising, or alternatively consisting essentially of, or yet further consisting of, a nucleic acid encoding a 165A isoform VEGF protein or an equivalent thereof and a promoter that regulates expression of the nucleic acid encoding the VEGF or the equivalent thereof. In one aspect, the vector backbone contains essential sequences for integration into a target cell's genome.

In one aspect, the term "vector" intends a recombinant vector that retains the ability to infect and transduce non-dividing and/or slowly-dividing cells and integrate into the target cell's genome. In several aspects, the vector is derived from or based on a wild-type virus or plasmid, e.g., plasmid pCCLc plasmid. In further aspects, the vector is derived from or based on a wild-type lentivirus. Examples of such, include without limitation, human immunodeficiency virus (HIV), equine infectious anaemia virus (EIAV), simian immunodeficiency virus (SIV) and feline immunodeficiency virus (FIV). Alternatively, it is contemplated that other retrovirus can be used as a basis for a vector backbone such murine leukemia virus (MLV). It will be evident that a viral vector according to the invention need not be confined to the components of a particular virus. The viral vector may comprise components derived from two or more different viruses, and may also comprise synthetic components. Vector components can be manipulated to obtain desired characteristics, such as target cell specificity.

The recombinant vectors of this disclosure are derived from primates and non-primates. Examples of primate lentiviruses include the human immunodeficiency virus (HIV), the causative agent of human acquired immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV). Prior art recombinant lentiviral vectors are known in the art, e.g., see U.S. Pat. Nos. 6,924,123; 7,056,699; 7,07,993; 7,419,829 and 7,442,551, incorporated herein by reference.

U.S. Pat. No. 6,924,123 discloses that certain retroviral sequence facilitate integration into the target cell genome. This patent teaches that each retroviral genome comprises genes called gag, pol and env which code for virion proteins and enzymes. These genes are flanked at both ends by regions called long terminal repeats (LTRs). The LTRs are responsible for proviral integration, and transcription. They also serve as enhancer-promoter sequences. In other words, the LTRs can control the expression of the viral genes. Encapsidation of the retroviral RNAs occurs by virtue of a psi sequence located at the 5' end of the viral genome. The LTRs themselves are identical sequences that can be divided into three elements, which are called U3, R and U5. U3 is derived from the sequence unique to the 3' end of the RNA. R is derived from a sequence repeated at both ends of the RNA, and U5 is derived from the sequence unique to the 5' end of the RNA. The sizes of the three elements can vary considerably among different retroviruses. For the viral genome. and the site of poly (A) addition (termination) is at the boundary between R and U5 in the right hand side LTR. U3 contains most of the transcriptional control elements of the provirus, which include the promoter and multiple enhancer sequences responsive to cellular and in some cases, viral transcriptional activator proteins.

With regard to the structural genes gag, pol and env themselves, gag encodes the internal structural protein of the virus. Gag protein is proteolytically processed into the mature proteins MA (matrix), CA (capsid) and NC (nucleocapsid). The pol gene encodes the reverse transcriptase (RT), which contains DNA polymerase, associated RNase H and integrase (IN), which mediate replication of the genome.

For the production of viral vector particles, the vector RNA genome is expressed from a DNA construct encoding it, in a host cell. The components of the particles not encoded by the vector genome are provided in trans by additional nucleic acid sequences (the "packaging system", which usually includes either or both of the gag/pol and env genes) expressed in the host cell. The set of sequences required for the production of the viral vector particles may be introduced into the host cell by transient transfection, or they may be integrated into the host cell genome, or they may be provided in a mixture of ways. The techniques involved are known to those skilled in the art.

Viral vectors for use in this invention include, but are not limited to Invitrogen's pLenti series versions 4, 6, and 6.2 "ViraPower" system. Manufactured by Lentigen Corp.; pHIV-7-GFP, lab generated and used by the City of Hope Research Institute; "Lenti-X" lentiviral vector, pLVX, manufactured by Clontech; pLKO.1-puro, manufactured by Sigma-Aldrich; pLemiR, manufactured by Open Biosystems; and pLV, lab generated and used by Charité Medical School, Institute of Virology (CBF), Berlin, Germany.

In one embodiment, the vector is a viral vector. In a related embodiment, the viral vector is selected from the group consisting of a lentiviral vector, retroviral vector, adenovirus vector, adeno-associated virus vector, and alphavirus vector. In yet a further embodiment, the viral vector is a lentiviral vector. In still another embodiment, the vector and its inserts comprise, or alternatively consist essentially of, or yet further consist of, the polynucleotides of any of SEQ ID NO: 2 or 23, or an equivalent of each thereof.

Non-viral vectors may include a plasmid that comprises a heterologous polynucleotide capable of being delivered to a target cell, either in vitro, in vivo or ex-vivo. The heterologous polynucleotide can comprise a sequence of interest and can be operably linked to one or more regulatory elements and may control the transcription of the nucleic acid sequence of interest. As used herein, a vector need not be capable of replication in the ultimate target cell or subject. The term vector may include expression vector and cloning vector. In one aspect, the plasmid is the pCCLc plasmid.

In one embodiment, the additional regulatory elements are promoters, enhancer and/or promoter/enhancer combinations. The promoter that regulates expression of the nucleic acid encoding the VEGF protein can be a constitutive promoter. In one aspect, the promoter that regulates the expression of the suicide gene is a constitutive promoter. Non-limiting examples of constitutive promoters include SFFV, CMV, PKG, MDNU3, SV40, Efla, UBC, and CAGG. In one aspect, the enhancer is a Woodchuck post-regulatory element ("WPRE") (see, e.g., Zufferey, R. et al. (1999) J. Virol. 73(4):2886-2992) and SEQ ID NO. 4. The enhancer element can be downstream of the promoter and VEGF gene just before the 3' LTR. However, the enhancer can be in any location and is not limited to the 3'LTR.

In another embodiment, the promoter is an inducible promoter. In a specific related embodiment, the promoter an inducible tetracycline promoter. The Tet-Off and Tet-On Gene Expression Systems give researchers ready access to the regulated, high-level gene expression systems described by Gossen & Bujard (1992; Tet-Off) and Gossen et al. (1995; Tet-On). In the Tet-Off system, gene expression is turned on when tetracycline (Tc) or doxycycline (Dox; a Tc derivative) is removed from the culture medium. In contrast, expression is turned on in the Tet-On system by the addition of Dox. Both systems permit gene expression to be tightly regulated in response to varying concentrations of Tc or Dox. Maximal expression levels in Tet systems are very high and compare favorably with the maximal levels obtainable from strong, constitutive mammalian promoters such as CMV (Yin et al., 1996). Unlike other inducible mammalian expression systems, gene regulation in the Tet Systems is highly specific, so interpretation of results is not complicated by pleiotropic effects or nonspecific induction. In E. coli, the Tet repressor protein (TetR) negatively regulates the genes of the tetracycline-resistance operon on the Tn10 transposon. TetR blocks transcription of these genes by binding to the tet operator sequences (tetO) in the absence of Tc. TetR and tetO provide the basis of regulation and induction for use in mammalian experimental systems. In the Tet-On system, the regulatory protein is based on a "reverse" Tet repressor (rTetR) which was created by four amino acid changes in TetR (Hillen & Berens, 1994; Gossen et al., 1995). The resulting protein, rtTA (reverse tTA also referred to tetracycline activator protein), is encoded by the pTet-On regulator plasmid. This gene may be in a separate vector as the VEGF 165A gene or encoded on the same gene. For example, MSCs may first be made to express a stable cell line with the rtTA, and then the VEGF 165A with a TRE promoter can be delivered by gene transfer or by viral infection to the MSC cell line. Alternatively, the rtTA and TRE-VEGF 165A can be encoded on the same vector. In certain embodiments, the VEGF 165 A is under control of the tetracycline-response element, or TRE. TREs can be made in different ways.

In a related embodiment, the vector further comprises, or alternatively consists essentially of, or yet further consists of a nucleic acid encoding a tetracycline activator protein; and a promoter that regulates expression of the tetracycline activator protein.

Other inducible systems useful in vectors, isolated cells, viral packaging systems, and methods described herein include regulation by ecdysone, by estrogen, progesterone, chemical inducers of dimerization, and isopropyl-beta-D1-thiogalactopyranoside (EPTG).

Promoters useful in this disclosure can be constitutive or inducible. Some examples of promoters include SV40 early promoter, mouse mammary tumor virus LTR promoter, adenovirus major late promoter, herpes simplex virus promoter, and the CMV promoter. In one embodiment, the promoter that regulates expression of the tetracycline activator protein is a constitutive promoter. In other embodiments, the promoter is an inducible promoter, a tissue specific promoter, or a promoter that regulates expression temporally. In one embodiment, the promoter is a phosphoglycerate kinase promoter (PGK).

In one embodiment, the vector further comprises, or alternatively consists essentially of, or yet further consists of a suicide gene and a promoter that regulates expression of the suicide gene. A suicide gene is one that allows for the negative selection of the cells. In the methods described herein, a suicide gene is used as a safety system, allowing the cells expressing the gene to be killed by introduction of a selective agent. This is desirable in case the recombinant gene causes a mutation leading to uncontrolled cell growth. A number of suicide gene systems have been identified, including the herpes simplex virus thymidine kinase (tk or TK) gene, the cytosine deaminase gene, the varicella-zoster virus thymidine kinase gene, the nitroreductase gene, the *Escherichia coli* gpt gene, and the *E. coli* Deo gene (also see, for example, Yazawa K, Fisher W E, Brunicardi F C: Current progress in suicide gene therapy for cancer. World J. Surg. 2002 July; 26(7):783-9). In one embodiment, the suicide gene is the thymidine kinase (TK) gene. In one aspect, the TK gene is a wild-type TK gene. In other aspect, the TK gene is a mutated form of the gene. Cells expressing the TK protein can be killed using ganciclovir. In another embodiment, the nucleic acid encoding the tetracycline activator protein and the suicide gene are regulated by one promoter.

In one aspect, the promoter that regulates expression of the suicide gene is a constitutive promoter. Nucleic acids encoding different proteins may be regulated by the same promoter, produce one mRNA, and yet still result in the production of two different proteins. This can be accomplished in a variety of mechanisms. For example, a protein cleavage site can be encoded in nucleic acids between the nucleic acids encoding for the proteins. In this instance, one mRNA is produced that encodes for both proteins and the protein cleavage site. Following mRNA transcription, the mRNA is translated into a chimeric polypeptide with both proteins linked by a protease cleavage site. The protein may then be cleaved by a protease that recognizes the cleavage site. The protease may be one that is endogenously expressed or exogenously expressed from a nucleic acid transferred into the cell by gene transfer methods. Accordingly, in one embodiment, the vector further comprises, or alternatively consists essentially of, or yet further consists of a protease cleavage site between the suicide gene and the nucleic acid encoding the tetracycline activator protein. In one embodiment, the protease cleavage site is the 2A protease cleavage site. An IRES or Internal Ribosome Entry Site may also be used to produce two proteins from the same promoter. In this instance, nucleic acids encoding an IRES are cloned between the nucleic acids encoding each of the proteins. One mRNA is transcribed that encodes for both proteins, but the IRES site allows for separate translation of both proteins. Thus, two different proteins are produced by one mRNA.

In one embodiment of the disclosure, the nucleic acid encoding 165A isoform VEGF comprises the polynucleotide of SEQ ID NO: 1, or a biological equivalent thereof. In a related embodiment, the biological equivalent of VEGF comprises a nucleic acid that hybridizes under conditions of high stringency to the complement of SEQ ID NO: 1 and encodes a VEGF protein, e.g., a protein having VEGF biological activity. In another embodiment, the biological equivalent thereof comprises a nucleic acid having at least 80% sequence identity, or alternatively at least 85% sequence identity, or alternatively at least 90% sequence identity, or alternatively at least 92% sequence identity, or alternatively at least 95% sequence identity, or alternatively at least 97% sequence identity, or alternatively at least 98% sequence identity to SEQ ID NO: 1 or a polynucleotide that encodes a peptide having VEGF biological activity that hybridizes under conditions of high stringency to the complement of SEQ ID NO: 1. In a further aspect, the expressed nucleic acid is wild-type VEGF.

This disclosure also provides a vector comprising, or alternatively consisting essentially of, or yet further consisting of the following operatively linked to each other: a first promoter, a polynucleotide encoding a protein having VEGF biological activity (e.g., a wild-type VEGF or a 165A isoform VEGF protein) a second promoter and a TK gene (WT mutated or an equivalent of WT TK). In another aspect, the first and second promoter may be the same or different and can be a constitutive or inducible promoter. In a further aspect, the first and second promoters are constitutive promoters. In another aspect the disclosure provides a vector that comprises, or alternatively consisting essentially of, or yet further consists of: a 5'LTR, a MNDU3 promoter, a nucleic acid encoding a 165A isoform VEGF protein or an equivalent thereof, a phosphoglycerate kinase 1 (PGK) constitutive promoter, a TK gene (WT or mutated), an enhancer, and a 3' LTR. In one aspect, the comprises a WPRE enhancer. In a separate aspect, the 5'LTR and 3'LTR are provided in a pCCLc plasmid. An example of such is provided in SEQ ID NO. 23 and equivalents thereof.

A non-limiting example of a nucleic acid encoding a 165A isoform VEGF protein is provided in SEQ ID NO.: 1. In a related embodiment, the biological equivalent of VEGF comprises a nucleic acid that hybridizes under conditions of high stringency to the complement of SEQ ID NO: 1 and encodes a VEGF protein, e.g., a protein having VEGF biological activity. In another embodiment, the biological equivalent thereof comprises a nucleic acid having at least 80% sequence identity, or alternatively at least 85% sequence identity, or alternatively at least 90% sequence identity, or alternatively at least 92% sequence identity, or alternatively at least 95% sequence identity, or alternatively at least 97% sequence identity, or alternatively at least 98% sequence identity to SEQ ID NO: 1. In a further aspect, the expressed nucleic acid is wild-type VEGF.

In a further aspect, the disclosure provides a nucleic acid comprising, or alternatively consisting essentially of, or yet further consisting of SEQ ID. NO.: 2 or 23 or nucleotides 4654 to 8071 of SEQ ID NO: 2 or nucleotides 4667 to 8160 of SEQ ID NO: 23, a biological equivalent of each thereof. In one aspect, the biological equivalent of SEQ ID NO.: 2 or 23 or nucleotides 4654 to 8071 of SEQ ID NO: 2 or nucleotides 4667 to 8160 of SEQ ID NO: 23, comprises a nucleic acid that hybridizes under conditions of high stringency to the complement of SEQ ID NO: 2 or 23 or nucleotides 4654 to 8071 of SEQ ID NO: 2 or nucleotides 4667 to 8160 of SEQ ID NO: 23, respectively and encodes a VEGF protein, e.g., a protein having VEGF biological activity. In another embodiment, the biological equivalent thereof comprises a nucleic acid having at least 80% sequence identity, or alternatively at least 85% sequence identity, or alternatively at least 90% sequence identity, or alternatively at least 92% sequence identity, or alternatively at least 95% sequence identity, or alternatively at least 97% sequence identity, or alternatively at least 98% sequence identity to SEQ ID NO: 2 or 23 or nucleotides 4654 to 8071 of SEQ ID NO: 2 or nucleotides 4667 to 8160 of SEQ ID NO: 23, and encodes a protein having VEGF biological activity.

In a further aspect, the vector further comprises a marker or detectable label such as a gene encoding an enhanced green fluorescent protein (EGFP), red flouresence protein (RFP), green fluorescent protein (GFP) and yellow fluorescent protein (YFP) or the like. These are commercially available and described in the technical art.

Genes may be delivered to the cell by a variety of mechanisms commonly known to those of skill in the art.

Viral constructs can be delivered through the production of a virus in a suitable host cell. Virus is then harvested from the host cell and contacted with the target cell. Viral and non-viral vectors capable of expressing genes of interest can be delivered to a targeted cell via DNA/liposome complexes, micelles and targeted viral protein-DNA complexes. Liposomes that also comprise a targeting antibody or fragment thereof can be used in the methods of this invention. In addition to the delivery of polynucleotides to a cell or cell population, direct introduction of the proteins described herein to the cell or cell population can be done by the non-limiting technique of protein transfection, alternatively culturing conditions that can enhance the expression and/or promote the activity of the proteins of this invention are other non-limiting techniques.

Other methods of delivering vectors encoding genes of the current invention include but are not limited to, calcium phosphate transfection, DEAE-dextran transfection, electroporation, microinjection, protoplast fusion, or liposome-mediated transfection. The host cells that are transfected with the vectors of this invention may include (but are not limited to) *E. coli* or other bacteria, yeast, fungi, insect cells (using, for example, baculoviral vectors for expression in SF9 insect cells), or cells derived from mice, humans, or other animals (e.g., mammals). In vitro expression of a protein, fusion, polypeptide fragment, or mutant encoded by cloned DNA may also be used. Those skilled in the art of molecular biology will understand that a wide variety of expression systems and purification systems may be used to produce recombinant proteins and fragments thereof.

Packaging Systems

The invention also provides a viral packaging system comprising: the vector as described above, wherein the backbone is derived from a plasmid, a virus; a packaging plasmid; and an envelope plasmid. The packaging plasmid contains the nucleoside, capsid and matrix proteins. Examples of packaging plasmids are also described in the patent literature, e.g., U.S. Pat. Nos. 7,262,049; 6,995,258; 7,252,991 and 5,710,037, incorporated herein by reference.

The system also contains a plasmid encoding a pseudotyped envelope protein provided by an envelope plasmid. Pseudotyped viral vectors consist of vector particles bearing glycoproteins derived from other enveloped viruses or alternatively containing functional portions. See, for example U.S. Pat. No. 7,262,049, incorporated herein by reference. In a preferred aspect, the envelope plasmid encodes an envelope protein that does not cause the viral particle to unspecifically bind to a cell or population of cells. The specificity of the viral particle is conferred by the antibody binding domain that is inserted into the particle. Examples of suitable envelope proteins include, but are not limited to those containing the *Staph. aureus* ZZ domain. The choice of glycoprotein for use in the envelope is determined in part, by the antibody to which the particle may be conjugated.

This disclosure also provides the suitable packaging cell line. In one aspect, the packaging cell line is the HEK-293 cell line. Other suitable cell lines are known in the art, for example, described in the patent literature within U.S. Pat. Nos. 7,070,994; 6,995,919; 6,475,786; 6,372,502; 6,365,150 and 5,591,624, each incorporated herein by reference.

Pseudotyped Viral Particles

This invention further provides a method for producing a pseudotyped viral particle, comprising, or alternatively consisting essentially of, or yet further consisting of, transducing a packaging cell line with the viral system as described above, under conditions suitable to package the viral vector. Such conditions are known in the art and briefly described herein. The pseudotyped viral particle can be isolated from the cell supernatant, using methods known to those of skill in the art, e.g., centrifugation. Such isolated particles are further provided by this invention.

This invention further provides the isolated pseudotyped viral particle produced by this method. The pseudotyped viral particle comprises, or alternatively consists essentially of, or yet further consists of a polynucleotide encoding a 165A isoform VEGF protein or an equivalent thereof (e.g., SEQ ID NO. 1 or an equivalent of SEQ ID NO. 1 as described above) and an envelope protein comprising a ZZ *S. aureus* domain.

The isolated pseudotyped particles can be conjugate to one or more of an antibody or an antibody fragment (e.g. an fragment containing at least the Fc domain) that retains the ability to bind a pre-selected cell receptor.

The antibodies are not species specific. In other words, the antibodies can be polyclonal or monoclonal and can be murine, ovine, human or other species. In addition, they can be chimeric or humanized.

Methods to Produce the Pseudotyped Particles

This invention also provides methods to prepare a pseudotyped viral particle by transducing a packaging cell line, as described herein with the vector, the envelope plasmid and the packaging plasmid under conditions that facilitate packaging of the vector into the envelope particle. In one aspect, the pseudotyped viral particle is a pseudotyped viral particle. In a further aspect, the particles are separated from the cellular supernatant and conjugated to an antibody for cell-specific targeting.

In one aspect, the complete vector particle is a viral, or alternatively a retroviral vector pseudotyped with a Sindbis virus glycoprotein envelope containing the ZZ domain of Protein A from *Staphylococcus aureus*.

The genetic information of the viral vector particle is RNA which contains, on the 5' and 3' ends, the minimal LTR regions required for integration of the vector. In between the two LTR regions is the psi region which is required for packaging of the vector RNA into the particle. This region is followed by the RRE and cPPT sequences which enhance vector production by transporting the full length vector transcript out of the nucleus for efficient packaging into the vector particle. Also between the two LTR regions is the nucleic acid encoding the 165A isoform VEGF protein and appropriate regulatory sequences as described herein. In certain embodiments, a nucleic acid encoding a suicide gene is encoded between the LTR regions.

The full length RNA transcript is packaged inside the capsid of the vector particle which contains the nucleocapsid, capsid, and matrix proteins which are generated from the packaging plasmid delta-8.91. The reverse transcriptase polymerse which is generated from the packaging plasmid delta-8.91 is also located within the capsid with the RNA transcript. The capsid encases and protects the full length RNA transcript.

Surrounding the capsid/RNA complex is the Sindbis-ZZ glycoprotein envelope which is generated from the Sindbis-ZZ plasmid. This envelope, when conjugated with a specific monoclonal antibody, will direct the vector particle to specifically transduce a cell of interest that expresses a cell surface receptor recognized by the chosen monoclonal antibody.

The vector particle is generated by a transient transfection protocol which includes a packaging cell line (HEK-293T cells), a lipofection reagent (Transit-293T, for example), and the three plasmids encoding the parts of the vector particle (delta-8.91 (packaging plasmid)), 165A VEGF-containing vectors described herein (viral vector plasmid), and Sindbis-ZZ (envelope plasmid).

HEK-293T cells are plated at 75% confluency in complete DMEM media 24 hours prior to transfection. After at least 24 hours post-plating of cells, the transfection mixture should be prepared. Three milliliters of serum free media is incubated with 150 ul of the lipofection reagent for 20 minutes at room temperature. The three plasmids are then added to the media/lipofection reagent mixture at a ratio of 5:5:2 (packaging plasmid: viral vector plasmid: envelope plasmid) and incubated for 30 minutes. After this final incubation period, the media/lipofection reagent/DNA mixture is then added to the HEK-293T cells and left overnight for the transfection to occur. The next day, the transfection media is removed and fresh complete DMEM is added. Seventy-two hours later, the cell culture supernatant is collected and concentrated by ultracentrifugation at 20,000 rpm for 1.5 hours.

Once the vector particle buds from the packaging cells and is released into the supernatant, this vector particle is conjugated to an antibody as defined herein. In addition, the viral particle may be isolated from the supernatant. For example, packaging cells can be transfected with the viral vector by known techniques of gene transfer, the cells can be incubated for a period of time to allow the virus to replicate. The viral particles may then be isolated from the cell culture medium or supernatant by aspirating the cell culture media from the cells. The virus particles may then be sterilized by techniques known in the art (filter sterilization, for example) and/or concentrated by techniques such as centrifugation and by using commercially available concentration reagents (available from, for example, Clontech, Cat. #631231).

Isolated Host Cells

Yet further provided is an isolated cell or population of cells, comprising, or alternatively consisting essentially of, or yet further consisting of, isolated polynucleotides, viral particles, vectors and packaging systems as described above and incorporated herein by reference. In one aspect, the isolated cell is a packaging cell line.

Also provided is an isolated cell or population of cells, comprising, or alternatively consists essentially of, or yet further consisting of, a nucleic acid encoding a 165A isoform VEGF protein or an equivalent thereof and a constitutive or an inducible promoter that regulates expression of the nucleic acid encoding the VEGF. In one embodiment, the promoter is an inducible promoter as described herein. In another aspect, the promoter is a constitutive promoter as described herein. In a further aspect, the nucleic acid encoding the 165A isoform VEGF protein comprises, or alternatively consists essentially of, or yet further consists of SEQ ID NO.: 1 or an equivalent of it as described above.

In a further embodiment, the isolated cell further comprises, or alternatively consists essentially of, or yet further consists of a nucleic acid encoding a tetracycline activator protein; and a promoter that regulates expression of the tetracycline activator protein. In one embodiment, the promoter that regulates expression of the tetracycline activator protein is a constitutive promoter. In a related embodiment, the promoter is a phosphoglycerate kinase promoter (PGK).

In another embodiment, the isolated cell further comprises, or alternatively consists essentially of, or yet further consists of a suicide gene and a promoter that regulates expression of the suicide gene. In a related embodiment, the suicide gene is the thymidine kinase gene. In a further embodiment, the nucleic acid encoding the tetracycline activator protein and the suicide gene are regulated by one promoter. In a further aspect, the promoter that regulates expression of the suicide gene is a constitutive promoter. In a related embodiment, the isolated cell further comprises, or alternatively consists essentially of, or yet further consists of a protease cleavage site between the suicide gene and the nucleic acid encoding the tetracycline activator protein. In a related embodiment, the protease cleavage site is the 2A protease cleavage site.

In another embodiment, this disclosure provides an isolated host cell comprising a vector that comprises, or alternatively consists essentially of, or yet further consists of, the following operatively linked to each other: a promoter, a nucleic acid encoding a 165A isoform VEGF protein or an equivalent thereof, a promoter and a TK gene (WT or mutated). In one aspect, the vector comprises, or alternatively consists essentially of, or yet further consists of nucleotides 4654 to 8071 of SEQ ID NO: 2 or nucleotides 4667 to 8160 of SEQ ID NO: 23, or a biological equivalent of each thereof, as described above. The promoter(s) can be a constitutive or inducible, as describe herein. In a further aspect, the host cell comprises a vector that comprises, or alternatively consists essentially of, or yet further consists of, an enhancer, and a 3' LTR. In addition, a vector is provided that has the following operatively linked to each other: a 5'LTR, a MNDU3 promoter, a nucleic acid encoding a 165A isoform VEGF protein or an equivalent thereof, a phosphoglycerate kinase 1 (PGK) constitutive promoter, a TK gene (WT or mutated), an enhancer, and a 3' LTR. In a further aspect, the enhancer comprises a WPRE enhancer. In another aspect, the 5'LTR and 3'LTR are provided in a pCCLc plasmid.

In a specific embodiment, the isolated cell comprises, or alternatively consists essentially of, or yet further consists of a nucleic acid comprising the polynucleotide of SEQ ID NO: 1 that encodes a 165A isoform VEGF protein, or a biological equivalent thereof. In a related embodiment, the biological equivalent of VEGF comprises a nucleic acid that hybridizes under conditions of high stringency to the complement of SEQ ID NO: 1 and encodes a VEGF protein. In another embodiment, the biological equivalent thereof comprises a nucleic acid having at least 80% sequence identity, or alternatively at least 85% sequence identity, or alternatively at least 90% sequence identity, or alternatively at least 92% sequence identity, or alternatively at least 95% sequence identity, or alternatively at least 97% sequence identity, or alternatively at least 98% sequence identity to SEQ ID NO: 1. In a further aspect, the VEGF is wild-type VEGF.

In a further specific embodiment, the isolated cell comprises, or alternatively consists essentially of, or yet further, consists of the polynucleotide of SEQ ID NO. 2 or 23, or an equivalent of each thereof, or alternatively comprises, or consists essentially of, or yet further consists of nucleotides 4654 to 8071 of SEQ ID NO: 2 or nucleotides 4667 to 8160 of SEQ ID NO: 23, or a biological equivalent of each thereof. In one aspect, the biological equivalent of SEQ ID NO.: 2 or 23 or of nucleotides 4654 to 8071 of SEQ ID NO: 2 or nucleotides 4667 to 8160 of SEQ ID NO: 23, respectively comprises, or consists essentially of, or yet further consists of a nucleic acid that hybridizes under conditions of high stringency to the complement of SEQ ID NO: 2 or 23 of nucleotides 4654 to 8071 of SEQ ID NO: 2 or nucleotides 4667 to 8160 of SEQ ID NO: 23, respectively and encodes a VEGF protein, e.g., a protein having VEGF biological activity. In another embodiment, the biological equivalent thereof comprises a nucleic acid having at least 80% sequence identity, or alternatively at least 85% sequence identity, or alternatively at least 90% sequence identity, or alternatively at least 92% sequence identity, or alternatively at least 95% sequence identity, or alternatively at least 97% sequence identity, or alternatively at least 98% sequence identity to SEQ ID NO: 2 or 23 of nucleotides 4654 to 8071 of SEQ ID NO: 2 or nucleotides 4667 to 8160 of SEQ ID NO: 23, respectively and encodes a protein having VEGF biological activity.

The isolated cells described herein can be any of a cell of a species of the group of: murine, rats, rabbit, simians, bovines, ovine, porcine, canines, feline, farm animals, sport animals, pets, equine, and primate, and in particular a human cell. In one embodiment, the cell is a stem cell. In a related embodiment, the isolated cell is a mesenchymal stem cell. In one embodiment the MSC has the phenotype CD34−/CD45−/CD105+/CD90+/CD73+. Also provided is a population of expanded stem cells having this phenotype, and the cell can be substantially homogeneous for that phenotype. In one aspect, the cells are at least 70%, or alternatively at least 75%, or alternatively at least 80% or alternatively at least 85%, or alternatively at least 90%, or alternatively at least 95%, or alternatively at least 97% homogenous for that phenotype.

In certain embodiments, the isolated cell as described herein comprises a certain level of the 165A VEGF protein. The level of 165A VEGF protein can be achieved by selecting an appropriate constitutive promoter that produces the desirable level of protein or by using an inducible system that regulates the amount of protein produced. These promoters and inducible systems have previously been described. In one embodiment, the isolated cell comprises, or alternatively consists essentially of, or yet further, consists of at least about $5\times10^{-6}$ ng of 165A VEGF protein. In further embodiments, the isolated cell comprises, or alternatively consists essentially of, or yet further, consists of at least about $1\times10^{-7}$ ng, about $3\times10^{-7}$ ng, about $5\times10^{-7}$ ng, about $7\times10^{-7}$ ng, about $9\times10^{-7}$ ng, about $1\times10^{-6}$ ng, about $2\times10^{-6}$ ng, about $3\times10^{-6}$ ng, about $4\times10^{-6}$ ng, about $6\times10^{-6}$ ng, about $7\times10^{-6}$ ng, about $8\times10^{-6}$ ng, about $9\times10^{-6}$ ng, about $10\times10^{-6}$ ng, about $12\times10^{-6}$ ng, about $14\times10^{-6}$ ng, about $16\times10^{-6}$ ng, about $18\times10^{-6}$ ng, about $20\times10^{-6}$ ng, about $25\times10^{-6}$ ng, about $30\times10^{-6}$ ng, about $35\times10^{-6}$ ng, about $40\times10^{-6}$ ng, about $45\times10^{-6}$ ng, about $50\times10^{-6}$ ng, about $55\times10^{-6}$ ng, about $60\times10^{-6}$ ng, about $65\times10^{-6}$ ng, about $70\times10^{-6}$ ng, about $75\times10^{-6}$ ng, about $80\times10^{-6}$ ng, about $85\times10^{-6}$ ng, about $90\times10^{-6}$ ng, about $95\times10^{-6}$ ng, about $10\times10^{-5}$ ng, about $20\times10^{-5}$ ng, about $30\times10^{-5}$ ng, about $40\times10^{-5}$ ng, about $50\times10^{-5}$ ng, about $60\times10^{-5}$ ng, about $70\times10^{-5}$ ng, about $80\times10^{-5}$ ng, or about $90\times10^{-5}$ ng of 165A VEGF protein.

Compositions and Therapeutic Uses

Also provided by this invention is a composition or kit comprising any one or more of the viral vectors, isolated cells, packaging system, pseudotyped viral, viral particle conjugated to an antibody or fragment thereof which in turn may optionally be conjugated to a cell and a carrier. In one aspect, the carrier is a pharmaceutically acceptable carrier. These compositions can be used diagnostically or therapeutically as described herein and can be used in combination with other known therapies for critical limb ischemia.

This disclosure also provides a method for treating peripheral artery disease or critical limb ischemia in a patient in need thereof comprising administering the isolated cell or an expanded population of the isolated cell as described herein. Critical limb ischemia (CLI) is a severe blockage in the arteries of the lower extremities, which markedly reduces blood-flow. Patients with advanced CLI are at risk of leg amputation because blood flow to the tissue bed is occluded in atherosclerotic vessels. One approach to treatment of CLI is inducing formation of collateral blood vessels that bypass the primary blockage and restore tissue perfusion to initiate healing. Methods of this disclosure describe the use of 165A VEGF-producing cells for promoting therapeutic angiogenesis. The MSC/VEGF cells migrate into hypoxic tissue to promote revascularization, can deliver high levels of VEGF from the introduced transgene, and MSC/VEGF effect targeted release of VEGF at the site of ischemia. MSC/VEGF may be more active in promoting therapeutic angiogenesis in CLI than MSC therapies alone, VEGF protein administration, or plasmid-delivered VEGF administration.

Another aspect relates to a method for promoting wound healing, promoting or increasing the rate of angiogenesis or wound healing, decreasing the size of a wound, or decreasing the time to wound healing in a patient in need thereof comprising administering the isolated cell or an expanded population of the isolated cell as described herein. A further aspect relates to a method for salvaging a limb in a patient with critical limb ischemia comprising administering the isolated cell or an expanded population of the isolated cell as described herein.

This disclosure also relates to a method for increasing vascularization in a patient in need thereof comprising administering the isolated cell or an expanded population of the isolated cell as described herein. In one embodiment, the patient has critical limb ischemia. In a related embodiment, the vascularization is increased in the ischemic limb. This therapy may also be useful for revascularizing other tissues such as the heart, kidney, and the brain after stroke.

In certain embodiments, about 1-1000 million cells are administered to the patient in the methods described herein. Alternatively, about 1-900 million cells, about 1-800 million cells, about 1-700 million cells, about 1-600 million cells, about 1-500 million cells, about 1-400 million cells, about 1-300 million cells, about 1-200 million cells, about 1-100 million cells, about 10-900 million cells, about 10-800 million cells, about 10-700 million cells, about 10-600 million cells, about 10-500 million cells, about 10-400 million cells, about 10-300 million cells, about 10-200 million cells, about 10-100 million cells, 30-900 million cells, about 30-800 million cells, about 30-700 million cells, about 30-600 million cells, about 30-500 million cells, about 30-400 million cells, about 30-300 million cells, about 30-200 million cells, about 30-100 million cells, about 50-900 million cells, about 50-800 million cells, about 50-700 million cells, about 50-600 million cells, about 50-500 million cells, about 50-400 million cells, about 50-300 million cells, about 50-200 million cells, about 50-150 million cells, about 50-100 million cells, 100-900 million cells, about 100-800 million cells, about 100-700 million cells, about 100-600 million cells, about 100-500 million cells, about 100-400 million cells, about 100-300 million cells, or about 100-200 million cells are administered to the patient in the methods described herein.

This disclosure also provides a composition comprising a carrier and one or more of any of the disclosed isolated polynucleotides, vectors, packaging systems, and recombinant virus as described herein as well as isolated mesenchymal stem cells expressing the phenotype CD34−/CD45−/CD105+/CD90+/CD73+ and comprising a 165A VEGF polynucleotide and expanded populations of such cells. Also provided are compositions comprising the isolated cells or expanded populations of isolated cells described herein. A "composition" typically intends a combination of the active agent and another carrier, e.g., compound or composition, inert (for example, a detectable agent or label) or active, such as an adjuvant, diluent, binder, stabilizer, buffers, salts, lipophilic solvents, preservative, adjuvant or the like and include pharmaceutically acceptable carriers. Carriers also include pharmaceutical excipients and additives proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

The term carrier further includes a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Additional carriers include polymeric excipients/additives such as polyvinylpyrrolidones, ficolls (a polymeric sugar), dextrates (e.g., cyclodextrins, such as 2-hydroxypropyl-.quadrature.-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives and any of the above noted carriers with the additional provisio that they be acceptable for use in vivo. For examples of carriers, stabilizers and adjuvants, see Martin REMINGTON'S PHARM. SCI., 15th Ed. (Mack Publ. Co., Easton (1975) and Williams & Williams, (1995), and in the "PHYSICIAN'S DESK REFERENCE", 52$^{nd}$ ed., Medical Economics, Montvale, N.J. (1998).

The invention provides an article of manufacture, comprising packaging material and at least one vial comprising a solution of at least one agent or composition with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further comprises an article of manufacture, comprising packaging material, a first vial comprising at least one agent or composition and a second vial comprising an aqueous diluent of prescribed buffer or preservative, wherein said packaging material comprises a label that instructs a patient to reconstitute the therapeutic in the aqueous diluent to form a solution that can be held over a period of twenty-four hours or greater.

The formulations of the present invention can be prepared by a process which comprises mixing at least one agent or composition and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing of the antibody and preservative in an aqueous diluent is carried out using conventional dissolution and mixing procedures. For example, a measured amount of at least one antibody in buffered solution is combined with the desired preservative in a buffered solution in quantities sufficient to provide the antibody and preservative at the desired concentrations. Variations of this process would be recognized by one of skill in the art, e.g., the order the components are added, whether additional additives are used, the temperature and pH at which the formulation is prepared, are all factors that can be optimized for the concentration and means of administration used.

The compositions and formulations can be provided to patients as clear solutions or as dual vials comprising a vial of agent or composition that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available. Recognized devices comprising these single vial systems include pen-injector devices for delivery of a solution such as BD Pens, BD Autojectore, Humaject®, NovoPen®, B-D®Pen, AutoPen®, and OptiPen®, GenotropinPen®, Genotronorm Pen®, Humatro Pen®, Reco-Pen®, Roferon Pen®, Biojector®, iject®, J-tip Needle-Free Injector®, Intraject®, Medi-Ject®, e.g., as made or developed by Becton Dickensen (Franklin Lakes, N.J. available at bectondickenson.com), Disetronic (Burgdorf, Switzerland, available at disetronic.com; Bioject, Portland, Oreg. (available at bioject.com); National Medical Products, Weston Medical (Peterborough, UK, available at weston-medical.com), Medi-Ject Corp (Minneapolis, Minn., available at mediject.com).

Methods of delivery include but are not limited to intra-arterial, intra-muscular, and intravenous. In a specific embodiment, it may be desirable to administer the pharmaceutical compositions and/or cells of the disclosure locally to the area in need of treatment; this may be achieved by, for example, and not by way of limitation, local infusion during surgery, by injection or by means of a catheter. In some embodiments, the compositions or cells are administered by intravenous injection. In a further embodiment, the compositions or cells are administered by intramuscular injection. The compositions may be administered in one injection or in multiple injections. Furthermore, they may also be directly injected into ischemic areas of the diseased limb.

Solutions containing the cells can be prepared in suitable diluents such as water, ethanol, glycerol, liquid polyethylene glycol(s), various oils, and/or mixtures thereof, and others known to those skilled in the art.

Prevention or inhibition of growth of microorganisms in the formulations may be achieved through the addition of one or more antimicrobial agents such as chlorobutanol, ascorbic acid, parabens, thermerosal, or the like. It may also be preferable to include agents that alter the tonicity such as sugars or salts.

Having been generally described herein, the follow examples are provided to further illustrate this invention.

EXAMPLES

Example 1

Effects on Proliferation and Differentiation of Multipotent Bone Marrow Stromal Cells Engineered to Express Growth Factors for Combined Cell and Gene Therapy A key mechanism for mesenchymal stem cells/bone marrow stromal cells (MSCs) to promote tissue repair is by secretion of soluble growth factors. Clinical application could therefore be optimized by a combination of cell and gene therapies, where MSCs are genetically modified to express higher levels of a specific factor. However, it remains unknown how this over-expression may alter the fate of the MSCs. This example describes the effects of over-expressing the growth factors bFGF, PDGF-BB, TGF-$\beta_1$ and VEGF in human bone marrow-derived MSCs. Ectopic expression of bFGF or PDGF-B lead to highly proliferating MSCs and lead to a robust increase in osteogenesis. In contrast, adipogenesis was strongly inhibited in MSCs over-expressing PDGF-B and only mildly affected in MSCs over-expressing bFGF. Over-expression of TGF-$\beta_1$ blocked both osteogenic and adipogenic differentiation while inducing the formation of stress fibers and increasing the expression of the smooth muscle marker calponin-1 and the chondrogenic marker collagen type II. In contrast, MSCs over-expressing VEGF did not vary from control MSCs in any parameters, likely due to the lack of VEGF receptor expression on MSCs. MSCs engineered to over-express VEGF strongly induced the migration of endothelial cells and enhanced blood flow restoration in a xenograft model of hind limb ischemia. These data support the rationale for genetically modifying MSCs to enhance their therapeutically relevant trophic signals, when safety and efficacy can be demonstrated, and when it can be shown that there are no unwanted effects on their proliferation and differentiation.

Increasing evidence suggests that multipotent mesenchymal stem cells/marrow stromal cells (MSCs) represent an ontologic and phylogenetic vestige of ancestors with regenerative potential, as found during early development of mammals or adult newts, salamanders and fishes. MSCs can be isolated from virtually all vascularized tissues and are proposed to correspond with the pericyte compartment. Bone marrow-derived MSCs can reconstitute bone and bone marrow stroma at ectopic sites in immunodeficient mice and have been used for various cell therapies to treat, among many others, graft vs. host disease, cardiac infarction and epidermal fistulas. In these applications currently undergoing phase III clinical trials, MSCs are considered not to contribute significantly by direct differentiation and replacement of the damaged tissue, but rather to perform as trophic mediators, promoting tissue repair by production and release of soluble factors that inhibit inflammation, reduce fibrosis and induce angiogenesis among other functions.

The regeneration process requires orchestration of various signals including basic fibroblast growth factor (bFGF or FGF-2), platelet derived growth factor B (PDGF-BB), transforming growth factor beta1 (TGF-$\beta_1$) and vascular endothelial growth factor (VEGF). MSCs do produce and secrete bFGF, PDGF-BB, TGF-$\beta_1$ and VEGF, however, the expression levels are below those expected to have therapeutic relevance. In this context, it is essential to evaluate the effects of over-expressing growth factors (GF) in MSCs. This notion is strongly supported by a recent study that specifically identified bFGF, PDGF and TGF-$\beta$ signaling as critical pathways during proliferation and differentiation of MSCs. Over-expression of GF in MSCs may cause similar effects to those previously described when recombinant GF are supplemented in the culture media. Nevertheless, different dynamics of GF production and receptor binding may lead to unforeseen outcomes. To address this hypothesis remains essential for the planning of a combined cell and gene therapy application. In addition, the comparative analysis of over-expressing different GF in MSCs allows a better understanding of related and non-related effects.

Methods

Cell isolation and culture: Bone marrow aspirates from healthy human donors were purchased from Lonza (Allendale, N.J.). For MSC isolation and expansion, bone marrow aspirates were passed through 90 um pore strainers for isolation of bone spicules. Then, the strained bone marrow aspirates were diluted with equal volume of PBS and centrifuged over Ficoll (GE Healthcare, Waukesha, Wis.) for 30 minutes at 700×g. Next, mononuclear cells and bone spicules were plated in plastic culture flasks, using MEM-alpha (HyClone Thermo Scientific, Waltham, Mass.) supplemented with 10% fetal bovine serum (FBS; Atlanta Biologicals, Lawrenceville, Ga.) that had been screened for optimal MSC growth. After 2 days, non-adherent cells were removed by 2-3 washing steps with PBS. MSCs from passages 2 to 6 were used for experimentation. Using these methods we have demonstrated that hematopoietic stem cells and monocytes are not present in the cultures after passage 2-3[16][18]. Human umbilical vein endothelial cells (HUVEC) were isolated as previously described[19][20]. Briefly, full-term fetal umbilical cords obtained from the UC Davis Medical Center (processed following designation of the tissue as biological waste released for disposal under IRB approval) were filled in the vein with 0.2% collagenase type IV solution (Worthington, Lakewood, N.J.), incubated at 37° C. for 10 min, then flushed. Isolated cells were cultured using EGM-2 media (Lonza), with medium changes every 2-3 days. After one week in culture, over 95% of cells were CD31$^+$ as detected by flow cytometry (not shown).

Lentiviral vectors and MSC transduction: MSCs were transduced with third-generation lentiviral vectors with the form pCCLc-MNDU3-X-IRES-EGFP, where X is the insertion site for the full length cDNA of bFGF, PDGF-B, TGF-$\beta_1$, VEGF-A(165) or without insertion (as control). bFGF cDNA was subcloned from pBLAST45-hFGF2 (Invivogen, San Diego, Calif.), while cDNAs for PDGF-B, TGF-$\beta_1$ and VEGF-A(165) were derived from pCMV-SPORT6 vectors (Open Biosystems, Huntsville, Ala.). MSCs were transduced with 2 mg/ml protamine sulfate. The volume of lentivirus used for each transduction was determined by titration as the required volume to generate 80-95% GFP positive MSCs after 3 days.

Measurement of growth factor protein levels: MSCs cultured in 6-well plates (5,000 cells/cm$^2$) were transduced with the respective lentiviral vectors. 4 days later, medium was changed to 1 ml/well of MEM-alpha supplemented with 2% BSA and incubated for additional 24 h. Then, supernatants were collected in order to confirm over-expression and secretion of each factor using a human angiogenesis array (cat #AAH-ANG-1-8), following manufacturer's instructions (RayBiotech, Inc. Norcross, Ga.). To determine protein secretion by ELISA, MSCs were plated in 75 cm² culture flasks (5,000 cells/cm²) with 8 ml of MEM-alpha supplemented with 10% FBS. After 24 h, supernatants were collected and cell number determined for normalization. Then, protein levels of bFGF, PDGF-BB, TGF-$\beta_1$ and VEGF were determined by Quantikine Colorimetric Sandwich ELISAs (R&D Systems, Minneapolis, Minn.), following their provided protocols.

primers/probe mix was used as provided by Applied Biosystems (accession numbers Hs00960934_m1 and Hs00234042_m1 respectively), using GAPDH as an internal control for these taqman assays (accession number Hs99999905_m1). For all other mRNAs detected, SYBR Green Master mix (Applied Biosystems) was used for real time RT-PCR, using primers listed in Table 1. Primers were designed using OligoPerfect™ software (Invitrogen, Carlsbad, Calif.), unless denoted by a reference.

| gene | Forward primer | Reverse primer |
|---|---|---|
| ACTA2 | 5'-TCAATGTCCCAGCCATGTAT-3' (SEQ ID NO: 3) | 5'-CAGCACGATGCCAGTTGT-3' (SEQ ID NO: 4) |
| BSP | 5''-ATGGCCTGTGCTTTCTCAATG-3'' (SEQ ID NO: 5) | 5''-AGGATAAAAGTAGGCATGCTT-3'' (SEQ ID NO: 6) |
| CBFA1 | 5''-CGGAATGCCTCTGCTGTTAT-3'' (SEQ ID NO: 7) | 5''-TTCCCGAGGTCCATCTACTG-3'' (SEQ ID NO: 8) |
| CNN1 | 5''-GCTGTCAGCCGAGGTTAAGAA-3'' (SEQ ID NO: 9) | 5''-TGAGGCCGTCCATGAAGTTG-3'' (SEQ ID NO: 10) |
| FABP4 | 5'-TGAAAGAAGTAGGAGTGGGCTT-3' (SEQ ID NO: 11) | 5'-ATCCCCATTCACACTGATGATC-3 (SEQ ID NO: 12) |
| GAPDH | 5'-CTCAGTGTAGCCCAGGATGC-3' (SEQ ID NO: 13) | 5'-ACCACCATGGAGAAGGCTGG-3' (SEQ ID NO: 14) |
| PPAR-γ | 5'-TGCAGGTGATCAAGAAGACG-3' (SEQ ID NO: 15) | 5'-TGGAAGAAGGGAAATGTTGG-3' (SEQ ID NO: 16) |
| SM22 | 5'-ATGGAGCAGGTGGCTCAGTTC-3' (SEQ ID NO: 17) | 5'-ACTGCCAAGCTGCCCAAAG-3' (SEQ ID NO: 18) |
| TGF-$\beta_1$ | 5'-GGGACTATCCACCTGCAAGA-3' (SEQ ID NO: 19) | 5'-CCTCCTTGGCGTAGTAGTCG-3' (SEQ ID NO: 20) |
| VEGF-A | 5'-AGGCCAGCACATAGGAGAGA-3' (SEQ ID NO: 21) | 5'-TTTCTTGCGCTTTCGTTTTT-3'' (SEQ ID NO: 22) |

Cell proliferation: Three days after transduction with the respective lentiviral vectors, 20,000 MSCs per well were plated in duplicate in 12-well plates, with a final concentration of 2,000 cells/cm². The day after and every second day, cells were detached by trypsinization treatment and counted with Trypan Blue exclusion dye using a hemocytometer.

Western blots: For detection of activated ERK1/2 and AKT signaling pathways in MSCs, conditioned media of transduced cells was prepared by incubation of cells in 8 ml MEM-alpha+10% FBS/10⁶ cells/75 cm² flasks for 24h and stored at −80° C. Then, non-transduced MSCs (20,000 cells/cm²) were incubated for 2 h with the conditioned media that had been previously prepared, and proteins were immediately extracted using RIPA buffer (Pierce, Rockford, Ill.) supplemented with Halt protease and phosphatase inhibitor cocktail (Pierce). Proteins were loaded in 10% bis-acrylamide gels and transferred to nitrocellulose membranes. After blocking for 1 h, membranes were incubated with first antibodies overnight. Antibodies against phosphorylated and total Akt, and MAPK44/42 (ERK1/2) were purchased from Cell Signaling Technology (Danvers, Mass.).

RNA extraction and real time PCR: Total RNA was extracted with RNA-Stat 60 (Iso-Test Diagnostics, Friendswood, Tex.), following manufacturer's instructions. Reverse transcription using 1 μg of RNA was performed using Taqman reverse transcription reagents (Applied Biosystems, Foster City, Calif.). For the semi-quantification of mRNA levels of bFGF and PDGF-B, a pre-made taqman Osteogenic differentiation: For osteogenic induction assay, 10,000 MSC/cm² were cultured for 14 days in osteogenic media (MEM-alpha+10% FBS supplemented with 0.2 mM ascorbic acid, 0.1 μM dexamethasone, 10 mM β-glycerolphosphate), with a medium change every 3-4 days. To measure alkaline phosphatase activity (ALP), at day 14 the cells were trypsinized and lysed for protein extraction, with 1.5 mM Tris-HCl solution containing 1.0 mM ZnCl₂, 1.0 mM MgCl₂ and 1% Triton X-100 for 10 min. Lysates were then centrifuged at 16,100×g for 30 min and incubated with p-nitrophenylphosphate liquid substrate solution (Sigma-Aldrich, St. Louis, Mo.) for 30 min. Released p-nitrophenolate was determined spectrophotometrically at 405 nm, while total protein concentration was determined with Coomassie staining (595 nm). Calcium precipitation was measured based on a previously described protocol[26]. Briefly, cells were fixed with 10% v/v formalin solution for 15 min, washed once with PBS, stained for 20 min with gentle shaking with 1% w/v Alizarin Red S (ARS) indicator (Ricca Chemicals Company, Arlington, Tex.), washed twice with PBS and photographed with a Powershot A2000IS camera (Canon, Lake Success, N.Y.). Then, samples were incubated with 10% v/v acetic acid for 30 min, scraped for further dissociation of cell layers, vortexed for 30 seconds and centrifuged at 16,100×g for 10 min. Optic density of the supernatants was measured at 405 nm. In order to ensure that variances in calcium precipitation were not due to differences in cell number, protein concentration from control wells was determined with Coomassie staining as described above. For gene expression of osteogenic markers, RNA was extracted at day 14 as described above.

Adipogenic differentiation: MSCs were cultured in 6-well plates to confluence (approx. 15,000 cells/cm$^2$) and cultured for 14 or 21 days, with medium change every 3-4 days, in adipogenic medium (MEM-alpha+10% FBS supplemented with 0.5 mM Isobutilmethylxantine, 50 μM Indomethacin and 0.5 μM dexamethasone). For Oil Red O staining, cells were fixed after 14 days with 10% v/v formalin solution for 15 min washed once with PBS and stained for 30 min with Oil Red O (Electron Microscopy Sciences, Hatfield, Pa.). After washing twice with PBS, adipocytes were photographed under a phase contrast microscope. For detection of gene expression of adipogenic markers, RNA was extracted at day 14 as described above. For adipocyte quantification, each unstained well was photographed at day 21 in 10 randomly chosen areas. For Nile Red quantification, MSCs were trypsinized after 21 days in differentiation media and directly stained for 5 min with 10 μg/ml Nile Red (MP Biomedicals, Illkirch, France) as originally described. Then, samples were washed once with PBS and measured by FACS at 580 nm.

Cell morphology: Transduced MSCs were plated at a concentration of 5,000 cells/cm$^2$ on glass coverslips and cultured for 24 h to allow attachment and maximal spreading. Then, samples were fixed for 15 min with 4% paraforomaldehyde, permeabilized for 5 min with 0.05% Triton X-100, blocked for 1 hour with PBS+2% FBS and incubated with TRITC-labelled phalloidin (1:400, Sigma-Aldrich). Finally, samples were mounted using Vectashield Mounting Medium with DAPI (Vector Laboratories, Burlingame, Calif.) and inspected under a fluorescent microscope (Axioscope 2 plus, Zeiss, Goettingen, Germany).

HUVEC migration assay: MSCs that had been engineered to over-express each GF were cultured in 6-well plates for 24 h in standard media (10$^5$ cells/2 ml/well). Then, supernatants were collected and tested for their effect on migration of human umbilical vein endothelial cells (HUVEC). For the migration assays, HUVEC were plated in 24-well plates (1.5×10$^5$ cells/well) containing inserts from CytoSelect 24-well wound healing assay (Cell Biolabs Inc, San Diego, Calif.). After overnight incubation, inserts were removed creating a homogenous gap (or "scratch") in the monolayer of cells. Then, medium was changed to the collected supernatants from each type of GF-engineered MSCs. Wells were photographed under an inverted phase contrast microscope at time 0 and after 12 hours. Finally, the open area on acquired pictures was quantified using TScratch Software[28] (ETH, Zurich, Switzerland). The percentages of the open areas were calculated as the ratio of the area after 12 hours and 0 hours.

Hind Limb Ischemia model and blood flow restoration: All rodent work was performed under an approved animal care protocol in the UC Davis Stem Cell Program immune deficient mouse core. Under anesthesia, NOD/SCID/β-2-microglobulin-deficient mice (Jackson Laboratories—West, Sacramento, Calif.) were subjected to unilateral hind limb ischemia surgeries as we have previously described. In brief, the mice were shaved and prepped, the right femoral artery and vein were exposed and dissected from the femoral nerve, and the proximal portion of the femoral artery was ligated with 6-0 braided silk sutures. The distal portion of the saphenous artery and the remaining collateral arteries were ligated and removed from the hind limb. The wound was closed with 6-0 braided silk sutures. MSCs transduced with an empty vector or with VEGF encoding vector, as described above, were injected into the tail vein 24 hours after surgery (MSC group: n=8, VEGF group: n=6; 1×10$^6$ cells/animal). Care was taken to reduce the time from lifting the cells from the plate, washing, and injection, since MSCs can clump with time and could then form emboli when injected. Cells were injected within one hour of harvesting from the plate, with a syringe filter to remove any clumps as we have previously described.

Blood flow to the ischemic limb was measured immediately before cell transplantation (day 0) and again on day 4, 7, 14, 21, and 28 using a laser Doppler imager (Moor Instruments Ltd, Devon, UK) as previously described. For imaging, under general anesthesia, both the ischemic and the healthy legs were shaved and the animal was placed on a 37° C. heating pad for 2-5 minutes before imaging to allow acclimation to the ambient conditions before blood flow to both legs was simultaneously measured. The blood flow to the ischemic leg is expressed as a ratio relative to the contralateral healthy leg.

Data presentation and statistical analysis: All values in figures represent averages with the standard error of mean as error bars. The number of experiments performed with MSCs derived from different bone marrow donors is shown in the legend of the respective figures. All significant differences were evaluated using a paired-student t test, comparing raw data (not normalized) of conditions to control (MSCs transduced with control lentiviral vector). Throughout this manuscript, the following nomenclature is used: * $p<0.05$,  $p<0.005$, * $p<0.0005$.

Results

Figure 1:
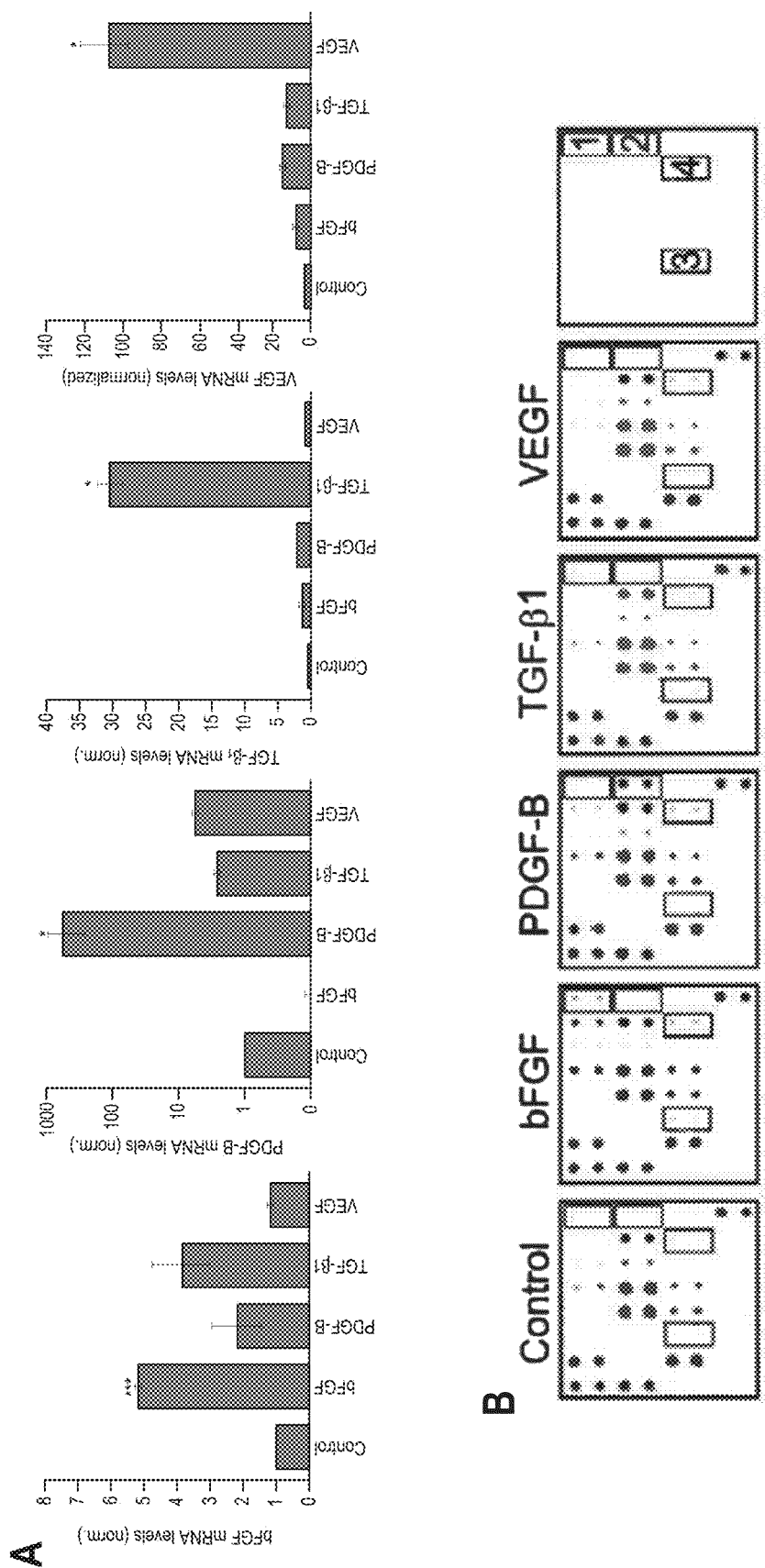
FIG. 1 shows that the overexpression of growth factors (GF) leads to activation of specific signaling pathways in MSCs. MSCs were transduced with control lentiviral vectors or those designed to overexpress GF. Over-expression of GF was then confirmed at both mRNA and protein levels. (A) mRNA was extracted from MSCs 3 days after transduction and measured by real time RT-PCR (n=3). (B) Protein levels of GF were measured in supernatant of MSCs using a human angiogenesis array, where 1=bFGF, 2=PDGF-B, 3=active TGF-$\beta_1$ and 4=VEGF. (C) Protein levels of GF measured in supernatants of MSCs using ELISA. (D) Activation of ERK1/2 and AKT1/2 was measured by western blot in MSCs as described.
Figure 1:
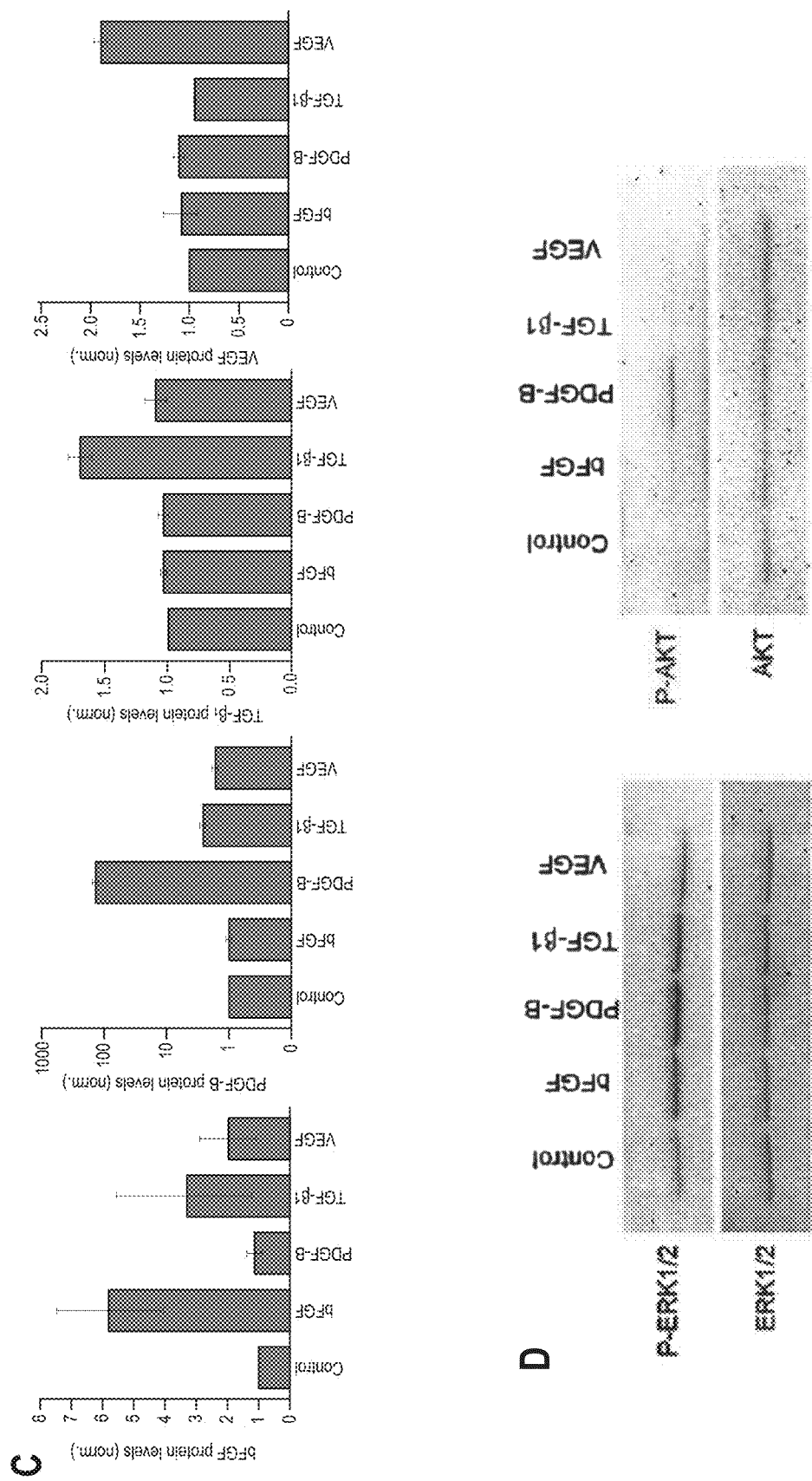

Overexpression of growth factors (GF) leads to activation of specific signaling pathways in MSCs: First, it was confirmed that lentiviral transduction with bFGF, PDGF-B, TGF-$\beta_1$ and VEGF-A lead to enhanced production and secretion of these growth factors in MSCs. As shown in FIG. 1A, the mRNA of each of the four GFs was increased upon overexpression, although in different magnitudes. Each GF was also found to be increased on a protein level, as measured in supernatants of MSCs transduced with the respective GF, as shown using an angiogenesis array (FIG. 1B) and ELISA (FIG. 1C). Remarkably, over-expression of TGF-$\beta_1$ induced an increase of bFGF at both the mRNA and protein levels. Of note, over-expression of PDGF-B lead to an over 100-fold increase of PDGF-B at both mRNA and protein levels, while over-expression of the other growth factors remained within a linear range. The overexpression of these GFs lead to the activation of specific signaling pathways in MSCs (FIG. 1C). This was tested in non-transduced MSCs incubated for 1 hour in conditioned media collected from the GF over-expressing MSCs. Conditioned media of MSCs over-expressing bFGF or PDGF-B induced phosphorylation of ERK1/2, while only PDGF-B also activated AKT. Under these conditions we do not observe phosphorylation of Smad2/3 induced by TGF-$\beta_1$. However, an increased accumulation of Smad2/3 in the nucleus of MSCs over-expressing TGF-$\beta_1$ was observed, as compared to all other conditions (data not shown). These results demonstrate effective increases of both mRNA and protein levels of each GF after lentiviral transduction, which lead to activation of specific signaling pathways in MSCs.

Figure 2:
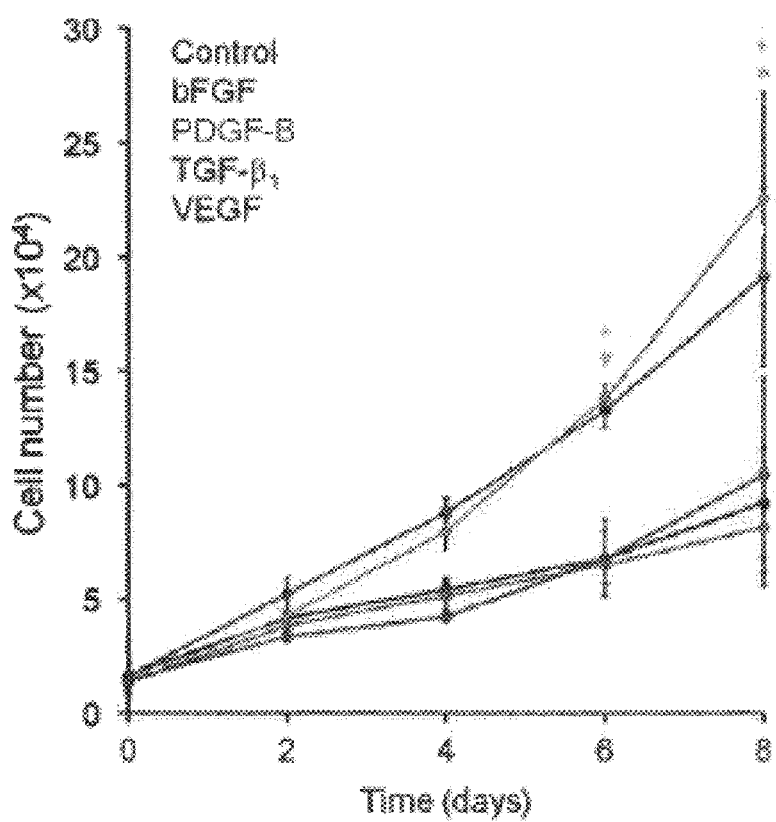
FIG. 2 shows increased proliferation in MSCs overexpressing bFGF or PDGF-B. Proliferation of MSCs overexpressing GF was measured by counting cells using trypan blue exclusion dye in a hemocytometer, as described (n=3).

Increased proliferation in MSCs over-expressing bFGF or PDGF-B: It was next sought to determine whether over-expression of any of the growth factors had a significant effect on MSC proliferation. Three days after transduction with the GF expression vectors, and every second day, a viable cell count was done (N=4 normal MSC donors). As shown in FIG. 2, over-expression of bFGF and PDGF-B lead to rapid proliferation with a reduction of about 50% in the doubling time of MSCs, as compared to MSCs transduced with a control lentiviral vector. In contrast, over-expression of TGF-$\beta_1$ and VEGF did not significantly affect MSC growth.

Osteogenic differentiation of MSCs is increased by over-expression of bFGF and PDGF-B and inhibited by TGF-$\beta_1$: To determine the effect of over-expressing GF on the osteogenic differentiation potential of MSCs, transduced cells were cultured for 14 days in osteogenic media, then calcium precipitation, alkaline phosphatase activity and gene expression of osteogenic markers was measured. Calcium precipitation as determined by Alizarin Red S staining was enhanced upon over-expression of bFGF and PDGF-B, while over-expression of TGF-$\beta_1$ strongly inhibited it (FIG. 3A). This was quantified using a previously described protocol (Gregory et al., *Anal Biochem* 2004; 329(1): 77-84), which was modified to use the total protein content as an internal loading control. This modification was introduced in order to confirm that the higher calcium precipitation is not due to the increased cell numbers. Alkaline phosphatase activity (ALP) was used as a second method to measure osteogenesis. Since it was noticed that significant levels of ALP were also found in MSCs cultured under standard conditions (i.e. no differentiation media), this condition was included as an additional control in this study. In agreement with the results on calcium precipitation, ALP increased with the over-expression of both bFGF and PDGF-B and decreased with the over-expression of TGF-$\beta_1$ (FIG. 3B). Of note, ALP levels in MSCs engineered to over-express TGF-$\beta_1$ were also significantly lower under standard culture conditions, suggesting that MSCs over-expressing TGF-$\beta_1$ were not maintained in their primitive basal state, but may have differentiated into another cell type.

Next the expression levels of mRNA known to be associated with osteogenesis were measured. No consistent differences in the mRNA levels of osteopontin, osterix or osteocalcin were found (data not shown). However, the levels of core binding factor alpha 1 (cbfa1) were surprisingly down-regulated upon over-expression of PDGF-B (FIG. 3C). Also bone sialoprotein (bsp) was unexpectedly decreased in MSCs that had been engineered to over-express bFGF or PDGF-B (FIG. 3D). Both cbfa1 and bsp mRNA levels were also measured at days 4 and 10 during osteogenesis and demonstrated the same tendencies (not shown). Also over-expression of TGF-$\beta_1$ strongly reduced bsp mRNA levels during osteogenesis.

Over-expression of PDGF-B or TGF-$\beta_1$ inhibited the adipogenic differentiation of MSCs: The adipogenic differentiation capacity from each GF-overexpressing MSC population was next evaluated using three different methods; microscopic count of adipocyte-like cells based on morphology and oil droplet accumulation, quantification by flow cytometry of cells with high triglyceride content, and by gene expression of adipogenic markers. After culturing MSCs under adipogenic induction medium for 21 days, cells with large lipid droplets were observed, except in conditions of MSCs over-expressing either PDGF-B or TGF-$\beta_1$ (FIG. 4A). This was further quantified by staining the cells with Nile Red and measuring the percentage of Nile Red positive cells by flow cytometry (FIG. 4B). Similarly, over-expression of PDGF-B or TGF-$\beta_1$ strongly decreased the number of cells with high triglyceride content. MSCs over-expressing bFGF also showed a significant reduction of Nile Red$^+$ cells, although with greater variation among donors.

Next, mRNA levels of the adipogenic markers peroxisome proliferator-activated receptor $\gamma$(ppar$\gamma$) and fatty acid binding protein 4 (fabp4) were measured in transduced MSCs after 14 days in culture under adipogenic media. Consistently, over-expression of PDGF-B or TGF-$\beta_1$ lead to reduced ppar$\gamma$ and fabp4 mRNA levels, while enforced bFGF expression in MSCs lead to only a minor, but non-significant, effect (FIGS. 4C and 4D).

Figure 3:
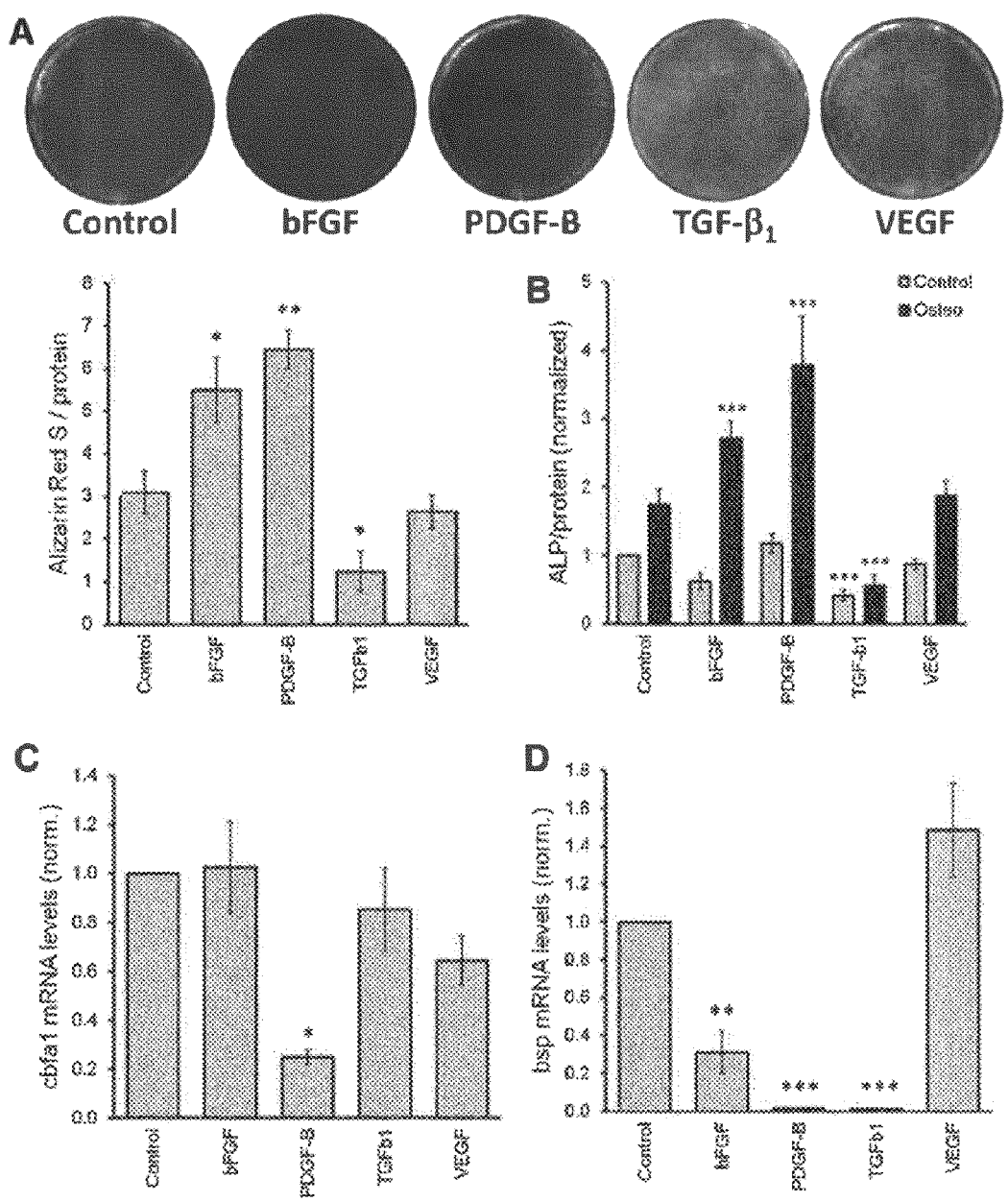
FIG. 3 demonstrates that over-expression of bFGF and PDGF-B increase the osteogenic differentiation of MSCs, while TGF-$\beta_1$ inhibits. Transduced MSCs were cultured in osteogenic media for 14 days. Then, the following assays were performed: (A) Alizarin Red S staining. Upper panel shows representative wells and lower panel the quantification (n=4)). (B) Alkaline phosphatase activity (ALP). Statistical differences are established comparing MSCs in cultured in control media (grey bars) to their respective control and MSCs in osteogenic media (black bars) to control cells cultured in osteogenic media (n=4). (C) and (D) Semi-quantification of osteogenic markers cbfa1 and bsp respectively (n=7).
Figure 4:
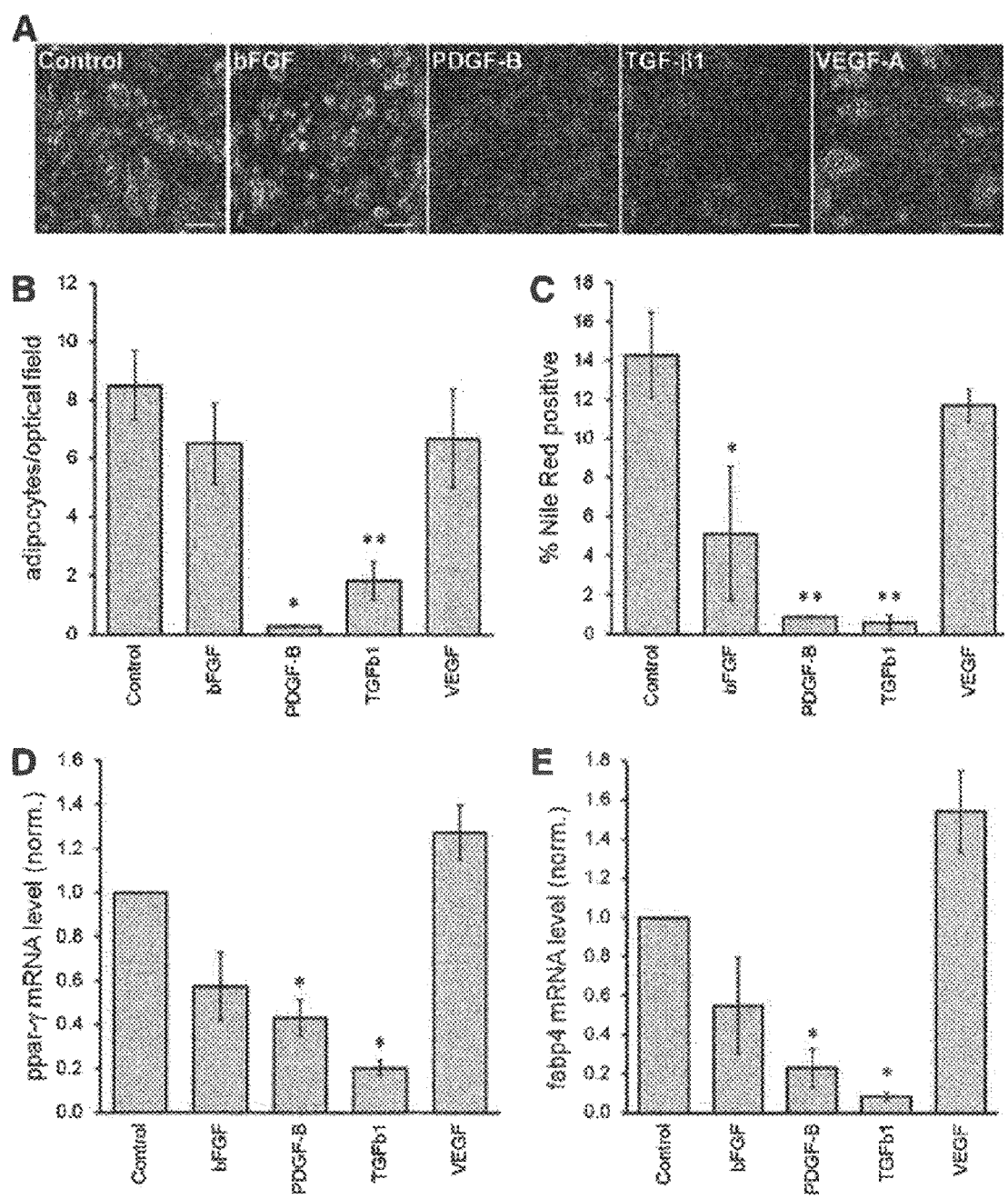
FIG. 4 shows that over-expression of PDGF-B or TGF-$\beta_1$ inhibits the adipogenic differentiation of MSCs. Transduced MSCs were cultured in adipogenic medium for 21 days. (A) Cells stained with Oil-Red O and pictured in representative areas (scale bar=100 mm). (B) Number of adipocytes counted microscopically (n=4). (C) Quantification of cells with high triglyceride, by means of Nile Red stained cells, using flow cytometry (n=3). (D) and (E) Quantification after 14 days under adipogenic media of mRNA levels of adipogenic markers ppar-g and fabp4 respectively (n=4).
Figure 5:
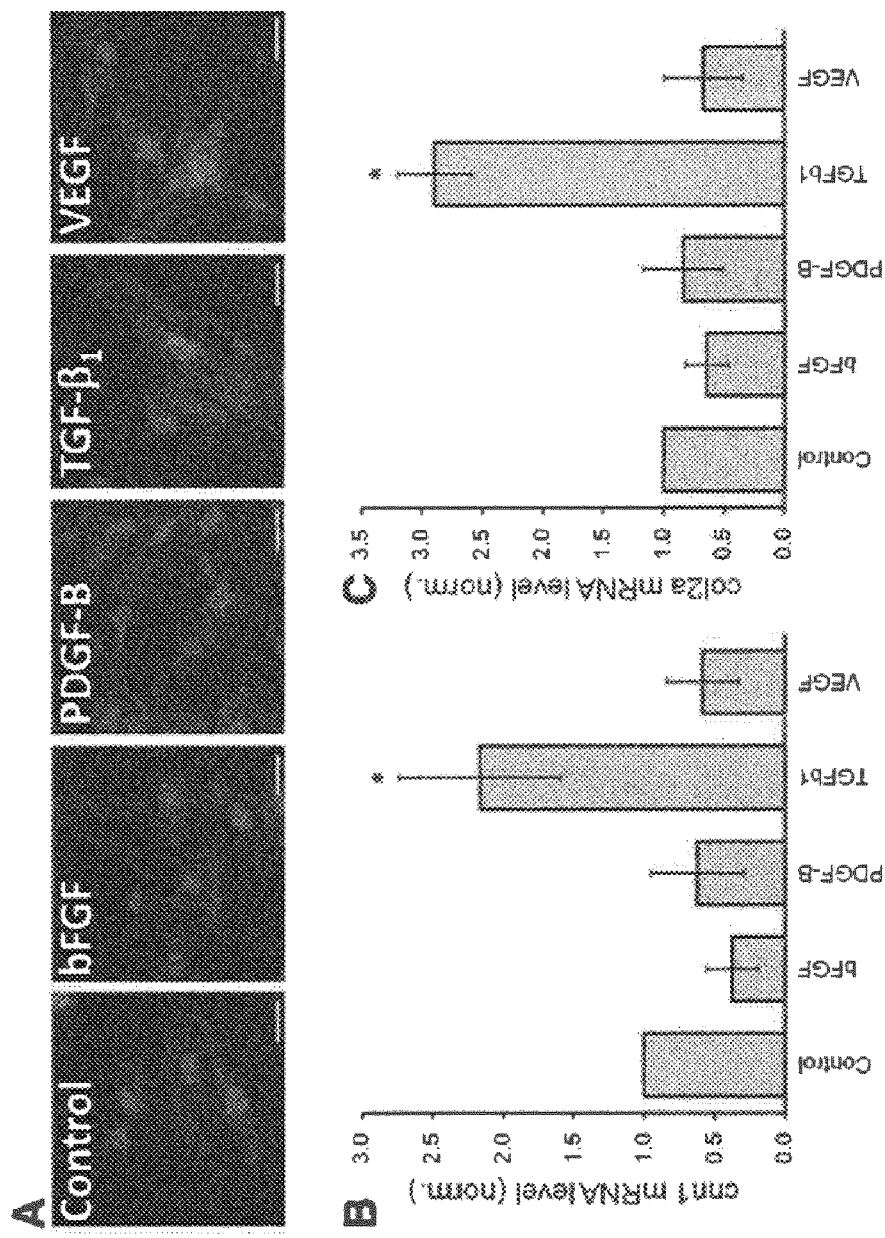
FIG. 5 shows that TGF-$\beta_1$ induces morphologic alterations in MSCs. (A) Changes in morphology of MSCs over-expressing growth factors were analyzed using phalloidin to stain actin protein (red). Cells over-expressing bFGF or VEGF did not differ from control cells. In contrast, MSCs over-expressing PDGF-B overlap and create extended protrusions. MSCs over-expressing TGF-b1 were more flattened and larger than control cells and presented abundant actin bundles characteristic of stress fibers. These changes were evident 3 days after transduction. (B) and (C) Quantification of mRNA levels of cnn1 and col2a respectively, 5 to 7 days after culture of transduced MSCs under standard conditions (without differentiation medium; n=4).

TGF-$\beta_1$—mediated effects on MSCs: Ectopic expression of TGF-$\beta_1$ in MSCs strongly inhibited their osteogenic and adipogenic differentiation potential (FIGS. 3 and 4). As mentioned above, parameters such as the alkaline phosphatase activity were found even below basal levels (i.e. MSCs incubated in normal culture media, FIG. 3B), suggesting that TGF-$\beta_1$ does not block MSC differentiation to retain them in an immature, undifferentiated state, but rather induces the differentiation of MSCs to a different cell type. It was observed that overexpression of TGF-$\beta_1$ directed strong morphological changes in MSCs that suggest that they are undergoing senescence; large, flattened polygonal shapes with actin bundles characteristic of stress fibers (FIG. 5A). However, MSCs over-expressing TGF-$\beta_1$ did not appear to undergo true senescence, since the proliferation of cells was found to be normal. In addition, a spontaneous (i.e. in absence of a specific differentiation media) increase of the smooth muscle gene calponin-1 was observed (FIG. 5B) and the chondrogenic marker Col2A (FIG. 5C). However, other smooth muscle/chondrogenic markers including a-smooth muscle actin (ACTA-2), 22 kDa smooth muscle protein (SM22), Sox9, Aggrecan and Collagen type X were not significantly affected by over-expression of TGF-$\beta_1$ (not shown). These results suggest that the changes acquired by MSCs that had been engineered to over-express TGF-$\beta_1$ did not lead to a bona fide differentiation process in vitro.

Figure 6:
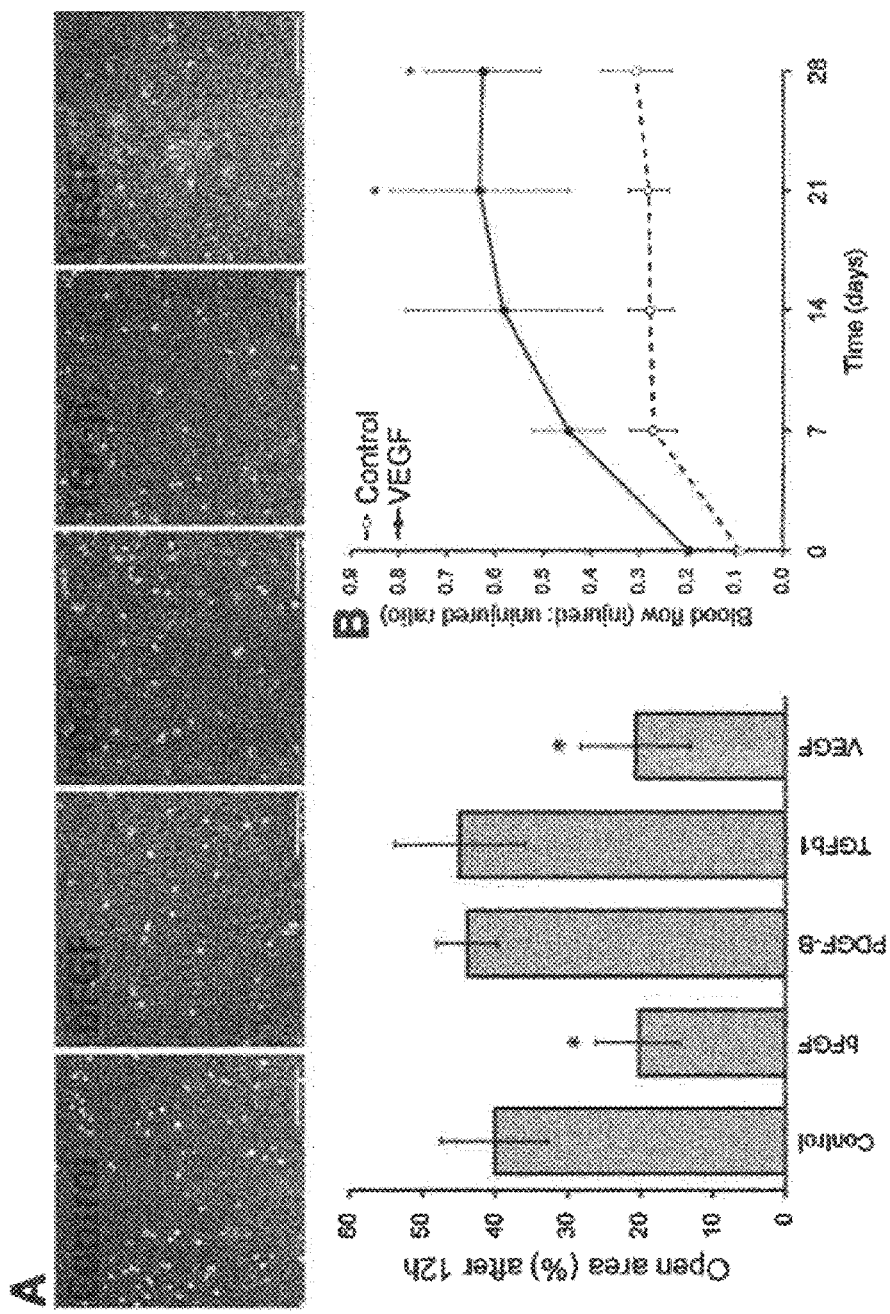
FIG. 6 shows that over-expression of bFGF and VEGF enhance migration of endothelial cells. (A) A wound healing assay was used to assess the effect of conditioned media from MSCs over-expressing GF, on the migration of HUVEC. Both representative pictures (phase contrast, upper panels) and quantification (n=4) were acquired after 12 h.

Over-expression of VEGF from MSCs enhanced migration of endothelial cells and blood flow restoration after hind limb ischemia: These results demonstrated that over-expressing VEGF in MSCs did not exert any significant effects, which is in line with the observation that MSCs do not express VEGF receptors. However, the possibility of the lack of effects exerted by VEGF potentially being due a non-functional protein product should be ruled out. Therefore, a relevant bioassay was performed to test the effects of supernatants collected from the different types of GF over-expressing MSCs on the migration of endothelial cells (HUVEC), which are well known to be responsive to VEGF. As shown in FIG. 6A, over-expression of bFGF or VEGF from MSCs strongly induced migration of HUVEC in a wound/scratch assay, demonstrating that the protein products of the gene constructs were fully functional and biologically active. Finally, it was tested whether MSCs over-expressing VEGF would also improve restoration of blood flow in mice after induction of unilateral hind limb ischemia. For this, 1 day after creating a hind limb ischemia in NOD/SCID-MPSVII mice as described above, 1 million MSCs transduced with either control or VEGF vectors were injected into the tail vein and blood flow on the ischemic limb was measured using laser Doppler imaging. As shown in FIG. 6B, under these experimental conditions, control MSCs showed only a limited improvement of blood flow, while MSCs over-expressing VEGF showed a clear improvement in revascularization over time. These in vivo data, in conjunction with the enhanced migration of endothelial cells mediated by the MSCs engineered to express VEGF, and the lack of effects on the proliferation or differentiation of the MSCs themselves, position this MSC/VEGF cell population as the best pre-clinical development candidate tested, to be considered for further testing for future revascularization studies.

The effects of growth factors (GF) on MSCs in vitro have been previously studied, commonly by adding GF as recombinant proteins to the culture media, or using small molecules to inhibit the GF receptors, both allowing the study of concentration-dependent effects. Rarely, however, are various GFs studied in a comparative manner. The effects of over-expressing GF in MSCs might be comparable to the effect of adding recombinant GF to MSC cultures, but there can also be unexpected and unwanted effects from producing GFs from a cell type that can respond to them, so this hypothesis remained to be addressed. It is believed that this is the first comparative analysis of over-expressing different growth factors that might be biologically active in a wound microenvironment in MSCs.

First the levels of growth factor over-expression acquired by MSCs after transduction with the respective lentiviral vectors were examined. According to the angiogenesis cytokine array used, the level of active TGF-$\beta_1$ found in supernatants of MSCs that had been engineered to over-express it, was rather low as compared to bFGF, PDGF-B or VEGF. All four GFs studied were cloned into the same vector backbone, the same multiplicity of infection (MOI) was used for transduction and comparable levels of GFP (driven under the same promoter, see methods) were reached for all constructs (not shown), suggesting that active TGF-$\beta_1$ levels could have been regulated on a post-transcriptional level. Mature TGF-$\beta_1$ peptides associate with latent-TGF-$\beta$-binding proteins (LTBP) localizing to the extracellular matrix, therefore reducing active TGF-$\beta_1$ levels in solution 33. Applicants speculate that since active TGF-$\beta_1$ was determined in supernatants, the latent levels of TGF-$\beta_1$ may have been underestimated. Consistent with this idea, supernatants of MSCs that had been engineered to over-express TGF-$\beta_1$ could not lead to activation of Smad2/3. In contrast, Smad2/3 was found to be constitutively active in MSCs engineered to over-express TGF-$\beta_1$, possibly through the constant exposure to it. Significant effects on the biology and morphology of the MSCs engineered to express TGF-$\beta_1$ were also noted, indicating that although the levels of protein were low, they were biologically active.

The effect of TGF-$\beta_1$ on proliferation and differentiation has been shown to be cell type and concentration dependent. In this experimental setting, it was observed that over-expression of TGF-$\beta_1$ did not significantly affect cell growth, but strongly inhibited both osteogenic and adipogenic differentiation. As previously described, TGF-$\beta_1$ induces the formation of stress fibers in MSCs and increases the expression of smooth muscle markers (Narita et al., Cell Tissue Res 2008; 333(3): 449-59). It has also been suggested that, upon contact with endothelial cells, newly recruited MSCs are induced toward a mural cell fate, in a process mediated by the activation of TGF-$\beta$(Hirschi K K, et al., Ann N Y Acad Sci 2002; 961: 223-42 and Hirschi K K, et al., J Cell Biol 1998; 141(3): 80514). On the other hand, TGF-$\beta_1$ induces differentiation of MSCs into chondrocytes and is commonly used to prove the chondrogenic potential of MSCs in vitro (Heng B C, et al., Stem Cells 2004; 22(7): 1152-67). However, the differentiation of MSCs into chondrocytes requires the growth of cells in a micromass pellet (Mackay A M, et al., Tissue Eng 1998; 4(4): 415-28). In accordance with these data, we observed that MSCs engineered to over-express TGF-$\beta_1$ acquired a complex phenotype, characterized by the expression of some smooth muscle and chondrogenic-associated genes, but not others.

The activation of signaling pathways and cell proliferation induced by these GFs clearly correlates with previous experiments using recombinant GF. A recent report described bFGF, PDGF-B, and TGF-$\beta_1$ signaling as critical for MSCs proliferation and differentiation. As expected, bFGF and PDGF-B exerted potent mitogenic effects and enhanced osteogenesis of MSCs. These results correlate with the activation of the ERK1/2 signaling pathway, since it is described to promote proliferation, increase osteogenesis and inhibit adipogenesis. However, in Applicant's studies MSCs engineered to over-express PDGF-B strongly inhibited adipogenesis, while over-expression of bFGF caused only minor effects. This difference might be associated with the activation of Akt or other signaling pathways by PDGF-B. Thus, the effects of overexpression of the growth factors in this current study appear to differ in some ways than in previous reports where the factors were simply added into the medium.

Over-expression of VEGF did not affect MSCs in terms of proliferation, differentiation and morphology, but provided strong paracrine effects to other target cells. Others have shown enhanced angiogenesis and heart repair with MSCs over-expressing VEGF, but to our knowledge, none of these groups have reported an autocrine effect induced by over-expressing VEGF. This is not surprising since MSCs do not express VEGF receptors. However, since VEGF has been shown to induce migration of MSCs by activation of PDGF receptors, it was important to assess the possibility that the migration of MSCs over-expressing VEGF might be altered. Although there were no significant effects on the MSCs themselves upon transduction with the VEGF expression vectors, there were highly significant effects on migration of human endothelial cells. These data support the potential of these VEGF-producing MSCs to assist in therapeutic angiogenesis.

This work closely compares the expression of four different growth factors that were predicted to be biologically active in a wound microenvironment. The effects on proliferation, differentiation and bioactivity on endothelial cells were compared. The study demonstrates that, in particular, MSCs engineered to express VEGF did not have abnormalities in proliferation and differentiation, but were potent inducers of endothelial migration and enhanced revascularization in vivo. These data suggest that MSCs engineered to overproduce VEGF in a controlled manner might be a future candidate for augmentation of revascularization. Taken together, this work supports the rationale for genetically modifying MSCs in order to affect their proliferation and direct their differentiation fates, while enhancing therapeutically relevant signals, such as their angiogenic potential.

These results are most relevant in the context of combining cell and gene therapy. For example, administration of plasmids coding for bFGF and VEGF for the treatment of coronary artery disease and critical limb ischemia and PDGF-BB to treat chronic wounds for diabetic patients have been performed in human clinical trials. The results however, have been unsatisfactory due to the low sustainability of the growth factors at the required sites. Since MSCs show a positive tropism to hypoxic sites, are safe (non-tumorigenic), and well tolerated in allogeneic transplants, this example demonstrates that it is well conceivable to use MSCs as vehicles for the delivery of the required growth factor. However extensive safety and efficacy testing must be done before this type of cell/gene therapy could ever be considered. The current studies provide detailed molecular and physical characterization of MSCs engineered to produce four growth factors that could potentially have been considered as development candidates. Through these studies we have ruled out three of the cell populations due to unwanted effects of the engineered growth factors on the biology for the MSCs, and have identified one candidate, MSCs engineered to produce VEGF, that is eligible and promising to go forward into further, more detailed translational studies for revascularization therapies.

Example 2

Intramuscular (IM) Injection of VEGF Producing MSC for the Treatment of Critical Limb Ischemia (CLI)

MSC/VEGF (165A Isoform):

MSC/VEGF is a sterile, cryopreserved suspension of cultured human mesenchymal stem cells [MSCs] transduced by a lentiviral vector to secrete human vascular endothelial growth factor 165A (VEGF). The product is formulated in physiological saline. In addition to meeting all safety and viability criteria, thawed product produces between 10-50 ng VEGF/ml/$10^6$ cells/24 h in culture after dox induction, as measured by ELISA of culture supernatant.

MSC/VEGF has been designed and will be administered to provide high local concentrations of vascular endothelial growth factor-$A_{165}$ (VEGF) in the affected limb of a CLI patient in order to induce revascularization, restore perfusion, and effect tissue repair. This product is to produce a gene modified cell therapy product (MSC/VEGF); safety modified, allogeneic donor-derived human mesenchymal stem cells (MSCs) engineered to increase amputation free survival of critical limb ischemia (CLI) patients. The goal is to achieve a statistically significant reduction in major amputation (limb salvage) in subjects with CLI (Rutherford category 4-5), as compared to a placebo control. Secondary endpoints may include: 1) wound healing from baseline to 6 months following the first treatment: Rate, size, and time to heal. 2) incidence of target limb revascularization (TLR). 3) time to major amputation of index leg or death. 4) change in baseline ABI/TBI. 5) change in baseline tissue perfusion measurements. Further endpoints may include improvement of rest pain, wound healing, or other clinically important parameters.

In addition to routine clinical observations, VEGF levels in the bloodstream can be measured, the injection site is monitored for adverse events such as discoloration or angioma, and the tissue can be monitored for observable changes or palpatations. Additionally, inverse PCR assays can be performed to rule out monoclonal expansion of transduced cells.

Edema from overproduction of VEGF can be addressed by regulating the transgene with doxycycline. Persistent serious edema may necessitate adjusting dose of MSC/VEGF. Risks from using transduced cells, although low, include insertional mutagenesis. The vector has been modified with the TK suicide gene to permit destruction of cells if they were to show uncontrolled multiplication or VEGF secretion.

Optimally, product is administered one time, intramuscularly, as a split dose as described below. The final frozen MSC/VEGF product is thawed and immediately administered using angiosome mapping to guide multi-site IM injections to ischemic areas of the target limb. 50 to 150 million thawed cells per limb are administered.

Patients can be treated serially with three increasing doses of MSC/VEGF (50 to 150 million cells). Angiosome mapping can be used to detect the most severely ischemic region of each patient's leg and to guide intramuscular delivery of MSC/VEGF into that region. This, along with the ability of MSC/VEGF to home to ischemic tissue, will enhance the likelihood that MSC/VEGF will focus delivery of VEGF at the target tissue. Secondary endpoints include avoidance of major amputation (limb salvage) and improved tissue perfusion assessed by 7 methods, to indicate if MSC/VEGF has the anticipated biological activity in CLI patients within the dose range administered.

In preclinical IND-enabling studies, it was demonstrated that the MSC/VEGF agent is safe and highly potent. In these studies, human MSC/VEGF revascularized the ischemic limbs of immune deficient mice to a degree that was better than MSC alone, with a statistically significant difference (Example 1).

VEGF expression is under inducible control by doxycycline administration, enabling control of VEGF made in the affected limb by administration of this antibiotic to patients, and the vector also has a thymidine kinase "suicide gene" for additional biosafety. The vector can be under GMP conditions and can be tested regularly for stability.

Following transplantation, MSC, which are expanded from adult progenitor cells, are not prone to tumor formation, and appear to tolerize the immune response across donor mismatch. These attributes combine to allow MSC to reside in many different tissue types without disrupting the local microenvironment, and in some cases, responding to the local environment with appropriate protein secretion.

In the MSC/VEGF delivery vehicle, a thymidine kinase (TK) "suicide gene" can be used to eliminate a graft if any adverse events occur. The most widely used suicide gene in human imaging and gene therapy trials is the HS V-thymidine kinase (TK) gene. It is the target of the FDA-approved drug ganciclovir that kills TK-expressing cells infected by Herpes virus. The clinical vector includes the TK gene. Efficient in vivo elimination of TK gene-transduced cells by administration of ganciclovir has been demonstrated with this strategy.

During the angiogenic process mediated by MSC, cells are not considered to contribute significantly by direct differentiation and replacement of blood vessels, but rather to perform as trophic mediators, promoting tissue repair by production and release of soluble factors that induce angiogenesis. Critical growth factors identified during the wound repair process include basic fibroblast growth factor (bFGF or FGF-2), platelet derived growth factor B (PDGF-BB), transforming growth factor beta1 (TGF-$\beta_1$) and vascular endothelial growth factor (VEGF-$A_{165}$). MSC do produce and secrete bFGF, PDGF-BB, TGF-$\beta_1$ and VEGF, however, the expression levels are below those expected to have therapeutic relevance. Therefore, an optimal design to achieve tissue regeneration would combine cell and gene therapy, where MSC are genetically modified to overexpress these growth factors. In order to engineer MSC to express higher amounts of these growth factors, MSC were transduced with a lentiviral vector (FIG. 7), where the transgene corresponded to bFGF, PDGF-B, TGF-$\beta_1$ or VEGF-$A_{165}$. As control, MSC were transduced with the same lentiviral vector lacking this transgene.

Three to four days after transduction, supernatant of cells was collected to determine secreted protein levels. In addition, RNA of cells was extracted to determine gene expression levels. As shown in FIG. 7 (right), an over 30 fold increase of VEGF-$A_{165}$ mRNA and 2 fold increase of VEGF-$A_{165}$ protein levels was observed. It was next demonstrated that over-expression of bFGF, PDGF-B, and TGF-$\beta_1$ had effects on the differentiation and/or proliferation of the MSC, whereas expression of VEGF-$A_{165}$ did not affect cell growth or differentiative capacity (FIG. 8). These results demonstrated that over-expressing VEGF in MSC did not exert any significant autocrine effects, which is in line with the observation that MSC do not express VEGF receptors.

Next, the effects of supernatants collected from the different types of GF over-expressing MSC on the migration of endothelial cells (HUVEC), which are well known to be responsive to angiogenic factors were tested. The wound/scratch assay performed determines the open area left in a monolayer of HUVEC, 12 hours after having established a constant gap of 0.9 mm diameter in a monolayer of HUVEC. As shown in FIG. 9, over-expression of bFGF or VEGF from MSC strongly induced migration of HUVEC in this assay, demonstrating that the protein products of the gene constructs were fully functional and biologically active. MSC/VEGF was therefore the best candidate for promoting wound closure by trophic factor secretion.

The MSC/VEGF stem cell product was chosen as the best candidate to study further in angiogenic assays, due to the lack of autocrine signaling of VEGF and the efficacy in inducing endothelial cell migration using the in vitro HUVEC potency assay (FIG. 9). The immune deficient mouse model of hindlimb ischemia (HLI), which is an established assay to detect angiogenic activity for cells to be used in revascularization therapies has previously been described in the art. In brief, a 1 cm segment of the right femoral artery is excised with collateral vessel ligation to induce complete hind limb ischemia. Mice are transplanted with candidate tissue-repairing stem/progenitor populations, control populations, or mock injected with PBS 24 hours after surgery. Mice are monitored 2× weekly by laser Doppler perfusion imaging for 4 weeks. FIG. 10 shows the initial lack of blood flow through the major artery in the right hindlimb, and enhanced correction by IV infusion of a clinical development candidate, but not the control cell population. This model is an approved potency assay that provides a reproducible and clinically relevant method for assessing restoration of blood flow by human cells, in place under GLP conditions.

The human stem cells can be tracked into the area of hypoxia using either luciferase/IVIS or fluorescent nanoparticle imaging (FIG. 11). This allows useful mechanistic studies for efficacy evaluations but neither tracking method can be used clinically. Previous data demonstrates the propensity of human stem cells to migrate toward areas of hypoxic damage.

It was tested whether MSC/VEGF would also improve restoration of blood flow in mice after induction of unilateral hind limb ischemia. For this, 1 day after creating a hind limb ischemia in immune deficient mice, One million MSC transduced with either control or VEGF vectors were transplanted into the mice and blood flow on the ischemic limb was measured using laser Doppler imaging. As shown in FIG. 12 under these experimental conditions, control MSC showed only a limited improvement of blood flow, while MSC/VEGF showed a clear improvement in revascularization over time. This confirms the basic premise of the proposed study-that MSC/VEGF will be more effective than MSC in revascularizing ischemic tissue.

Clinical Application—Utility

In vitro and in vivo studies are performed to test the pharm/toxic parameters of the therapeutic candidate. The test article is safety-modified allogeneic donor bone marrow-derived human mesenchymal stem cells engineered to secrete Vascular Endothelial Growth Factor (MSC/VEGF), under the control of an inducible promoter. Conditioned medium from MSC/VEGF is tested in vitro for efficacy in human endothelial cell wound closure and ELISA to measure the levels of active VEGF secreted, among others. The human MSC/VEGF development candidate was proven efficacious in a rodent model of hindlimb ischemia, through significant enhancement of revascularization as compared to non-gene-modified MSC (FIG. 12). The development candidate MSC/VEGF is safe as tested in sensitive long-term rodent models. No edema or other adverse events have been detected (FIG. 13).

To assess the effect of MSC/VEGF on the migration of HUVEC, in vitro would healing assays were performed using conditioned media from MSC/VEGF (FIG. 9). To determine VEGF protein levels in MSC culture supernatant at defined times after doxycycline induction, an ELISA was performed (FIG. 14). The RNA induction of VEGF-A165 was also assessed (FIG. 7). Karyotypic stability, phenotype and tests for the reliable expansion, migration and differentiation potential of MSC lots are established and routine in the GLP studies.

Using in vitro potency assays, a lot of MSC/VEGF produced in the UCD GMP facility without certification but using the same SOPs and reagents that will be used for the clinical lot was tested. Production of VEGF by MSCs did not alter cell growth rates, cell surface phenotype, or their osteogenic or adipogenic potential. This is likely due the lack of VEGF receptor expression on MSCs. Effects on wound closure/HUVEC migration are significantly higher from MSC/VEGF conditioned medium than from non-transduced controls. ELISA to measure VEGF production at increasing levels of doxycycline administration was performed in triplicate and is shown in FIG. 14.

From these levels, at the cell numbers injected, a maximum of 2.5 ug VEGF was expected to be produced from the lowest dose of MSC/VEGF and 7.5 ug from the highest cell dose: 150 million cells. This is a potentially therapeutic range and actual levels will depend on cell survival in the patients' ischemic tissue, with each arm of the study. In prior studies transient edema was only observed at very high doses of VEGF delivery via plasmid. The ability of MSCs to counteract the potential for VEGF A to promote vascular leakiness through expression of VE-cadherin will further temper effects and, accordingly, edema in mice treated with IM injection of MSC/VEGF was not observed (FIG. 13).

The use of MSC to deliver factors, both through their own innate responses and through engineering, has benefits over direct protein administration, because transplanted MSCs have been shown to provide sustained and long-term delivery of factors at supraphysiological levels. Using immune deficient mouse models, human MSC have been recovered from numerous organs at timepoints from 1-18 months post-transplantation, with continued expression of the gene product. A decade-long biosafety study has also been done to demonstrate that genetically engineered human MSC are safe and do not cause adverse events in vivo.

Efficacy and biosafety of the MSC/VEGF development candidate in a very permissive model of immune deficient mice has been studied. The NOD/SCID/IL2rg−/− (NSG) strain completely lacks an immune system and is a highly sensitive model for biosafety testing. Extensive biosafety testing in this strain and others has been done for IND-enabling studies in the past. As shown in FIGS. 7-13, Human MSC/VEGF generated using the GMP SOPs were safe and potent at revascularization in our well-established xenograft model of hindlimb ischemia. The MSC/VEGF cell product performed significantly better than MSC alone in these tests.

MSC/VEGF were tested by IV administration, in comparison to sham transplantation. Mice were tested six months after injection. MSC/VEGF were found to be safe, with no tumors or aberrant pathology observed in the tissues of transplanted mice, as assessed by GLP studies and a licensed pathologist. Four additional cohorts of NSG mice will be transplanted with the VEGF-$A_{165}$-modified MSC to validate the safety of the gene-modified human MSCs. Tissue harvest will be performed and detailed biosafety assessments will be done using established techniques. Standard toxicology studies will be completed at the level of GLP with tissue analyses completed by board certified pathologists.

GLP lots of allogeneic donor MSCs created using the GMP-grade vector are stable and effective in potency tests. No toxicity has been observed in high dose injections of MSC/VEGF. MSC transduced with other vectors for out to 18 months were tested in decade-long biosafety studies, and have not observed adverse events, tumorigenesis due to insertional mutagenesis, or toxicity.

The cell dose chosen for the toxicology studies represents 10 times the maximal dose to be administered in the human study, as corrected for animal weight. In the clinical trial the maximum cell dose that is administered to the patient is $15 \times 10^7$ cells. Since the average weight of an adult male patient is approximately 70 kg, the corresponding cell dose was calculated for the mouse. When scaling from mouse to human, $15 \times 10^7$ MSCs administered to a 70 kg adult male would be equivalent to 64,286 MSCs administered to a 30 g mouse. A dose of 640,286 MSCs would thus represent 10 times the maximum cell number that we propose to administer in the highest dose escalation step of the planned trial.

Using the smaller test lots of MSC and MSC/VEGF manufactured for IND-enabling studies, 750,000 human cells are administered per limb, over 10× the corresponding clinical dose as described above, in the established immune deficient mouse model of hindlimb ischemia.

Administration of MSC/VEGF in Hindlimb Ischemia Mouse Model

To test a mouse model, four groups of 15 mice are each analyzed under GLP conditions. First, femoral artery ligation is performed in 15 NOD/SCID/β-2-microglobulin-deficient mice to induce right hind limb ischemia. Laser Doppler Imaging (LDPI) is used to quantitate the reduction in hind limb blood flow immediately following surgery. Recovery from ischemia is quantified by the ratio of blood flow in the ischemic vs. the contralateral (unligated) limb, as shown in FIG. 10.

24 hours post-ligation mice are tail vein injected with PBS (n=5), 750,000 MSC (n=5), or 750,000 MSC/VEGF (n=5). Laser Doppler Perfusion Imaging (LDPI) is performed every three days to quantitate recovery of blood flow to ischemic limb over 4 weeks in transplanted mice versus sham-transplanted controls. The ratio of blood flow in the healthy vs. affected leg of each mouse is assessed, with standardized temperature, food, lighting, bedding, handling and other conditions between the four different groups of mice. This allows the best comparison from group to group under GLP conditions.

At 4 weeks, mice are euthanized and tissues prepared for toxicology and cell retention assays. Vascularization of ischemic versus contralateral muscle is quantitated by capillary density using H+E with CD31 immunostaining (capillary density/mm$^2$). Human cell recruitment to ischemic muscle is quantitated on slides by immunohistochemical analysis, as described. Tissues from each mouse are prepared for toxicology under GLP. All major organs are embedded in OCT medium for cryosectioning. Every 10th section (10 um thickness) is collected and stained with H&E. Stained slides are analyzed under light microscopy by a pathologist who is blinded to the treatment conditions. If any abnormal tissues are noted, fluorescence in situ hybridization (FISH) or polymerase chain reaction (PCR) is performed to determine whether the cells were of human or murine origin, as described in the art.

A lot of VEGF lentiviral vector supernatant has been generated. Scaled-up cultures of certified HEK-293T cells are transfected with a three plasmid lentiviral vector packaging system. 48 hours post-transfection, vector particles are collected and concentrated by spin filtration. After concentration, the GMP grade lentiviral vector is aliquoted and cryopreserved under GMP conditions. Aliquots are tested for sterility, endotoxin, mycoplasma, replication competent lentivirus and transducing titer using q-PCR. With this system, transducing titers in the high 10e9 to 10e10 range are usually obtained. Lentiviral vector stored in the GMP facility can be tested for stability on a yearly basis. In certain embodiments, the viral titer obtained is at least about 10e4, 10e5, 10e6, 10e7, 10e8, 10e9, 10e10, 10e11, 10e12, 10e13, or 10e14. The viral lots are screened to ensure that they meet acceptable criteria for titer, endotoxin, sequence, sterility, and helper assay Donor testing is performed to the same standards as required for human bone marrow donors. Tests include Human Immunodeficiency Virus (HIV) 1 and 2, Hepatitis B, Hepatitis C, Cytomegalovirus (CMV), Syphilis, Human T-lymphotropic virus (HTLV) type 1 and type 2 and West Nile Virus. Qualified donors are negative for these human transmissible diseases. HLA typing is not required for human MSC transplantation since the cells are immune privileged.

The clinical product is a human cellular product, and is an adult stem cell product. The clinical product is highly tested allogeneic human bone marrow-derived mesenchymal stem cells, transduced by the VEGF lentiviral vector (pCCLc-TRE-VEGF-PGK-rtTA-P2A-TK), expanded under strict adherence to Standard Operating Procedures (SOP) in place.

Process for Producing MSC/VEGF

The process comprises 7 phases: 1. Receipt of donor bone marrow. 2. Direct plating and expansion of the adherent cell layer. 3. Split into MSC (10%) and MSC/VEGF (90%) lots at first passage. Transduction of MSC/VEGF lot. 4. Expansion of both lots, using spatial and temporal separation. 5. Harvesting of the expanded, adherent cell layer. 6. Qualification, labeling, freezing and storage of the transplantable, final products. 7. Generation of Certificates of Analysis (COA) for the final products.

The vectors and MSC are tested for sterility, endotoxin, mycoplasma, identity, sequence of transferred genes (DNA sequencing), and contaminating DNA (VSV-g DNA PCR). Acceptable lots meet sterility requirements of 14 days without an organism seen, LAL endotoxin level below acceptable limit, mycoplasma not detected by PCR, RCL not detected by HIV-1 p24 from transduction culture of susceptible cell lines and primary target cells, sequence of transferred gene identical to expected sequence, contaminating DNA within acceptable limits. Additionally, the MSC are also tested for viability by dye exclusion. Acceptable MSC, in addition to the guidelines listed above, exhibit viability greater than 70%.

Flow cytometry is performed to access the MSC phenotype (CD105+/73+/90+). MSC lots are greater than 95% CD105+/73+/90+ and greater than 99% negative for CD45.

Lots are further evaluated for integration site analysis by Performance of linear amplification mediated (LAM) PCR, transduction efficiency by quantitative PCR, copy number of vector integrants per human cell genome, and karyotypic stability. MSC lots are also tested in vivo for their ability to restore blood flow after IM injection in immune deficient mouse hindlimb ischemia assay The clinical product, transduced, expanded and highly tested MSC/VEGF and non-transduced MSC controls from the same donor is administered at increasing doses to the affected limb of individual patients in each arm of the study. A volume of 200 µl per injection site×20 injections=4 ccs with 50, 100, or 150 million MSCs resuspended in plasma-lyte A for injection is administered.

Example 3

Human Mesenchymal Stem Cell/Marrow Stromal Cell (MSC) Expansion and Transduction The following exemplifies a protocol for MSC expansion and transduction.

Reagents include: Fetal Bovine Serum (heat inactivated @ 56° C. for 30 mins.) screened and certified lot from FDA-approved vendor (BSE, virus, bacteria, and endotoxin free); Dulbecco's Modified Eagle Media (DMEM), store at 2-8° C., protect from light; Dulbecco's Phosphate Buffered Saline (without calcium or magnesium) (DPBS), store @ 15-30° C., Sterile for cell culture; Recombinant Trypsin (animal component-free); Trypan Blue, 0.5% in 100 ml saline. Store at room temperature in small aliquot.; 100X (200 mM) L-Glutamine or GlutaMAX store at 2-8° C.; Ficoll-Paque at room temperature; 70% Ethanol; and 10% Bleach.

Supplies and equipment include: 15 ml sterile conical centrifuge tubes; 50 ml sterile conical centrifuge tubes; Serological pipettes, sterile, individually wrapped: 1 ml, 2 ml, 5 ml, 10 ml, 25 ml; 2 ml cryovials; 75 cm$^2$ (T 75) Tissue culture flasks with filter caps; 225 cm$^2$ (T 225) Tissue culture flasks with filter caps; 0.22 µm Bottle-top filter flasks, 500 ml; 1 ml microcentrifuge tubes; Hemacytometer; 20 µl Pipettor; Pipette tips for 20 µl pipettor; Inverted Microscope; Centrifuge with GS-6R Rotor; 37° C., 5% $CO_2$ Incubator.

Dexter's Original Medium for Stromal cells/MSC (DOM) includes: 350 ml Iscove's Modified Dulbecco's Medium (IMDM); 75 ml heat-inactivated (HI) horse serum*; 75 ml HI Fetal calf serum*; 5 ml L-glutamine (200 mM stock); 2.5 ml Pen/Strep (stock=10,000 U/ml penicillin and 10,000 µg/ml streptomycin); 500 µl 2-ME ($10^{-1}$ M stock); and 500 µl hydrocortisone ($10^{-3}$ M stock).

Dulbecco's Modified Eagles medium with 10% fetal calf serum and high glucose (D10HG) includes: 450 ml Dulbecco's Modified Eagles medium with high glucose; 50 ml heat-inactivated (HI) Fetal calf serum*; 5 ml L-glutamine (200 mM stock) and 2.5 ml Pen/Strep (stock=10,000 U/ml penicillin and 10,000 µl g/ml streptomycin).

Methods: Obtaining and plating human bone marrow-derived (MSC) cells: Marrow Filtration Screens: Normal human bone marrow cells were obtained from screens used to filter marrow during harvest of allogeneic donors. (see Note-1); The cells from one harvest screen, from a normal donor, can be split between 4/T-75 vent-cap flasks, in 15 mls of stromal medium (see Materials) per flask. The cells are then expanded, as described below. Filter vent-cap flasks are used for long-term culture. (see Note-2), Many transplant programs are now using G-CSF mobilized peripheral blood as a stem cell source in lieu of bone marrow. Unfortunately, MSC are not found in appreciable levels in G-CSF mobilized blood. The use of newer mobilization agents, such as the CXCR4 antagonist AMD3100 are alternatives.

Whole aspirated bone marrow can be used as a source of mesenchymal stem cells. Spicules from unseparated BM will be present in the aspirate, and can be collected by gravity sedimentation. The liquid marrow is then removed to another tube for additional processing. The spicules from a 10 ml aspirate should then be plated in T-75 vent-cap flasks in 15 mls of stromal medium (Dexter's original medium=DOM). If the BM sample must be ficolled for other studies, and the MSC investigator is salvaging spicules, use the techniques described in the section below.

Spicules from RBC pellet of ficoll layer in marrow aspirate processing. The ficolled "buffy coat" is not a rich source of MSC, but is what many investigators have to work with. The MSC are far more rare in the aspirated marrow fraction than in spicules from the harvest screens. They are even rarer if the sample is first ficolled (approximately $1\times10^6$/ml in the "buffy coat" or mononuclear fraction). If whole marrow aspirates are to be used, an optimal strategy is to use the mononuclear fraction, and also to recover the spicules from the bottom of the 50 ml ficoll tubes, since the small pieces of bone will fall through the density gradient.

For ficolling, first mix an equal volume of whole marrow and PBS, and then gently layer 25 mls over an equal volume of ficoll-paque in a 50 ml conical tube. Centrifuge the cells at 2000 rpm (1000 g) for 15 minutes. Once approximately 15 mls of the serum layer has been removed and discarded, buffy coat cells can be collected in another 10-15 mls, washed, and plated as described below. This leaves 5-10 mls of packed red blood cells and bony spicules in the bottom of the tube. PBS should then be added up to a volume of 50 mls. Allow the tubes to settle upright for 3 minutes, without centrifugation. Remove 40 mls PBS and RBC, then repeat the washing step: add PBS, let the spicules settle out, and remove RBC/PBS down to the final 10 mls. At this point, the red blood cells are sufficiently diluted out to allow plating of the spicules. Add another 40 mls PBS, centrifuge (1000 rpm, 250 g), remove fluid down to the last ml, and plate as described below.

Expanding human MSC: Plating MSC (initial seeding). To expand mesenchymal stem cells from total (RBC lysed) or ficolled marrow, cells prepared in DOM or D10HG are plated at a concentration of $5\times10^6$ mononuclear cells per ml in 75 cm$^2$ flasks, in 15-20 mls total volume at 37° C. with 5% $CO_2$. Spicules obtained from one harvest screen should be divided between four T-75 flasks containing 15 mls of DOM or D10HG each. Spicules obtained from the RBC pellet resulting from 10-15 mls of ficolled marrow can be plated in one T-75 flask, in 15 mls of medium. Cells are then expanded and transduced as described below.

MSC expansion. The MSC are allowed to adhere to the flasks overnight. The next morning, non-adherent cells can be gently flushed from the flasks and replated in a second flask, in the same medium. The initial flask is refed fresh medium. (DOM or D10HG) MSC colonies begin to develop as the cells expand out of the marrow spicules (FIG. 19). There are many other cells in the culture at this point. However, as the MSC grow and expand, the other cells differentiate out and/or can be removed. When the mesenchymal stem cells reach 70-80% confluency (70-80% of the plastic flask surface covered, FIG. 20), split them by trypsinization. Remove the medium from the flask, and discard. Rinse the flask with 15 mls 1×PBS and discard. Add 2 mls trypsin/EDTA solution, and tip the flask back and forth gently, to completely coat the adherent layer. Remove excess trypsin, leaving approximately 500 µls in the flask. Incubate for 10-15 minutes at 37° C. Pick up the flask and turn it to coat all surfaces every 3-4 minutes during the trypsinization process. If the mesenchymal stem cells were healthy and subconfluent prior to trypsinization, a single cell suspension will result. To neutralize the trypsin, resuspend the cells from each flask in 45 mls DOM or other serum-containing medium. Transfer 15 mls each to three new flasks. Discard the original flask, which will contain firmly adherent macrophages. Grow the mesenchymal stem cells until they reach 80% confluency, once again. Repeat steps 4-6. Grow up and repeat, to generate a "passage 3" layer. The monolayer should be a smooth, homogeneous mesenchymal stem cell population. The cells will be rather "chunky", not spindle shaped as will happen in straight FCS without the addition of horse serum. Alternately, the cells can be collected using an EDTA-based cell dissociation buffer (rather than trypsin, which cleaves away many cell surface proteins), and then a FACS-based depletion can be done to remove CD45+ cells, including CD14+ monocyte/macrophages, from the developing MSC monolayer. It is best to use trypsinization (trypsin-EDTA), to dissociate sub-confluent monolayers of primary mesenchymal stem cells from the flask. When the mesenchymal stem monolayer has the correct appearance (FIG. 20), collect the cells from one 80% confluent flask containing passage 3-6 mesenchymal stem cells by trypsinization. Re-plate each flask so that it is split 1:6 for viral supernatant addition, as described in the sections below.

MSC transduction using retroviral and lentiviral vectors: For retroviral transduction, add supernatant from MoMuLV-based retroviral vectors with protamine sulfate (final concentration=4 μg/ml) four times, over a 48 hour period. Add it only once every 24 hours, or it will be toxic. This should result in 20-40% of the flask being transduced, due to the rapid division of the MSC. For lentiviral transduction, VSV-G pseudotyped lentiviral vector supernatant can be added once or twice at an MOI of 10-100, without the need for protamine sulfate. Select the cells according to the selectable marker included in the chosen vector (if using G418 to select for the neo gene, the best concentration is 0.75 mg/ml active drug), or use as partially-transduced monolayers. Transduced MSC are excellent vehicles from which to secrete proteins.

The screens used to filter marrow during harvest are the richest source of mesenchymal stem cells. Many small bony spicules packed with stroma (as well as hematopoietic stem and progenitor cells) will get lodged in the screen, and can be easily removed by flushing. Filter vent-cap flasks are used for long-term culture, despite their greater cost as compared to standard screw-caps, because the risks for air-borne fungal spore contamination are high for cultures which can be grown for 1-2 months. The tightly closed, gas permeable filter vent caps reduce the risk of cross-contamination between flasks. It is advisable to perform at least one red cell lysis and wash before plating, if using this method. The washing technique is described in section 2.3. DOM is the richest medium and rapidly forces contaminating hematopoietic cells into erythroid and monocytic differentiation. A simpler medium can also be used, as described in section 3. If the aspirate providing the spicules is larger, the number of flasks should be scaled up accordingly. 12-24 hours after plating, remove the nonadherent fraction, which contains primarily hematopoietic cells. Flush the adherent layer with PBS to remove as many hematopoietic cells as possible, and add the flushings to the collected nonadherent cell fraction. The nonadherent hematopoietic cells can be cryopreserved for later use if desired: the spicules are a rich source of hematopoietic, as well as mesenchymal stem cells. Refeed each adherent layer 15 mls of DOM (reagents section), for expansion of mesenchymal stem cells. DOM is the richest medium for MSC expansion without differentiation, and the horse serum rapidly forces contaminating hematopoietic cells into erythroid and monocytic differentiation, so that hematopoietic stem cells will not contaminate the stromal layer after 3 passages. A minimal medium, D10HG, which contains only fetal calf serum (Table 1B), can also be used, but hematopoietic stem cells will survive happily on the stromal layer in this medium. MSC have not yet been expanded efficiently without the use of fetal calf serum, and it is imperative to screen the serum for optimal MSC growth without differentiation, when using either medium. In the fetal calf/horse serum mixture (DOM), the developing erythroid cells become non-adherent and are easily flushed away as the MSC layer develops and is expanded. Alternately, a depletion step can be done at passage 2-3, to remove Glycophorin A+ cells. Early monocytes can also be removed by flushing, but mature macrophages are tightly adherent to the tissue culture flask and cannot be removed, even with trypsin. Therefore, the MSC can be taken to a new flask, while leaving the macrophages behind to be discarded. Mesenchymal stem cells will be readily trypsinized if they are in subconfluent monolayers. If they are allowed to become confluent, they form a 3-dimensional tissue with excessive buildup of collagen and other extracellular matrix molecules between the layers of cells. The collagen layers are harder for the trypsin to digest than the adhesion foci with which the cells adhere to the plastic flask. The result is a useless sheet, or large chunks, of cells which will quickly deplete nutrients from the medium, and will necrose in the center. If the monolayer has numerous phase-bright macrophage contaminants, perform a CD45+ cell depletion using magnetic beads or FACS, or repeat steps 4-6. The resultant monolayer will be completely CD45-negative, due to the loss of hematopoietic cells. No phase-bright cells will be seen adhering to the MSC monolayer (FIG. 20). It is imperative that the MSC not become confluent during the transduction procedure, but will remain in rapid growth. Contact inhibition in adherent cells, such as MSC, increases intracellular levels of the CDK inhibitor p27, which halts cell cycle. Target cells must traverse cell cycle to allow integration of retroviral vectors, and must be at least metabolically active for effective lentiviral vector transduction and integration. MSCs is not usually transduced or used for other studies until passage #3 or 4. At this point (FIG. 20), most hematopoietic cells will have been eliminated, except for mature macrophages which typically will comprise less than 1% of the culture. The cells also should be used for transduction, experiments, or transplantation between passage 3-6. By passage ten, they can begin to differentiate and become senescent. Since the primary MSC cultures are not immortalized, they do have a finite lifespan, and by later passages, they begin to slow down in growth and to become larger and more differentiated. Protamine sulfate is a polycationic compound which neutralizes the negatively charged retroviral particles and cell surfaces. While the methodologies for transducing MSC are relatively simple—since in log phase the cells are rapidly dividing and incorporate vector very easily, in comparison to hematopoietic stem cells. The cells should be subconfluent when each aliquot of supernatant is added. Confluent cells are contact inhibited and will not divide to allow retroviral vector integration. Although lentiviral vectors can enter non-dividing cells, MSC monolayers should still be subconfluent prior to transduction, or the VSV-G envelope can cause cell fusion, resulting in multinucleate cells which appear overnight in the culture. Also, MSC can and do "share" proteins with neighboring cells, through junction formation or other as-yet-unknown mechanisms. For this reason, Applicants recommend that MSC (marrow stromal cells) be plated at subconfluency for selective agents such as G418 to work effectively. This is also reflected in the fact that fluorescent markers such as eGFP can be shared between cells. Transduced cells dropped into a confluent plate of non-transduced MSC can cause a green "halo" to be seen in neighboring cells, although it is not as bright in intensity as seen in the cell that is expressing the transgene.

Expanded Marrow Stromal Cells/Mesenchymal Stem Cells (MSCs) from human bone marrow will have the phenotype CD34−/CD45−/CD105+/CD90+/CD73+, as shown in FIG. 21.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

REFERENCES

1. T. Meyerrose et al., *Establishment and transduction of primary human stromal/mesenchymal stem cell monolayers*. J. Nolta, Ed., Genetic Engineering of Mesenchymal Stem Cells (Kluwer Academic Publishers, Dordrecht, the Netherlands, 2006), vol. Chapter 2.
2. I. Rosova, M. Dao, B. Capoccia, D. Link, J. A. Nolta, *Stem Cells* 26, 2173 (August 2008).
3. I. Rosova, D. Link, J. A. Nolta, *Tissue Eng Part A* 16, 2627 (August 2010).
4. D. W. Losordo, S. Dimmeler, *Circulation* 109, 2487 (Jun. 1, 2004).
5. B. J. Capoccia et al., *Blood* 113, 5340 (May 21, 2009).
6. C. S. Sondergaard et al., *J Transl Med* 8, 24 (2010).
7. D. W. Losordo, S. Dimmeler, *Circulation* 109, 2692 (Jun. 8, 2004).
8. Y. H. Kusumanto, G. A. Hospers, N. H. Mulder, R. A. Tio, *Int J Cardiovasc Intervent* 5, 27 (2003).
9. E. Benoit et al., *J Transl Med* 9, 165 (Sep. 27, 2011).
10. G. P. Lasala, J. J. Minguell, *Br Med Bull* 98, 187 (2011).
11. H. Lawall, P. Bramlage, B. Amann, *J Vasc Surg* 53, 445 (February, 2011).
12. T. Kinnaird et al., *Circulation* 109, 1543 (Mar. 30, 2004).
13. F. A. Fierro, S. Kalomoiris, C. S. Sondergaard, J. A. Nolta, *Stem Cells*, (Sep. 2, 2011).
14. G. Annett, S. Olson, L. Wirthlin, G. Bauer, J. A. Nolta, *Future Medicine*, (2010).
15. A. I. Caplan, J. E. Dennis, *J Cell Biochem* 98, 1076 (Aug. 1, 2006).
16. H. K. Salem, C. Thiemermann, *Stem Cells* 28, 585 (March 31).
17. W. A. Noort et al., *Panminerva medica* 52, 27 (March).
18. J. Tolar, K. Le Blanc, A. Keating, B. R. Blazar, *Stem Cells* 28, 1446 (August).
19. T. T. Rissanen, J. Rutanen, S. Yla-Herttuala, *Adv Genet* 52, 117 (2004).
20. M. L. George, S. A. Eccles, M. G. Tutton, A. M. Abulafi, R. I. Swift, *Clin Cancer Res* 6, 3147 (August, 2000).
21. T. Meyerrose et al., *Advanced drug delivery reviews* 62, 1167 (Sep. 30, 2010).
22. J. Nolta, *Genetic Engineering of Mesenchymal Stem Cells*. (Kluwer, 2006).
23. M. S. Penn et al., *Circulation research*, (Nov. 3, 2011).
24. J. M. Hare et al., *Journal of the American College of Cardiology* 54, 2277 (Dec. 8, 2009).
25. T. Meyerrose et al., *Stem Cells* 25, 220 (January, 2007).
26. A. Arthur, A. Zannettino, S. Gronthos, *J Cell Physiol* 218, 237 (February, 2009).
27. M. Gnecchi, L. G. Melo, *Methods in molecular biology* (Clifton, N.J. 482, 281 (2009).
28. N. K. Satija et al., *J Cell Mol Med* 13, 4385 (November-December, 2009).
29. G. Bauer et al., *Mol Ther* 16, 1308 (July, 2008).
30. K. Le Blanc, *Cytotherapy* 8, 559 (2006).
31. C. A. Gregory, J. Ylostalo, D. J. Prockop, *Sci STKE* 2005, pe37 (Jul. 26, 2005).
32. N. F. Huang, S. Li, *Regenerative medicine* 3, 877 (November, 2008).
33. K. Kurpinski, J. Chu, D. Wang, S. Li, *Cellular and molecular bioengineering* 2, 606 (December, 2009).
34. T. E. Meyerrose et al., *Stem Cells* 26, 1713 (July, 2008).
35. M. A. Dao, K. A. Pepper, J. A. Nolta, *Stem Cells* 15, 443 (1997).
36. J. A. Nolta, M. A. Dao, S. Wells, E. M. Smogorzewska, D. B. Kohn, *Proc Natl Acad Sci USA* 93, 2414 (Mar. 19, 1996).
37. J. A. Nolta, D. B. Kohn, *Hum Gene Ther* 1, 257 (Fall, 1990).
38. E. Tsark, M. Dao, X. Wang, K. Weinberg, J. Nolta, *J Immunol* 166, 170 (2001).
39. X. Wang et al., *Blood* 101 (10) 4201 (Jan. 30, 2003).
40. J. A. Nolta, M. B. Hanley, D. B. Kohn, *Blood* 83, 3041 (May 15, 1994).
41. K. G. Shyu, H. Chang, B. W. Wang, P. Kuan, *Am J Med* 114, 85 (Feb. 1, 2003).
42. L. K. Aguilar, B. W. Guzik, E. Aguilar-Cordova, *J Cell Biochem* 112, 1969 (August, 2011).
43. B. Nervi et al., *Exp Hematol* 35, 1823 (December, 2007).
44. B. Nervi et al., *Molecular Therapy* 9, 259 (2004).
45. M. Blumenthal et al., *Mol Ther* 15, 183 (January, 2007).
46. Y. Wang et al., *J Mol Cell Cardiol* 40, 736 (May, 2006).
47. F. Gao et al., *Can J Cardiol* 23, 891 (September, 2007).
48. R. Matsumoto et al., *Arterioscler Thromb Vasc Biol* 25, 1168 (June, 2005).
49. T. Deuse et al., *Circulation* 120, 5247 (Sep. 15, 2009).
50. T. S. Stappenbeck, H. Miyoshi, *Science* 324, 1666 (Jun. 26, 2009).
51. B. Parekkadan et al., *PLoS One* 2, e941 (2007).
52. H. Song et al., *Mol Cells* 19, 402 (Jun. 30, 2005).
53. F. Yang et al., *Proc Natl Acad Sci USA* 107, 3317 (Feb. 23, 2010).
54. C. P. Hodgkinson, J. A. Gomez, M. Mirotsou, V. Dzau, *Hum Gene Ther*, (Sep. 8, 2010).
55. F. Ng et al., *Blood* 112, 295 (Jul. 15, 2008).
56. F. Fierro, S. Kalomoiris, C. Sondergaard, J. Nolta, *Stem Cells* in press, (2011).
57. S. G. Ball, C. A. Shuttleworth, C. M. Kielty, *J Cell Biol* 177, 489 (May 7, 2007).
58. D. J. Maxwell et al., *Stem Cells* 26, 517 (February, 2008).

59. A. E. Ting et al., *Critical reviews in oncology/hematology* 65, 81 (January, 2008).
60. R. W. Mays, W. van't Hof, A. E. Ting, R. Perry, R. Deans, *Expert opinion on biological therapy* 7, 173 (February, 2007).
61. R. E. Newman, D. Yoo, M. A. LeRoux, A. Danilkovitch-Miagkova, *Inflammation & allergy drug targets* 8, 110 (June, 2009).
62. G. W. Dryden, *Expert opinion on biological therapy* 9, 841 (July, 2009).
63. W. Gruenloh et al., *Tissue Eng Part A* 17, 1517 (June, 2011).
64. S. Pati et al., *Stem cells and development* 20, 89 (January, 2011).
65. S. S. Park et al., *Investigative ophthalmology & visual science*, (Jan. 12, 2012).
66. I. Rosová, D. Link, J. Nolta, in press, *Tissue Engineering*, (2010).
67. T. E. Meyerrose et al., *Stem Cells* 25, 220 (January, 2007).
68. L. Wirthlin, D. Hess, P. Zhou, J. Nolta, *Biol Blood Marrow Transplant* 14, 151 (January, 2008).
69. P. Zhou et al., *Methods in molecular biology* (Clifton, N.J. 430, 213 (2008).
70. *Eur J Vasc Endovasc Surg* 11, 112 (January, 1996).
71. K. English, B. P. Mahon, *J Cell Biochem* 112, 1963 (August, 2011).
72. M. D. Griffin, T. Ritter, B. P. Mahon, *Hum Gene Ther* 21, 1641 (December, 2010).
73. D. B. Kohn et al., *Nat Med* 4, 775 (July, 1998).
74. D. B. Kohn et al., *Nat Med* 1, 1017 (October, 1995).
75. S. Olson et al., *Molecular Neurobiology* In Press, (2011).
76. N. Joyce et al., *Regenerative medicine* 5, 933 (November, 2010).
77. M. Schmidt et al., *Nat Med* 9, 463 (April, 2003).
78. Gurtner G C, et al., *Nature* 2008; 453(7193): 314-21.
79. Stappenbeck T S, et al., *Science* 2009; 324(5935): 1666-9.
80. da Silva Meirelles L, et al., *J Cell Sci* 2006; 119(Pt 11): 2204-13.
81. Crisan M, et al., *Cell stem cell* 2008; 3(3): 301-13.
82. Sacchetti B, et al., *Cell* 2007; 131(2): 324-36.
83. Le Blanc K, et al., *Lancet* 2008; 371(9624): 1579-86.
84. Hare J M, et al., *Journal of the American College of Cardiology* 2009; 54(24): 2277-86.
85. Garcia-Olmo D, et al., *Dis Colon Rectum* 2009; 52(1): 79-86.
86. Caplan A I, et al., *J Cell Biochem* 2006; 98(5): 1076-84.
87. Aggarwal S, et al., *Blood* 2005; 105(4): 1815-22.
88. Kinnaird T, et al., *Circulation* 2004; 109(12): 1543-9.
89. Parekkadan B, et al., *PLoS One* 2007; 2(9): e941.
90. Song H, et al., *Mol Cells* 2005; 19(3): 402-7.
91. Yang F, et al., *Proc Natl Acad Sci USA* 2010; 107(8): 3317-22.
92. Hodgkinson C P, et al., *Hum Gene Ther* 2010.
93. Meyerrose T, et al., *Advanced drug delivery reviews* 2010; 62(12): 1167-74.
94. Ng F, et al., *Blood* 2008; 112(2): 295-307.
95. Meyerrose T, Rosova I, Dao M, Herrbrich P, Bauer G, Nolta J. *Establishment and transduction of primary human stromal/mesenchymal stem cell monolayers*, vol. Chapter 2. Kluwer Academic Publishers: Dordrecht, the Netherlands, 2006.
96. Crampton S P, et al., *J Vis Exp* 2007; (3): 183.
97. Baudin B, et al., *Nat Protoc* 2007; 2(3): 481-5.
98. Popova A P, et al., *Am J Physiol Lung Cell Mol Physiol* 2010; 298(6): L735-43.
99. Welldon K J, et al., *J Biomed Mater Res A* 2008; 84(3): 691-701.
100. Rich J T, et al., *Biochemical and biophysical research communications* 2008; 372(1): 230-5.
101. Narita Y, et al., *Cell Tissue Res* 2008; 333(3): 449-59.
102. Ugarte F, et al., *Exp Hematol* 2009; 37(7): 867-875 e1.
103. Gregory C A, et al., *Anal Biochem* 2004; 329(1): 77-84.
104. Greenspan P, et al., *J Cell Biol* 1985; 100(3): 965-73.
105. Geback T, et al., *Biotechniques* 2009; 46(4): 265-74.
106. Rosova I, et al., *Stem Cells* 2008; 26(8): 2173-82.
107. Capoccia B J, et al., *Blood* 2009; 113(21): 5340-51.
108. Rosová I, Link D, Nolta J. Small Interfering RNA-Mediated Decreases in c-Met Levels Affect the Differentiation Potential of Human Mesenchymal Stem Cells and Reduce Their Capacity for Tissue Repair. in press, tissue Engineering 2010.
109. Ball S G, et al., *J Cell Biol* 2007; 177(3): 489-500.
110. Annes J P, et al., *J Cell Sci* 2003; 116(Pt 2): 217-24.
111. Janssens K, et al., *Endocr Rev* 2005; 26(6): 743-74.
112. Hirschi K K, et al., *Ann N Y Acad Sci* 2002; 961: 223-42.
113. Hirschi K K, et al., *J Cell Biol* 1998; 141(3): 805-14.
114. Heng B C, et al., *Stem Cells* 2004; 22(7): 1152-67.
115. Mackay A M, et al., Tissue Eng 1998; 4(4): 415-28.
116. Solchaga L A, et al., *J Cell Physiol* 2005; 203(2): 398-409.
117. Kratchmarova I, et al., *Science* 2005; 308(5727): 1472-7.
118. Schmierer B, et al., *Nat Rev Mol Cell Biol* 2007; 8(12): 970-82.
119. Chaudhary L R, et al., *J Cell Biochem* 2001; 81(2): 304-11.
120. Xiao G, et al., *J Biol Chem* 2000; 275(6): 4453-9.
121. Wang X, et al., *Am J Physiol Heart Circ Physiol* 2006; 290(4): H1393-405.
122. Matsumoto R, et al., *Arterioscler Thromb Vasc Biol* 2005; 25(6): 1168-73.
123. Gao F, et al., *Can J Cardiol* 2007; 23(11): 891-8.
124. Lawall H, et al., *Thromb Haemost* 2010; 103(4): 696-709.
125. Lawall H, et al., *J Vasc Surg* 2011; 53(2): 445-53.
126. Mulder G, et al., *Wound Repair Regen* 2009; 17(6): 772-9.
127. Bauer G, et al., *Mol Ther* 2008; 16(7): 1308-15.

```
                        Sequence Listing

SEQ ID NO: 1
4974                                                          GAATTCG
4981 CCCTTCCTGA GATCACCGGT AGGAGGGCCA TCATGAACTT TCTGCTGTCT TGGGTGCATT
5041 GGAGCCTTGC CTTGCTGCTC TACCTCCACC ATGCCAAGTG GTCCCAGGCT GCACCCATGG
5101 CAGAAGGAGG AGGGCAGAAT CATCACGAAG TGGTGAAGTT CATGGATGTC TATCAGCGCA
5161 GCTACTGCCA TCCAATCGAG ACCCTGGTGG ACATCTTCCA GGAGTACCCT GATGAGATCG
5221 AGTACATCTT CAAGCCATCC TGTGTGCCCC TGATGCGATG CGGGGCTGC TGCAATGACG
5281 AGGGCCTGGA GTGTGTGCCC ACTGAGGAGT CCAACATCAC CATGCAGATT ATGCGGATCA
5341 AACCTCACCA AGGCCAGCAC ATAGGAGAGA TGAGCTTCCT ACAGCACAAC AAATGTGAAT
```

```
5401 GCAGACCAAA GAAAGATAGA GCAAGACAAG AAAATCCCTG TGGGCCTTGC TCAGAGCGGA
5461 GAAAGCATTT GTTTGTACAA GATCCGCAGA CGTGTAAATG TTCCTGCAAA AACACAGACT
5521 CGCGTTGCAA GGCGAGGCAG CTTGAGTTAA ACGAACGTAC TTGCAGATGT GACAAGCCGA
5581 GGCGGTGAAA GGGCGAATTC

SEQ ID NO: 2
   1 CAGGTGGCAC TTTTCGGGGA AATGTGCGCG GAACCCCTAT TTGTTTATTT TTCTAAATAC
  61 ATTCAAATAT GTATCCGCTC ATGAGACAAT AACCCTGATA AATGCTTCAA TAATATTGAA
 121 AAAGGAAGAG TATGAGTATT CAACATTTCC GTGTCGCCCT TATTCCCTTT TTTGCGGCAT
 181 TTTGCCTTCC TGTTTTTGCT CACCCAGAAA CGCTGGTGAA AGTAAAAGAT GCTGAAGATC
 241 AGTTGGGTGC ACGAGTGGGT TACATCGAAC TGGATCTCAA CAGCGGTAAG ATCCTTGAGA
 301 GTTTTCGCCC CGAAGAACGT TTTCCAATGA TGAGCACTTT TAAAGTTCTG CTATGTGGCG
 361 CGGTATTATC CCGTATTGAC GCCGGGCAAG AGCAACTCGG TCGCCGCATA CACTATTCTC
 421 AGAATGACTT GGTTGAGTAC TCACCAGTCA CAGAAAAGCA TCTTACGGAT GGCATGACAG
 481 TAAGAGAATT ATGCAGTGCT GCCATAACCA TGAGTGATAA CACTGCGGCC AACTTACTTC
 541 TGACAACGAT CGGAGGACCG AAGGAGCTAA CCGCTTTTTT GCACAACATG GGGGATCATG
 601 TAACTCGCCT TGATCGTTGG GAACCGGAGC TGAATGAAGC CATACCAAAC GACGAGCGTG
 661 ACACCACGAT GCCTGTAGCA ATGGCAACAA CGTTGCGCAA ACTATTAACT GGCGAACTAC
 721 TTACTCTAGC TTCCCGGCAA CAATTAATAG ACTGGATGGA GGCGGATAAA GTTGCAGGAC
 781 CACTTCTGCG CTCGGCCCTT CCGGCTGGCT GGTTTATTGC TGATAAATCT GGAGCCGGTG
 841 AGCGTGGGTC TCGCGGTATC ATTGCAGCAC TGGGGCCAGA TGGTAAGCCC TCCCGTATCG
 901 TAGTTATCTA CACGACGGGG AGTCAGGCA CTATGGATGA ACGAAATAGA CAGATCGCTG
 961 AGATAGGTGC CTCACTGATT AAGCATTGGT AACTGTCAGA CCAAGTTTAC TCATATATAC
1021 TTTAGATTGA TTTAAAACTT CATTTTTAAT TTAAAAGGAT CTAGGTGAAG ATCCTTTTTG
1081 ATAATCTCAT GACCAAAATC CCTTAACGTG AGTTTTCGTT CCACTGAGCG TCAGACCCCG
1141 TAGAAAAGAT CAAAGGATCT TCTTGAGATC CTTTTTTTCT GCGCGTAATC TGCTGCTTGC
1201 AAACAAAAAA ACCACCGCTA CCAGCGGTGG TTTGTTTGCC GGATCAAGAG CTACCAACTC
1261 TTTTTCCGAA GGTAACTGGC TTCAGCAGAG CGCAGATACC AAATACTGTC CTTCTAGTGT
1321 AGCCGTAGTT AGGCCACCAC TTCAAGAACT CTGTAGCACC GCCTACATAC CTCGCTCTGC
1381 TAATCCTGTT ACCAGTGGCT GCTGCCAGTG GCGATAAGTC GTGTCTTACC GGGTTGGACT
1441 CAAGACGATA GTTACCGGAT AAGGCGCAGC GGTCGGGCTG AACGGGGGGT TCGTGCACAC
1501 AGCCCAGCTT GGAGCGAACG ACCTACACCG AACTGAGATA CCTACAGCGT GAGCTATGAG
1561 AAAGCGCCAC GCTTCCCGAA GGGAGAAAGG CGGACAGGTA TCCGGTAAGC GGCAGGGTCG
1621 GAACAGGAGA GCGCACGAGG GAGCTTCCAG GGGGAAACGC CTGGTATCTT TATAGTCCTG
1681 TCGGGTTTCG CCACCTCTGA CTTGAGCGTC GATTTTTGTG ATGCTCGTCA GGGGGGCGGA
1741 GCCTATGGAA AAACGCCAGC AACGCGGCCT TTTTACGGTT CCTGGCCTTT TGCTGGCCTT
1801 TTGCTCACAT GTTCTTTCCT GCGTTATCCC CTGATTCTGT GGATAACCGT ATTACCGCCT
1861 TTGAGTGAGC TGATACCGCT CGCCGCAGCC GAACGACCGA GCGCAGCGAG TCAGTGAGCG
1921 AGGAAGCGGA AGAGCGCCCA ATACGCAAAC CGCCTCTCCC CGCGCGTTGG CCGATTCATT
1981 AATGCAGCTG GCACGACAGG TTTCCCGACT GGAAAGCGGG CAGTGAGCGC AACGCAATTA
2041 ATGTGAGTTA GCTCACTCAT TAGGCACCCC AGGCTTTACA CTTTATGCTT CCGGCTCGTA
2101 TGTTGTGTGG AATTGTGAGC GGATAACAAT TTCACACAGG AAACAGCTAT GACCATGATT
2161 ACGCCAAGCG CGCAATTAAC CCTCACTAAA GGGAACAAAA GCTGGAGCTG CAAGCTTGGC
2221 CATTGCATAC GTTGTATCCA TATCATAATA TGTACATTTA TATTGGCTCA TGTCCAACAT
2281 TACCGCCATG TTGACATTGA TTATTGACTA GTTATTAATA GTAATCAATT ACGGGGTCAT
2341 TAGTTCATAG CCCATATATG GAGTTCCGCG TTACATAACT TACGGTAAAT GGCCCGCCTG
2401 GCTGACCGCC CAACGACCCC CGCCCATTGA CGTCAATAAT GACGTATGTT CCCATAGTAA
2461 CGCCAATAGG GACTTTCCAT TGACGTCAAT GGGTGGAGTA TTTACGGTAA ACTGCCCACT
2521 TGGCAGTACA TCAAGTGTAT CATATGCCAA GTACGCCCCC TATTGACGTC AATGACGGTA
2581 AATGGCCCGC CTGGCATTAT GCCCAGTACA TGACCTTATG GACTTTCCT ACTTGGCAGT
2641 ACATCTACGT ATTAGTCATC GCTATTACCA TGGTGATGCG GTTTTGGCAG TACATCAATG
2701 GGCGTGGATA GCGGTTTGAC TCACGGGGAT TTCCAAGTCT CCACCCCATT GACGTCAATG
2761 GGAGTTTGTT TTGGCACCAA AATCAACGGG ACTTTCCAAA ATGTCGTAAC AACTCCGCCC
2821 CATTGACGCA AATGGGCGGT AGGCGTGTAC GGTGGGAGGT CTATATAAGC AGAGCTCGTT
2881 TAGTGAACCG GGTCTCTCT GGTTAGACCA GATCTGAGCC TGGGAGCTCT CTGGCTAACT
2941 AGGGAACCCA CTGCTTAAGC CTCAATAAAG CTTGCCTTGA GTGCTTCAAG TAGTGTGTGC
3001 CCGTCTGTTG TGTGACTCTG GTAACTAGAG ATCCCTCAGA CCCTTTTAGT CAGTGTGGAA
3061 AATCTCTAGC AGTGGCGCCC GAACAGGGAC CTGAAAGCGA AAGGGAAACC AGAGGAGCTC
3121 TCTCGACGCA GGACTCGGCT TGCTGAAGCG CGCACGGCAA GAGGCGAGGG GCGGCGACTG
3181 GTGAGTACGC CAAAAATTTT GACTAGCGGA GGCTAGAAGG AGAGAGATGG GTGCGAGAGC
3241 GTCAGTATTA AGCGGGGGAG AATTAGATCG CGATGGGAAA AAATTCGGTT AAGGCCAGGG
3301 GGAAAGAAAA AATATAAATT AAAACATATA GTATGGGCAA GCAGGGAGCT AGAACGATTC
3361 GCAGTTAATC CTGGCCTGTT AGAAACATCA GAAGGCTGTA GACAAATACT GGGACAGCTA
3421 CAACCATCCC TTCAGACAGG ATCAGAAGAA CTTAGATCAT TATATAATAC AGTAGCAACC
3481 CTCTATTGTG TGCATCAAAG GATAGAGATA AAAGACACCA AGGAAGCTTT AGACAAGATA
3541 GAGGAAGAGC AAAACAAAAG TAAGACCACC GCACAGCAAG CGGCCGCTGA TCTTCAGACC
3601 TGGAGGAGGA GATATGAGGG ACAATTGGAG AAGTGAATTA TATAAATATA AAGTAGTAAA
3661 AATTGAACCA TTAGGAGTAG CACCCACCAA GGCAAAGAGA AGAGTGGTGC AGAGAGAAAA
3721 AAGAGCAGTG GGAATAGGAG CTTTGTTCCT TGGGTTCTTG GGAGCAGCAG GAAGCACTAT
3781 GGGCGCAGCC TCAATGACGC TGACGGTACA GGCCAGACAA TTATTGTCTG GTATAGTGCA
3841 GCAGCAGAAC AATTTGCTGA GGGCTATTGA GGCGCAACAG CATCTGTTGC AACTCACAGT
3901 CTGGGGCATC AAGCAGCTCC AGGCAAGAAT CCTGGCTGTG GAAAGATACC TAAAGGATCA
3961 ACAGCTCCTG GGGATTTGGG GTTGCTCTGG AAAACTCATT TGCACCACTG CTGTGCCTTG
4021 GAATGCTAGT TGGAGTAATA AATCTCTGGA ACAGATTGGA ATCACACGAC CTGGATGGAG
4081 TGGGACAGAG AAATTAACAA TTACACAAGC TTAATACACT CCTTAATTGA AGAATCGCAA
4141 AACCAGCAAG AAAAGAATGA ACAAGAATTA TTGGAATTAG ATAAATGGGC AAGTTTGTGG
4201 AATTGGTTTA ACATAACAAA TTGGCTGTGG TATATAAAAT TATTCATAAT GATAGTAGGA
```

-continued

Sequence Listing

```
4261 GGCTTGGTAG GTTTAAGAAT AGTTTTTGCT GTACTTTCTA TAGTGAATAG AGTTAGGCAG
4321 GGATATTCAC CATTATCGTT TCAGACCCAC CTCCCAACCC CGAGGGGACC CGACAGGCCC
4381 GAAGGAATAG AAGAAGAAGG TGGAGAGAGA GACAGAGACA GATCCATTCG ATTAGTGAAC
4441 GGATCTCGAC GGTATCGATC TCGACACAAA TGGCAGTATT CATCCACAAT TTTAAAAGAA
4501 AAGGGGGGAT TGGGGGGTAC AGTGCAGGGG AAAGAATAGT AGACATAATA GCAACAGACA
4561 TACAAACTAA AGAATTACAA AAACAAATTA CAAAAATTCA AAATTTTCGG GTTTATTACA
4621 GGGACAGCAG AGATCCAGTT TGGGTCGAGG ATTCGAGTTT ACTCCCTATC AGTGATAGAG
4681 AACGTATGTC GAGTTTACTC CCTATCAGTG ATAGAGAACG ATGTCGAGTT TACTCCCTAT
4741 CAGTGATAGA GAACGTATGT CGAGTTTACT CCCTATCAGT GATAGAGAAC GTATGTCGAG
4801 TTTACTCCCT ATCAGTGATA GAGAACGTAT GTCGAGTTTA TCCCTATCAG TGATAGAGAA
4861 CGTATGTCGA GTTTACTCCC TATCAGTGAT AGAGAACGTA TGTCGAGGTA GGCGTGTACG
4921 GTGGGAGGCC TATATAAGCA GAGCTCGTTT AGTGAACCGT CAGATCGCCT GGAGAATTCG
4981 CCCTTCCTGA GATCACCGGT AGGAGGGCCA TCATGAACTT TCTGCTGTCT TGGGTGCATT
5041 GGAGCCTTGC CTTGCTGCTC TACCTCCACC ATGCCAAGTG GTCCCAGGCT GCACCCATGG
5101 CAGAAGGAGG AGGGCAGAAT CATCACGAAG TGGTGAAGTT CATGGATGTC TATCAGCGCA
5161 GCTACTGCCA TCCAATCGAG ACCCTGGTGG ACATCTTCCA GGAGTACCCT GATGAGATCG
5221 AGTACATCTT CAAGCCATCC TGTGTGCCCC TGATGCGATG CGGGGCTGC TGCAATGACG
5281 AGGGCCTGGA GTGTGTGCCC ACTGAGGAGT CCAACATCAC CATGCAGATT ATGCGGATCA
5341 AACCTCACCA AGGCCAGCAC ATAGGAGAGA TGAGCTTCCT ACAGCACAAC AAATGTGAAT
5401 GCAGACCAAA GAAAGATAGA GCAAGACAAG AAAATCCCTG TGGGCCTTGC TCAGAGCGGA
5461 GAAAGCATTT GTTTGTACAA GATCCGCAGA CGTGTAAATG TTCCTGCAAA AACACAGACT
5521 CGCGTTGCAA GGCGAGGCAG CTTGAGTTAA ACGAACGTAC TTGCAGATGT GACAAGCCGA
5581 GGCGGTGAAA GGGCGAATTC TACCGGGTAG GGGAGGCGCT TTTCCCAAGG CAGTCTGGAG
5641 CATGCGCTTT AGCAGCCCCG CTGGCACTTG GCGCTACACA AGTGGCCTCT GGCCTCGCAC
5701 ACATTCCACA TCCACCGGTA GGCGCCAACC GGCTCCGTTC TTTGGTGGCC CCTTCGCGCC
5761 ACCTTCTACT CCTCCCCTAG TCAGGAAGTT CCCCCCCGCC CCGCAGCTCG CGTCGTGCAG
5821 GACGTGACAA ATGGAAGTAG CACGTCTCAC TAGTCTCGTG CAGATGGACA GCACCGCTGA
5881 GCAATGGAAG CGGGTAGGCC TTTGGGGCAG CGGCCAATAG CAGCTTTGCT CCTTCGCTTT
5941 CTGGGCTCAG AGGCTGGGAA GGGGTGGGTC CGGGGGCGGG CTCAGGGGCG GGCTCAGGGG
6001 CGGGGCGGGC GCCCGAAGGT CCTCCGGAGG CCCGGCATTC TCGCACGCTT CAAAAGCGCA
6061 CGTCTGCCGC GCTGTTCTCC TCTTCCTCAT CTCCGGGCCT TTCGACCATC TAGATCAGGA
6121 TCAATTCACC ATGTCTAGAC TGGACAAGAG CAAAGTCATA AACGGCGCTC TGGAATTACT
6181 CAATGGAGTC GGTATCGAAG GCCTGACGAC AAGGAAACTC GCTCAAAAGC TGGGAGTTGA
6241 GCAGCCTACC CTGTACTGGC ACGTGAAGAA CAAGCGGGCC CTGCTCGATG CCCTGCCAAT
6301 CGAGATGCTG GACAGGCATC ATACCCACTT CTGCCCCCTG GAAGGCGAGT CATGGCAAGA
6361 CTTTCTGCGG AACAACGCCA AGTCATTCCG CTGTGCTCTC CTCTCACATC GCGACGGGGC
6421 TAAAGTGCAT CTCGGCACCC GCCCAACAGA GAAACAGTAC GAAACCCTGG AAAATCAGCT
6481 CGCGTTCCTG TGTCAGCAAG GCTTCTCCCT GGAGAACGCA CTGTACGCTC TGTCCGCCGT
6541 GGGCCACTTT ACACTGGGCT GCGTATTGGA GGAACAGGAG CATCAAGTAG CAAAAGAGGA
6601 AAGAGAGACA CCTACCACCG ATTCTATGCC CCCACTTCTG AGACAAGCAA TTGAGCTGTT
6661 CGACCGGCAG GGAGCCGAAC CTGCCTTCCT TTTCGGCCTG GAACTAATCA TATGTGGCCT
6721 GGAGAAACAG CTAAAGTGCG AAAGCGGCGG GCCGGCCGAC GCCCTTGACG ATTTTGACTT
6781 AGACATGCTC CCAGCCGATG CCCTTGACGA CTTTGACCTT GATATGCTGC CTGCTGACGC
6841 TCTTGACGAT TTTGACCTTG ACATGCTCCC CGGGGGAAGT GGCGCGACCA ACTTTAGCCT
6901 GCTGAAACAG GCGGGCGATG TGGAAGAAAA CCCAGGACCC ATGGCTTCGT ACCCCGGCCA
6961 TCAACACGCG TCTGCGTTCG ACCAGGCTGC GCGTTCTCGC GGCCATAGCA ACCGACGTAC
7021 GGCGTTGCGC CCTCGCCGGC AGCAAGAAGC CACGGAAGTC CGCCCGGAGC AGAAAATGCC
7081 CACGCTACTG CGGGTTTATA TAGACGGTCC CCACGGGATG GGGAAAACCA CCACCACGCA
7141 ACTGCTGGTG GCCCTGGGTT CGCGCGACGA TATCGTCTAC GTACCCGAGC CGATGACTTA
7201 CTGGCGGGTG CTGGGGGCTT CCGAGACAAT CGCGAACATC TACACCACAC AACACCGCCT
7261 CGACCAGGGT GAGATATCGG CCGGGGACGC GGCGGTGGTA ATGACAAGCG CCCAGATAAC
7321 AATGGGCATG CCTTATGCCG TGACCGACGC CGTTCTGGCT CCTCATATCG GGGGGGAGGC
7381 TGGGAGCTCA CATGCCCCGC CCCCGGCCCT CACCCTCATC TTCGACCGCC ATCCCATCGC
7441 CGCCCTCCTG TGCTACCCGG CCGCGCGATA CCTTATGGGC AGCATGACCC CCCAGGCCGT
7501 GCTGGCCGTTC GTGGCCCTCA TCCCGCCGAC CTTGCCCGGC ACAACATCG TGTTGGGGGC
7561 CCTTCCGGAG GACAGACACA TCGACCGCCT GGCCAAACGC CAGCGCCCCG GCGAGCGGCT
7621 TGACCTGGCT ATGCTGGCCG CGATTCGCCG CGTTTACGGG CTGCTTGCCA ATACGGTGCG
7681 GTATCTGCAG GGCGGCGGGT CGTGGCGGGA GGATTGGGGA CAGCTTTCGG GGACGGCCGT
7741 GCCGCCCCAG GGTGCCGAGC CCCAGAGCAA CGCGGGCCCA CGACCCCATA TCGGGGACAC
7801 GTTATTTACC CTGTTTCGGG CCCCCGAGTT GCTGGCCCCC AACGGCGACC TGTATAACGT
7861 GTTTGCCTGG GCCTTGGACG TCTTGGCCAA ACGCCTCCGT CCCATGCACG TCTTTATCCT
7921 GGATTACGAC CAATCGCCCG CCGGCTGCCG GGACGCCCTG CTGCAACTTA CCTCCGGGAT
7981 GGTCCAGACC CACGTCACCA CCCCCGGCTC CATACCGACG ATATGCGACC TGGCGCGCAC
8041 GTTTGCCCGG GAGATGGGGG AGGCTAACTG ACTTAAGCTC TAGCCAATTC GAGCTCGGTA
8101 CCTTTAAGAC CAATGACTTA CAAGGCAGCT GTAGATCTTA GCCACTTTTT AAAGAAAAG
8161 GGGGGACTGG AAGGGCTAAT TCACTCCCAA CGAAGACAAG ATCTGCTTTT TGCTTGTACT
8221 GGGTCTCTCT GGTTAGACCA GATCTGAGCC TGGGAGCTCT CTGGCTAACT AGGGAACCCA
8281 CTGCTTAAGC CTCAATAAAG CTTGCCTTGA GTGCTTCAAG TAGTGTGTGC CCGTCTGTTG
8341 TGTGACTCTG GTAACTAGAG ATCCCTCAGA CCCTTTTAGT CAGTGTGGAA AATCTCTAGC
8401 AGTAGTAGTT CATGTCATCT TATTATTCAG TATTTATAAC TTGCAAAGAA ATGAATATCA
8461 GAGAGTGAGA GGAACTTGTT TATTGCAGCT TATAATGGTT ACAAATAAAG CAATAGCATC
8521 ACAAATTTCA CAAATAAAGC ATTTTTTTCA CTGCATTCTA GTTGTGGTTT GTCCAAACTC
8581 ATCAATGTAT CTTATCATGT CTGGCTCTAG CTATCCCGCC CTAACTCCG CCCATCCCGC
8641 CCCTAACTCC GCCCAGTTCC GCCCATTCTC CGCCCCATGG CTGACTAATT TTTTTTATTT
8701 ATGCAGAGGC CGAGGCCGCC TCGGCCTCTG AGCTATTCCA GAAGTAGTGA GGAGGCTTTT
8761 TTGGAGGCCT AGGCTTTTGC GTCGAGACGT ACCCAATTCG CCCTATAGTG AGTCGTATTA
8821 CGCGCGCTCA CTGGCCGTCG TTTTACAACG TCGTGACTGG GAAAACCCTG GCGTTACCCA
```

| Sequence Listing |
|---|
| 8881 ACTTAATCGC CTTGCAGCAC ATCCCCCTTT CGCCAGCTGG CGTAATAGCG AAGAGGCCCG
8941 CACCGATCGC CCTTCCCAAC AGTTGCGCAG CCTGAATGGC GAATGGCGCG ACGCGCCCTG
9001 TAGCGGCGCA TTAAGCGCGG CGGGTGTGGT GGTTACGCGC AGCGTGACCG CTACACTTGC
9061 CAGCGCCCTA GCGCCCGCTC CTTTCGCTTT CTTCCCTTCC TTTCTCGCCA CGTTCGCCGG
9121 CTTTCCCCGT CAAGCTCTAA ATCGGGGGCT CCCTTTAGGG TTCCGATTTA GTGCTTTACG
9181 GCACCTCGAC CCCAAAAAAC TTGATTAGGG TGATGGTTCA CGTAGTGGGC CATCGCCCTG
9241 ATAGACGGTT TTTCGCCCTT TGACGTTGGA GTCCACGTTC TTTAATAGTG GACTCTTGTT
9301 CCAAACTGGA ACAACACTCA ACCCTATCTC GGTCTATTCT TTTGATTTAT AAGGGATTTT
9361 GCCGATTTCG GCCTATTGGT TAAAAAATGA GCTGATTTAA CAAAAATTTA ACGCGAATTT
9421 TAACAAAATA TTAACGTTTA CAATTTCC SEQ ID NO. 23
   1 CAGGTGGCAC TTTTCGGGGA AATGTGCGCG GAACCCCTAT TTGTTTATTT TTCTAAATAC
  61 ATTCAAATAT GTATCCGCTC ATGAGACAAT AACCCTGATA AATGCTTCAA TAATATTGAA
 121 AAAGGAAGAG TATGAGTATT CAACATTTCC GTGTCGCCCT TATTCCCTTT TTTGCGGCAT
 181 TTTGCCTTCC TGTTTTTGCT CACCCAGAAA CGCTGGTGAA AGTAAAAGAT GCTGAAGATC
 241 AGTTGGGTGC ACGAGTGGGT TACATCGAAC TGGATCTCAA CAGCGGTAAG ATCCTTGAGA
 301 GTTTTCGCCC CGAAGAACGT TTTCCAATGA TGAGCACTTT TAAAGTTCTG CTATGTGGCG
 361 CGGTATTATC CCGTATTGAC GCCGGGCAAG AGCAACTCGG TCGCCGCATA CACTATTCTC
 421 AGAATGACTT GGTTGAGTAC TCACCAGTCA CAGAAAAGCA TCTTACGGAT GGCATGACAG
 481 TAAGAGAATT ATGCAGTGCT GCCATAACCA TGAGTGATAA CACTGCGGCC AACTTACTTC
 541 TGACAACGAT CGGAGGACCG AAGGAGCTAA CCGCTTTTTT GCACAACATG GGGGATCATG
 601 TAACTCGCCT TGATCGTTGG GAACCGGAGC TGAATGAAGC CATACCAAAC GACGAGCGTG
 661 ACACCACGAT GCCTGTAGCA ATGGCAACAA CGTTGCGCAA ACTATTAACT GGCGAACTAC
 721 TTACTCTAGC TTCCCGGCAA CAATTAATAG ACTGGATGGA GGCGGATAAA GTTGCAGGAC
 781 CACTTCTGCG CTCGGCCCTT CCGGCTGGCT GGTTTATTGC TGATAAATCT GGAGCCGGTG
 841 AGCGTGGGTC TCGCGGTATC ATTGCAGCAC TGGGGCCAGA TGGTAAGCCC TCCCGTATCG
 901 TAGTTATCTA CACGACGGGG AGTCAGGCAA CTATGGATGA ACGAAATAGA CAGATCGCTG
 961 AGATAGGTGC CTCACTGATT AAGCATTGGT AACTGTCAGA CCAAGTTTAC TCATATATAC
1021 TTTAGATTGA TTTAAAACTT CATTTTTAAT TTAAAAGGAT CTAGGTGAAG ATCCTTTTTG
1081 ATAATCTCAT GACCAAAATC CCTTAACGTG AGTTTTCGTT CCACTGAGCG TCAGACCCCG
1141 TAGAAAAGAT CAAAGGATCT TCTTGAGATC CTTTTTTTCT GCGCGTAATC TGCTGCTTGC
1201 AAACAAAAAA ACCACCGCTA CCAGCGGTGG TTTGTTTGCC GGATCAAGAG CTACCAACTC
1261 TTTTTCCGAA GGTAACTGGC TTCAGCAGAG CGCAGATACC AAATACTGTC CTTCTAGTGT
1321 AGCCGTAGTT AGGCCACCAC TTCAAGAACT CTGTAGCACC GCCTACATAC CTCGCTCTGC
1381 TAATCCTGTT ACCAGTGGCT GCTGCCAGTG GCGATAAGTC GTGTCTTACC GGGTTGGACT
1441 CAAGACGATA GTTACCGGAT AAGGCGCAGC GGTCGGGCTG AACGGGGGGT TCGTGCACAC
1501 AGCCCAGCTT GGAGCGAACG ACCTACACCG AACTGAGATA CCTACAGCGT GAGCTATGAG
1561 AAAGCGCCAC GCTTCCCGAA GGGAGAAAGG CGGACAGGTA TCCGGTAAGC GGCAGGGTCG
1621 GAACAGGAGA GCGCACGAGG GAGCTTCCAG GGGGAAACGC CTGGTATCTT TATAGTCCTG
1681 TCGGGTTTCG CCACCTCTGA CTTGAGCGTC GATTTTTGTG ATGCTCGTCA GGGGGGCGGA
1741 GCCTATGGAA AAACGCCAGC AACGCGGCCT TTTTACGGTT CCTGGCCTTT TGCTGGCCTT
1801 TTGCTCACAT GTTCTTTCCT GCGTTATCCC CTGATTCTGT GGATAACCGT ATTACCGCCT
1861 TTGAGTGAGC TGATACCGCT CGCCGCAGCC GAACGACCGA GCGCAGCGAG TCAGTGAGCG
1921 AGGAAGCGGA AGAGCGCCCA ATACGCAAAC CGCCTCTCCC CGCGCGTTGG CCGATTCATT
1981 AATGCAGCTG GCACGACAGG TTTCCCGACT GGAAAGCGGG CAGTGAGCGC AACGCAATTA
2041 ATGTGAGTTA GCTCACTCAT TAGGCACCCC AGGCTTTACA CTTTATGCTT CCGGCTCGTA
2101 TGTTGTGTGG AATTGTGAGC GGATAACAAT TTCACACAGG AAACAGCTAT GACCATGATT
2161 ACGCCAAGCG CGCAATTAAC CCTCACTAAA GGGAACAAAA GCTGGAGCTG CAAGCTTGGC
2221 CATTGCATAC GTTGTATCCA TATCATAATA TGTACATTTA TATTGGCTCA TGTCCAACAT
2281 TACCGCCATG TTGACATTGA TTATTGACTA GTTATTAATA GTAATCAATT ACGGGGTCAT
2341 TAGTTCATAG CCCATATATG GAGTTCCGCG TTACATAACT TACGGTAAAT GGCCCGCCTG
2401 GCTGACCGCC CAACGACCCC GCCCATTGA CGTCAATAAT GACGTATGTT CCCATAGTAA
2461 CGCCAATAGG GACTTTCCAT TGACGTCAAT GGGTGGAGTA TTTACGGTAA ACTGCCCACT
2521 TGGCAGTACA TCAAGTGTAT CATATGCCAA GTACGCCCCC TATTGACGTC AATGACGGTA
2581 AATGGCCCGC CTGGCATTAT GCCCAGTACA TGACCTTATG GACTTTCCT ACTTGGCAGT
2641 ACATCTACGT ATTAGTCATC GCTATTACCA TGGTGATGCG GTTTTGGCAG TACATCAATG
2701 GGCGTGGATA GCGGTTTGAC TCACGGGGAT TTCCAAGTCT CCACCCCATT GACGTCAATG
2761 GGAGTTTGTT TTGGCACCAA AATCAACGGG ACTTTCCAAA ATGTCGTAAC AACTCCGCCC
2821 CATTGACGCA AATGGGCGGT AGGCGTGTAC GGTGGGAGGT CTATATAAGC AGAGCTCGTT
2881 TAGTGAACCG GGGTCTCTCT GGTTAGACCA GATCTGAGCC TGGGAGCTCT CTGGCTAACT
2941 AGGGAACCCA CTGCTTAAGC CTCAATAAAG CTTGCCTTGA GTGCTTCAAG TAGTGTGTGC
3001 CCGTCTGTTG TGTGACTCTG GTAACTAGAG ATCCCTCAGA CCCTTTTAGT CAGTGTGGAA
3061 AATCTCTAGC AGTGGCGCCC GAACAGGGAC CTGAAAGCGA AAGGGAAACC AGAGGAGCTC
3121 TCTCGACGCA GGACTCGGCT TGCTGAAGCG CGCACGGCAA GAGGCGAGGG GCGGCGACTG
3181 GTGAGTACGC CAAAAATTTT GACTAGCGGA GGCTAGAAGG AGAGAGATGG GTGCGAGAGC
3241 GTCAGTATTA AGCGGGGGAG AATTAGATCG CGATGGGAAA AAATTCGGTT AAGGCCAGGG
3301 GGAAAGAAAA AATATAAATT AAAACATATA GTATGGGCAA GCAGGGAGCT AGAACGATTC
3361 GCAGTTAATC CTGGCCTGTT AGAAACATCA GAAGGCTGTA GACAAATACT GGGACAGCTA
3421 CAACCATCCC TTCAGACAGG ATCAGAAGAA CTTAGATCAT TATATAATAC AGTAGCAACC
3481 CTCTATTGTG TGCATCAAAG GATAGAGATA AAAGACACCA AGGAAGCTTT AGACAAGATA
3541 GAGGAAGAGC AAAACAAAAG TAAGACCACC GCACAGCAAG CGGCCGCTGA TCTTCAGACC
3601 TGGAGGAGGA GATATGAGGG ACAATTGGAG AAGTGAATTA TATAAATATA AAGTAGTAAA
3661 AATTGAACCA TTAGGAGTAG CACCCACCAA GGCAAAGAGA AGAGTGGTGC AGAGAGAAAA
3721 AAGAGCAGTG GGAATAGGAG CTTTGTTCCT TGGGTTCTTG GGAGCAGCAG GAAGCACTAT
3781 GGGCGCAGCC TCAATGACGC TGACGGTACA GGCCAGACAA TTATTGTCTG GTATAGTGCA
3841 GCAGCAGAAC AATTTGCTGA GGGCTATTGA GGCGCAACAG CATCTGTTGC AACTCACAGT |

-continued

Sequence Listing

```
3901 CTGGGGCATC AAGCAGCTCC AGGCAAGAAT CCTGGCTGTG GAAAGATACC TAAAGGATCA
3961 ACAGCTCCTG GGGATTTGGG GTTGCTCTGG AAAACTCATT TGCACCACTG CTGTGCCTTG
4021 GAATGCTAGT TGGAGTAATA AATCTCTGGA ACAGATTGGA ATCACACGAC CTGGATGGAG
4081 TGGGACAGAG AAATTAACAA TTACACAAGC TTAATACACT CCTTAATTGA AGAATCGCAA
4141 AACCAGCAAG AAAAGAATGA ACAAGAATTA TTGGAATTAG ATAAATGGGC AAGTTTGTGG
4201 AATTGGTTTA ACATAACAAA TTGGCTGTGG TATATAAAAT TATTCATAAT GATAGTAGGA
4261 GGCTTGGTAG GTTTAAGAAT AGTTTTTGCT GTACTTTCTA TAGTGAATAG AGTTAGGCAG
4321 GGATATTCAC CATTATCGTT TCAGACCCAC CTCCCAACCC CGAGGGGACC CGACAGGCCC
4381 GAAGGAATAG AAGAAGAAGG TGGAGAGAGA GACAGAGACA GATCCATTCG ATTAGTGAAC
4441 GGATCTCGAC GGTATCGATC TCGACACAAA TGGCAGTATT CATCCACAAT TTTAAAAGAA
4501 AAGGGGGGAT TGGGGGGTAC AGTGCAGGGG AAAGAATAGT AGACATAATA GCAACAGACA
4561 TACAAACTAA AGAATTACAA AAACAAATTA CAAAAATTCA AAATTTTCGG GTTTATTACA
4621 GGGACAGCAG AGATCCAGTT TGGGTCGAGG ATATCGGATC GGAATTAATT CATCGATCGA
4681 TTAGTCCAAT TTGTTAAAGA CAGGATATCA GTGGTCCAGG CTCTAGTTTT GACTCAACAA
4741 TATCACCAGC TGAAGCCTAT AGAGTACGAG CCATAGATAG AATAAAAGAT TTTATTTAGT
4801 CTCCAGAAAA AGGGGGGAAT GAAAGACCCC ACCTGCTAGGT TTGGCAAGCT AGGATCAAGG
4861 TTAGGAACAG AGAGACAGCA GAATATGGGC AAACAGGAT ATCTGTGGTA AGCAGTTCCT
4921 GCCCCGGCTC AGGGCCAAGA ACAGTTGGAA CAGCAGAATA TGGGCCAAAC AGGATATCTG
4981 TGGTAAGCAG TTCCTGCCCC GGCTCAGGGC CAAGAACAGA TGGTCCCCAG ATGCGGTCCC
5041 GCCCTCAGCA GTTTCTAGAG AACCATCAGA TGTTTCCAGG GTGCCCCAAG GACCTGAAAT
5101 GACCCTGTGC CTTATTTGAA CTAACCAATC AGTTCGCTTC TCGCTTCTGT TCGCGCGCTT
5161 CTGCTCCCCG AGCTCAATAA AAGAGCCCAC AACCCCTCAC TCGGCGCGAT CTAGATCTCG
5221 AGCTCGAATT CGCCCTTCCT GAGATCACCG GTAGGAGGGC CATCATGAAC TTTCTGCTGT
5281 CTTGGGTGCA TTGGAGCCTT GCCTTGCTGC TCTACCTCCA CCATGCCAAG TGGTCCCAGG
5341 CTGCACCCAT GGCAGAAGGA GGAGGGCAGA ATCATCACGA AGTGGTGAAG TTCATGGATG
5401 TCTATCAGCG CAGCTACTGC CATCCAATCG AGACCCTGGT GGACATCTTC CAGGAGTACC
5461 CTGATGAGAT CGAGTACATC TTCAAGCCAT CCTGTGTGCC CCTGATGCGA TGCGGGGGCT
5521 GCTGCAATGA CGAGGGCCTG GAGTGTGTGC CCACTGAGGA GTCCAACATC ACCATGCAGA
5581 TTATGCGGAT CAAACCTCAC CAAGGCCAGC ACATAGGAGA GATGAGCTTC CTACAGCACA
5641 ACAAATGTGA ATGCAGACCA AAGAAAGATA GAGCAAGACA AGAAAATCCC TGTGGGCCTT
5701 GCTCAGAGCG GAGAAAGCAT TTGTTTGTAC AAGATCCGCA GACGTGTAAA TGTTCCTGCA
5761 AAAACACAGA CTCGCGTTGC AAGGCGAGGC AGCTTGAGTT AAACGAACGT ACTTGCAGAT
5821 GTGACAAGCC GAGGCGGTGA AAGGGCGAAT TCTACCGGGT AGGGGAGGCG CTTTTCCCAA
5881 GGCAGTCTGG AGCATGCGCT TTAGCAGCCC CGCTGGCACT TGGCGCTACA CAAGTGGCCT
5941 CTGGCCTCGC ACACATTCCA CATCCACCGG TAGGCGCCAA CCGGCTCCGT TCTTTGGTGG
6001 CCCCTTCGCG CCACCTTCTA CTCCTCCCCT AGTCAGGAAG TTCCCCCCCG CCCCGCAGCT
6061 CGCGTCGTGC AGGACGTGAC AAATGGAAGT AGCACGTCTC ACTAGTCTCG TGCAGATGGA
6121 CAGCACCGCT GAGCAATGGA AGCGGGTAGG CCTTTGGGGC AGCGGCCAAT AGCAGCTTTG
6181 CTCCTTCGCT TTCTGGGCTC AGAGGCTGGG AAGGGGTGGG TCCGGGGCG GCTCAGGGG
6241 CGGGCTCAGG GGCGGGGCGG GCGCCCGAAG GTCCTCCGGA GGCCCGGCAT TCTCGCACGC
6301 TTCAAAAGCG CACGTCTGCC GCGCTGTTCT CCTCTTCCTG ATCTCCGGGC CTTTCGACCA
6361 TCTAGATCAG GATCCCTCGA GCCCCCTCGC GACCATGGCT TCGTACCCCG GCCATCAACA
6421 CGCGTCTGCG TTCGACCAGG CTGCGCGTTC TCGCGGCCAT AGCAACCGAC GTACGGCGTT
6481 GCGCCCTCGC CGGCAGCAAG AAGCCACGGA AGTCCGCCCG GAGCAGAAAA TGCCCACGCT
6541 ACTGCGGGTT TATATAGACG TCTCCCACGG GATGGGGAAA ACCACCACCA CGCAACTGCT
6601 GGTGGCCCTG GGTTCGCGCG ACGATATCGT CTACGTACCC GAGCCGATGA CTTACTGGCG
6661 GGTGCTGGGG GCTTCCGAGA CAATCGCGAA CATCTACACC ACACAACACC GCCTCGACCA
6721 GGGTGAGATA TCGGCCGGGG ACGCGGCGGT GGTAATGACA AGCGCCCAGA TAACAATGGG
6781 CATGCCTTAT GCCGTGACCG ACGCCGTTCT GGCTCCTCAT ATCGGGGGGG AGGCTGGGAG
6841 CTCACATGCC CCGCCCCCGG CCCTCACCCT CATCTTCGAC CGCCATCCCA TCGCCGCCCT
6901 CCTGTGCTAC CCGGCCGCGC GATACCTTAT GGGCAGCATG ACCCCCCAGG CCGTGCTGGC
6961 GTTCGTGGCC CTCATCCCGC CGACCTTGCC CGGCACAAAC ATCGTGTTGG GGGCCCTTCC
7021 GGAGGACAGA CACATCGACC GCCTGGCCAA ACGCCAGCGC CCGGCCGAGC GGCTTGACCT
7081 GGCTATGCTG GCCGCGATTC GCCGCGTTTA CGGGCTGCTT GCCAATACGG TGCGGTATCT
7141 GCAGGGCGGC GGGTCGTGGC GGGAGGATTG GGGACAGCTT TCGGGGACGG CCGTGCCGCC
7201 CCAGGGTGCC GAGCCCCAGA GCAACGCGGG CCCACGACCC CATATCGGGG ACACGTTATT
7261 TACCCTGTTT CGGGCCCCCG AGTTGCTGGC CCCCAACGGC GACCTGTATA ACGTGTTTGC
7321 CTGGGCCTTG GACGTCTTGG CCAAACGCCT CCGTCCCATG CACGTCTTTA TCCTGGATTA
7381 CGACCAATCG CCCGCCGGCT GCCGGGACGC CCTGCTGCAA CTTACCTCCG GGATGGTCCA
7441 GACCCACGTC ACCACCCCCG GCTCCATACC GACGATATGC GACCTGGCGC GCACGTTTGC
7501 CCGGGAGATG GGGGAGGCTA ACTGACTTAA GCTTGGTACC GAGCTCGGAT CCAGGGGGGC
7561 TAGCGATAAT CAACCTCTGG ATTACAAAAT TTGTGAAAGA TTGACTGGTA TTCTTAACTA
7621 TGTTGCTCCT TTTACGCTAT GTGGATACGC TGCTTTAATG CCTTTGTATC ATGCTATTGC
7681 TTCCCGTATG GCTTTCATTT TCTCCTCCTT GTATAAATCC TGGTTGCTGT CTCTTTATGA
7741 GGAGTTGTGG CCCGTTGTCA GGCAACGTGG CGTGGTGTGC ACTGTGTTTG CTGACGCAAC
7801 CCCCACTGGT TGGGGCATTG CCACCACCTG TCAGCTCCTT TCCGGGACTT TCGCTTTCCC
7861 CCTCCCTATT GCCACGGCGG AACTCATCGC CGCCTGCCTT GCCCGCTGCT GGACAGGGGC
7921 TCGGCTGTTG GCACTGACA ATTCCGTGGT GTTGTCGGGG AAATCATCGT CCTTTCCTTG
7981 GCTGCTCGCC TGTGTTGCCA CCTGGATTCT GCGCGGGACG TCCTTCTGCT ACGTCCCTTC
8041 GGCCCTCAAT CCAGCGGACC TTCCTTCCCG CGGCCTGCTG CCGGCTCTGC GGCCTCTTCC
8101 GCGTCTTCGC CTTCGCCCTC AGACGAGTCG GATCTCCCTT TGGGCCGCCT CCCCGCATCG
8161 CTAGCCAATT CGAGCTCGGT ACCTTTAAGA CCAATGACTT ACAAGGCAGC TGTAGATCTT
8221 AGCCACTTTT TAAAAGAAAA GGGGGGACTG GAAGGGCTAA TTCACTCCCA ACGAAGACAA
8281 GATCTGCTTT TTGCTTGTAC TGGGTCTCTC TGGTTAGACC AGATCTGAGC CTGGGAGCTC
8341 TCTGGCTAAC TAGGGAACCC ACTGCTTAAG CCTCAATAAA GCTTGCCTTG AGTGCTTCAA
8401 GTAGTGTGTG CCCGTCTGTT GTGTGACTCT GGTAACTAGA GATCCCTCAG ACCCTTTTAG
8461 TCAGTGTGGA AAATCTCTAG CAGTAGTAGT TCATGTCATC TTATTATTCA GTATTTATAA
```

|                                                                                           |
|-------------------------------------------------------------------------------------------|
| 8521 CTTGCAAAGA AATGAATATC AGAGAGTGAG AGGAACTTGT TTATTGCAGC TTATAATGGT                     |
| 8581 TACAAATAAA GCAATAGCAT CACAAATTTC ACAAATAAAG CATTTTTTTC ACTGCATTCT                     |
| 8641 AGTTGTGGTT TGTCCAAACT CATCAATGTA TCTTATCATG TCTGGCTCTA GCTATCCCGC                     |
| 8701 CCCTAACTCC GCCCATCCCG CCCCTAACTC CGCCCAGTTC CGCCCATTCT CCGCCCCATG                     |
| 8761 GCTGACTAAT TTTTTTTATT TATGCAGAGG CCGAGGCCGC CTCGGCCTCT GAGCTATTCC                     |
| 8821 AGAAGTAGTG AGGAGGCTTT TTTGGAGGCC TAGGCTTTTG CGTCGAGACG TACCCAATTC                     |
| 8881 GCCCTATAGT GAGTCGTATT ACGCGCGCTC ACTGGCCGTC GTTTTACAAC GTCGTGACTG                     |
| 8941 GGAAAACCCT GGCGTTACCC AACTTAATCG CCTTGCAGCA CATCCCCCTT TCGCCAGCTG                     |
| 9001 GCGTAATAGC GAAGAGGCCC GCACCGATCG CCCTTCCCAA CAGTTGCGCA GCCTGAATGG                     |
| 9061 CGAATGGCGC GACGCGCCCT GTAGCGGCGC ATTAAGCGCG GCGGGTGTGG TGGTTACGCG                     |
| 9121 CAGCGTGACC GCTACACTTG CCAGCGCCCT AGCGCCCGCT CCTTTCGCTT TCTTCCCTTC                     |
| 9181 CTTTCTCGCC ACGTTCGCCG GCTTTCCCCG TCAAGCTCTA AATCGGGGGC TCCCTTTAGG                     |
| 9241 GTTCCGATTT AGTGCTTTAC GGCACCTCGA CCCCAAAAAA CTTGATTAGG GTGATGGTTC                     |
| 9301 ACGTAGTGGG CCATCGCCCT GATAGACGGT TTTTCGCCCT TTGACGTTGG AGTCCACGTT                     |
| 9361 CTTTAATAGT GGACTCTTGT TCCAAACTGG AACAACACTC AACCCTATCT CGGTCTATTC                     |
| 9421 TTTTGATTTA TAAGGGATTT TGCCGATTTC GGCCTATTGG TTAAAAAATG AGCTGATTTA                     |
| 9481 ACAAAAATTT AACGCGAATT TTAACAAAAT ATTAACGTTT ACAATTTCC                                 |
| //                                                                                        |

The invention claimed is:

1. A vector comprising:
  i) a polynucleotide comprising the following operatively linked to each other:
    a) a Moloney murine leukemia virus long terminal repeat (MNDU3) promoter that has the nucleic acid sequence of nucleotides 285-844 of SEQ ID NO: 23,
    b) a nucleic acid sequence encoding a 165A isoform of a vascular endothelial growth factor (VEGF), and
    c) a woodchuck post-regulatory element (WPRE) consisting essentially of nucleotides 7564-8160 of SEQ ID NO: 23, or
  ii) the complement of the polynucleotide.

2. The vector of claim 1, wherein the nucleic acid sequence encoding the 165A isoform of VEGF consists essentially of nucleotides 5226-5852 of SEQ ID NO: 23.

3. The vector of claim 1, wherein the vector comprises pPCL3 plasmid.

4. A viral packaging system comprising the vector of claim 1, a packaging plasmid, and an envelope plasmid.

5. The viral packaging system of claim 4, wherein the envelope plasmid is a plasmid comprising a S. aureus ZZ domain sequence.

6. The viral packaging system of claim 4, further comprising (d) a packaging cell line.

7. An isolated cell comprising the vector of claim 1.

8. The isolated cell of claim 7, wherein the cell is a stem cell.

9. The isolated cell of claim 8, wherein the cell is an isolated marrow stromal cell.

10. The isolated cell of claim 9, wherein the isolated marrow stromal cell is a CD34−/CD45−/CD105+/CD90+/CD73+ marrow stromal cell.

11. The isolated cell of claim 8 or 10 wherein the cell expresses at least $5 \times 10^{-6}$ ng of 165A VEGF protein or a biological equivalent thereof.

12. A method for treating peripheral artery disease and/or critical limb ischemia in a patient in need thereof comprising administering an effective amount of the isolated cell of claim 8 or 10.

13. A method for promoting wound healing, promoting or increasing the rate of angiogenesis or wound healing, decreasing the size of a wound, or decreasing the time to wound healing in a patient in need thereof comprising administering an effective amount of the isolated cell of claim 8 or 10.

14. A method for salvaging a limb in a patient with peripheral artery disease or critical limb ischemia comprising administering an effective amount the isolated cell of claim 8 or 10.

15. The method of claim 14, wherein the administration is by intravenous injection or by intramuscular injection.

16. The method of claim 14, wherein the cells are administered locally to the ischemic area of the limb.

17. An expanded population of isolated marrow stromal cells of claim 11.

18. The expanded population of claim 17, wherein the population is a substantially homogeneous marrow stromal cell population.

19. A composition comprising the isolated marrow stromal cell of claim 11 and a carrier.

20. The composition of claim 19, wherein the carrier is a pharmaceutically acceptable carrier.

* * * * *